United States Patent
D'Lima et al.

(10) Patent No.: US 11,173,049 B2
(45) Date of Patent: *Nov. 16, 2021

(54) BALANCING DEVICE FOR ARTHROPLASTY AND METHODS FOR USE

(71) Applicant: XpandOrtho, Inc., La Jolla, CA (US)

(72) Inventors: Darryl D. D'Lima, San Diego, CA (US); Clifford W. Colwell, La Jolla, CA (US)

(73) Assignee: XpandOrtho, Inc., La Jolla, CA (US)

( * ) Notice: Subject to any disclaimer, the term of this patent is extended or adjusted under 35 U.S.C. 154(b) by 174 days.

This patent is subject to a terminal disclaimer.

(21) Appl. No.: 16/256,823

(22) Filed: Jan. 24, 2019

(65) Prior Publication Data

US 2019/0151118 A1 May 23, 2019

Related U.S. Application Data

(63) Continuation of application No. 15/080,415, filed on Mar. 24, 2016, now Pat. No. 10,206,791.

(Continued)

(51) Int. Cl.
*A61F 2/46* (2006.01)
*A61B 17/15* (2006.01)
(Continued)

(52) U.S. Cl.
CPC .......... *A61F 2/4657* (2013.01); *A61B 17/025* (2013.01); *A61B 17/154* (2013.01);
(Continued)

(58) Field of Classification Search
CPC .................................................. A61F 2/4657
See application file for complete search history.

(56) References Cited

U.S. PATENT DOCUMENTS 5,540,696 A * 7/1996 Booth, Jr. ............ A61B 17/025
606/88
5,688,280 A * 11/1997 Booth, Jr. ............ A61B 17/025
606/88

(Continued)

FOREIGN PATENT DOCUMENTS

CN 101612055 A 12/2009
DE 10335410 A1 2/2005
(Continued)

OTHER PUBLICATIONS

"eLIBRA Dynamic Knee Balancing System Surgical Technique and System Overview," Zimmer® Natural Knee II, Zimmer Personal Fit. Renewed Life.™ (25 pages). Date unknown.

(Continued)

*Primary Examiner* — Zade Coley
(74) *Attorney, Agent, or Firm* — Greenberg Traurig, LLP

(57) ABSTRACT

A joint balancing insert with an actuated mechanism is for balancing a joint during a joint surgery is disclosed. The joint balancing insert includes a first plate, a second plate and an actuator there between. The second plate includes an integrated mounting portion for mounting a cutting block used to guide surgical cuts of the joint during the joint surgery. Various configurations of the integrated mounting portion may be implemented in the insert to provide for mounting various types of cutting blocks, such as cutting blocks for tibial cuts, femoral cuts, and distal femoral cuts.

16 Claims, 32 Drawing Sheets

Related U.S. Application Data

(60) Provisional application No. 62/137,661, filed on Mar. 24, 2015.

(51) Int. Cl.
| | | |
|---|---|---|
| *A61B 17/17* | (2006.01) | |
| *A61B 17/02* | (2006.01) | |
| *A61B 17/00* | (2006.01) | |
| *A61B 90/00* | (2016.01) | |
| *A61F 2/38* | (2006.01) | |

(52) U.S. Cl.
CPC ........ *A61B 17/155* (2013.01); *A61B 17/1764* (2013.01); *A61B 2017/00022* (2013.01); *A61B 2017/00557* (2013.01); *A61B 2017/0268* (2013.01); *A61B 2090/061* (2016.02); *A61B 2090/065* (2016.02); *A61F 2/38* (2013.01); *A61F 2002/4658* (2013.01); *A61F 2002/4666* (2013.01); *A61F 2002/4668* (2013.01); *A61F 2002/4694* (2013.01)

(56) References Cited

U.S. PATENT DOCUMENTS

| | | | |
|---|---|---|---|
| 5,733,292 A * | 3/1998 | Gustilo | A61B 17/025 606/86 R |
| 6,022,377 A * | 2/2000 | Nuelle | A61B 17/025 606/102 |
| 6,375,682 B1 * | 4/2002 | Fleischmann | A61F 2/4425 623/17.12 |
| 7,442,196 B2 | 10/2008 | Fisher et al. | |
| 7,578,821 B2 | 8/2009 | Fisher et al. | |
| 7,615,055 B2 | 11/2009 | DiSilvestro | |
| 7,632,283 B2 | 12/2009 | Heldreth | |
| 7,708,740 B1 | 5/2010 | Bonutti | |
| 7,837,691 B2 | 11/2010 | Cordes et al. | |
| 8,337,508 B2 | 12/2012 | Lavallee et al. | |
| 8,491,589 B2 | 7/2013 | Fisher et al. | |
| 2004/0019382 A1 | 1/2004 | Amirouche et al. | |
| 2004/0064191 A1 | 4/2004 | Wasielewski | |
| 2005/0177169 A1 | 8/2005 | Fisher et al. | |
| 2005/0177170 A1 * | 8/2005 | Fisher | A61B 17/02 606/88 |
| 2005/0209600 A1 * | 9/2005 | Fencl | A61B 17/155 606/89 |
| 2006/0009856 A1 | 1/2006 | Sherman et al. | |
| 2006/0149277 A1 * | 7/2006 | Cinquin | A61B 17/025 606/90 |
| 2006/0293685 A1 | 12/2006 | Stone et al. | |
| 2007/0234819 A1 | 10/2007 | Amirouche et al. | |
| 2007/0288095 A1 | 12/2007 | Wirtel et al. | |
| 2008/0058855 A1 | 3/2008 | Reiley et al. | |
| 2009/0182343 A1 | 7/2009 | Trudeau et al. | |
| 2009/0248044 A1 * | 10/2009 | Amiot | G06F 30/17 606/130 |
| 2009/0259319 A1 | 10/2009 | DiSilvestro et al. | |
| 2009/0270987 A1 | 10/2009 | Heinz et al. | |
| 2010/0217156 A1 | 8/2010 | Fisher et al. | |
| 2010/0249533 A1 * | 9/2010 | Pierce | A61B 17/025 600/300 |
| 2010/0249788 A1 * | 9/2010 | Roche | A61B 5/4509 606/87 |
| 2010/0249789 A1 * | 9/2010 | Rock | A61B 17/2833 606/88 |
| 2010/0326194 A1 | 12/2010 | Stein et al. | |
| 2010/0331633 A1 | 12/2010 | Stein | |
| 2010/0331663 A1 | 12/2010 | Stein | |
| 2010/0331733 A1 | 12/2010 | Stein | |
| 2011/0092859 A1 | 4/2011 | Neubardt | |
| 2011/0213221 A1 * | 9/2011 | Roche | A61B 8/565 600/301 |
| 2011/0270295 A1 | 11/2011 | Litvack et al. | |
| 2011/0319996 A1 | 12/2011 | Barrall | |
| 2012/0172762 A1 | 7/2012 | Boyer et al. | |
| 2012/0259342 A1 * | 10/2012 | Chana | A61B 17/025 606/88 |
| 2012/0290088 A1 | 11/2012 | Amirouche et al. | |
| 2013/0023795 A1 | 1/2013 | Stein et al. | |
| 2013/0066432 A1 | 3/2013 | Colwell, Jr. et al. | |
| 2013/0102929 A1 | 4/2013 | Haight et al. | |
| 2013/0261504 A1 | 10/2013 | Claypool et al. | |
| 2014/0074441 A1 * | 3/2014 | Fitz | A61B 17/154 703/1 |
| 2014/0247336 A1 * | 9/2014 | Vilsmeier | G06K 9/00369 348/77 |

FOREIGN PATENT DOCUMENTS

| | | | | |
|---|---|---|---|---|
| FR | 2935092 A1 | 2/2010 | | |
| JP | 2014-530649 A | 11/2014 | | |
| WO | 2004078047 A1 | 9/2004 | | |
| WO | 2012020460 A1 | 2/2012 | | |
| WO | WO-2012020460 A1 * | 2/2012 | ........... | A61F 2/4657 |
| WO | WO-2013034889 A1 * | 3/2013 | ......... | A61B 17/1764 |
| WO | 2014188184 A1 | 11/2014 | | |

OTHER PUBLICATIONS

"eLIBRA Dynamic Knee Balancing System™ Magnetic Augments," Synvasive Technology, Inc. (2 pages). Date unknown.

"eLIBRA® Dynamic Knee Balancing System Surgical Technique & System Overview," Synvasive® Technology, Inc. (14 pages). Date unknown.

"Optimum Flexion Gap and Ligament Balance," eLIBRA® Dynamic Knee Balancing System (4 pages). Date unknown.

Dennis, MD, "Measured Resection: An Outdated Technique in Total Knee Arthroplasty," Orthopaedic Crossfire® point, ORTHOPEDICS, Sep. 2008, retrieved from the Internet <URL: http://www.healio.com/orthopedics/knee/journals/ortho/2008-9-31-9/%7Bbc12e264-2dc9-47bb-8e8c-ae5130f67371%7D/measured-resection-an-outdated-technique-in-total-knee-arthroplasty>.

ELIBRA® "Dynamic Knee Balancing System Surgical Technique and System Overview," Zimmer® NexGen® Knee, Zimmer Personal Fit. Renewed Life.™ (26 pages). Date unknown.

Extended European Search Report for related EP Patent Application No. 14854207.9, dated May 29, 2017.

Extended European Search Report for related EP Patent Application No. 16769733.3, dated Oct. 10, 2018.

Fetto, MD, et al., "Electronic Measurement of Soft Tissue Balancing Reduces Lateral Releases in Total Knee Arthroplasty," Retrospective Study, Podium Presentation, ISTA, 2009, retrieved from the Internet <URL: http://synvasive.com/resources/eLIBRA-WP-Fetto-2010.pdf>.

Hadley, MD, et al., "Correction of Severe Valgus Deformity with Non-Constrained Total Knee Arthroplasty Design" Case Report, Synvasive® Technology, Inc., retrieved from the Internet <URL: http://synvasive.com/resources/eLIBRA-Whitepaper-Hadley-Fetto.PDF>. Date unknown.

http://synvasive.com/video.php?id=Camarata_eLIBRA_Zimmer_x264&w=640&h=480. Copy not available; website no longer in existence.

http://synvasive.com/video.php?id-Dounchis_Final&w=640&h=480. Copy not available; website no longer in existence.

http://synvasive.com/video.php?id=Kreuzer-TKA-using-eLIBRA_x264&w=640&h=480. Copy not available; website no longer in existence.

International Search Report and Written Opinion dated Feb. 25, 2013 for PCT/US2012/054618.

International Search Report and Written Opinion for related PCT application No. PCT/US2014/060655, dated Jan. 16, 2015, in 9 pages.

International Search Report and Written Opinion for related PCT application No. PCT/US2016/024105, dated Jul. 1, 2016, in 12 pages.

Jian Wu, et al., "A method for dynamically measuring the Soft Tissue Balance in the Total Knee Replacement," IFMBE Proceedings, vol. 14/2. pp. 723-727. Date unknown.

(56) References Cited

OTHER PUBLICATIONS

Kreuzer, MD, et al., "Soft Tissue Balance in Primary Total Knee Arthroplasties Using a Force Sensing Device," Case Report, Podium Presentation, ISTA, 2009, retrieved from the Internet <URL: http://synvasive.com/resources/eLIBRAWP-Esska-2010.pdf>.

Nevins, MD, et al., "Balancing the Perfect Knee, Case Report, Podium Presentation," ISTA, 2009, retrieved from the Internet <URL: http://synvasive.com/resources/eLIBRA-WP-Nevins-2010.pdf>.

Office Action and Search Report in related CN Patent Application No. 201480060335.0, dated Aug. 10, 2017.

Reuse and reprocess of eLIBRA® Soft Tissue Force Sensor Devices, Synvasive Technology, Inc. (1 page). Date unknown.

U. Nolten, et al., "Sensor integrated tibial inlay for soft-tissue balancing" Procedia Chemistry 1 (2009). pp. 1251-1254.

* cited by examiner

BALANCING DEVICE FOR ARTHROPLASTY AND METHODS FOR USE

RELATED APPLICATION

This application is a continuation of U.S. Utility application Ser. No. 15/080,415, filed Mar. 24, 2016, entitled "BALANCING DEVICE FOR ARTHROPLASTY AND METHODS FOR USE," which claims the benefit of U.S. provisional patent application Ser. No. 62/137,661 entitled "BALANCING DEVICE FOR ARTHROPLASTY AND METHODS FOR USE," filed on Mar. 24, 2015, which is hereby incorporated by reference.

FIELD OF THE INVENTION

Various embodiments described herein relate generally to devices and methods for balancing a joint during prosthetic arthroplasty, and to actuated positioning and sensing devices for positioning prosthetic components and balancing a joint during arthroplasty surgery.

BACKGROUND

Arthroplasty involves the repair of a joint by replacing one or more portions of the joint to eliminate pain and improve movement. For example, loss of cartilage or friction between bone surfaces can be treated by inserting an artificial joint, which includes one or more prostheses designed to replace bone surfaces and cartilage while also allowing for a range of movement similar to the original joint.

Knee arthroplasty typically involves resecting (cutting away) the diseased and damaged surfaces of the lower end of the femur (thigh bone), the upper end of the tibia (shin bone), and the joint surface of the patella (knee cap). These surfaces are then replaced by artificial materials. The femoral component or prosthesis is typically made from a cobalt chrome alloy and is attached to the femur with fixation devices such as pegs, often with the use of bone cement to bond the femoral prosthesis to the underlying bone. The tibial component typically consists of two parts—a metal tray (titanium or cobalt chrome alloy) and a polyethylene insert—that are assembled together during surgery. The metal tray is fixed to bone with screws, pegs, or a stem; while the insert is locked into the metal tray and articulates with the femoral component.

The technical challenges in knee arthroplasty are: restoration of the natural alignment of the knee with respect to the hip and the ankle; regaining the range of motion of the knee; and inducing the artificially-implanted knee to move in a manner similar to a normal knee. These goals are accomplished by making the bone cuts at precise locations and orientation relative to the rest of the bone, selecting the appropriate size and shape of the prosthetic components, placing the prostheses at the appropriate location on the bones and with respect to each other, and selecting an insert of appropriate thickness such that the knee joint is neither too lose or too tight.

Despite continuous improvements in the design and manufacture of artificial joints and in surgical instruments, the actual arthroplasty relies primarily on the skill and expertise of the surgeon performing the procedure. Arthroplasty requires that a surgeon not only insert the artificial joint, but also "balance" the joint to ensure that the movement of the artificial joint is as similar as possible to a normal range of motion. Balancing the joint often requires careful measurement and cutting of bone, ligaments and other tissue, as well as load balancing to ensure that the force applied by the bones to the joint is evenly distributed and range of motion testing to determine if the artificial joint is capable of movement in the direction and distance required for normal movement. The balancing process often requires the surgeon to simply physically hold the joint and "feel" whether the movement of the joint and the forces being applied to the joint are correct. As a result, the process of balancing the joint is largely subjective, as it relies upon the experience and knowledge of the surgeon to understand whether the movement of the artificial joint is "about right." Misalignment of any of these parameters may result in limited range of motion of the joint, continued pain at the joint and early failure of the artificial joint due to excess load distribution or friction.

To aid in balancing the artificial joint during arthroplasty, measurement devices have been developed which help a surgeon measure some parameters during the balancing of the joint. The most common balancing devices are mechanical in nature: the surgeon manually applies force on the device to distract the bones of the joints and the distance between the bones is visually measured. Some measurement devices incorporate sensors which can be inserted into the artificial joint to provide measurements about load distribution that are useful when attempting to balance the joint. Even with these measurement devices, the surgeon is still required to manually apply an unknown or inaccurate force to the joint in order to determine whether the joint is balanced. If the amount of applied force is inconsistent with the actual force applied to the joint during actual use, the joint may not move appropriately and may wear prematurely, leading to limited movement, pain, and eventual replacement or further surgical repairs.

SUMMARY OF THE DISCLOSURE

Disclosed herein are devices and methods for balancing a joint during surgical procedures, such as prosthetic arthroplasty. In embodiments, the device is an insert with one or more plates, one or more sensors and at least one actuated mechanism for actuating the device against one or more parts of the joint. The one or more plates are disposed between bone structures which define the joint, such as the femur and the tibia in a knee joint. The one or more sensors provide force, position and angular data about the movement of the joint, which, along with the applied force data derived from the movement of the actuated mechanism, provide for highly accurate and dynamic adjustments of the joint. In one embodiment, at least one actuated mechanism is a spring-actuated mechanism. In another embodiment, at least one actuated mechanism is a pneumatic-actuated mechanism. A pressurizing apparatus is used to pressurize the pneumatic-actuated mechanism. Various types of actuation configurations, such as spring configurations and pneumatic configurations or a combination thereof, and sensors may be implemented in or on the insert to provide for control of the actuated mechanism and measurement of numerous parameters relating to the balancing of the joint. Customized graphical user interfaces (GUIs) are provided for real-time control and visualized feedback of adjustments. Sensor data may also be collected and compared with expected or preferred data sets to provide adjustment recommendations and achieve better outcomes based on historical data. Other features and advantages should become apparent from the following description of the preferred embodiments, taken in conjunction with the accompanying drawings.

In other embodiments, the device is a femoral balancer that is used to balance one or more femoral cuts, such as anterior, posterior, and distal cuts of the femur. The femoral balancer may be used to locate pins for making final balanced cuts to the femur or may include one or more blade guiding features to make the cuts directly while the femoral balancer is attached to the femur.

In some embodiments, the device is an insert for balancing a joint during repair of the joint. The insert includes a first plate, a second plate, and an actuator there between. The first plate is configured to interface with a bone structure of a joint. The second plate includes a plate portion, a transition portion, and a mounting portion. The plate portion is spaced apart from the first plate and is configured to interface with an opposing bone structure of the joint. The transition portion extends from the plate portion protruding beyond the perimeter of the first plate. The mounting portion extends in a transverse direction relative to the transition portion in the direction of the first plate. The actuator is configured to distribute a force to the first plate and to the plate portion. In embodiments, the insert includes a plurality of sensors for determining a spatial relationship between the first plate and the plate portion.

In some embodiments, the first plate is a bottom plate configured to contact a tibia during repair of the joint, and the second plate is a top plate where the plate portion is configured to contact a femur during repair of the joint and the mounting portion extends down beyond the bottom plate. In embodiments, the mounting portion further includes a body, a first leg, a second leg, a first mounting portion, and a second mounting portion. The body extends downward from the transition portion. The first leg extends downward from the body. The second leg extends downward from the body adjacent to the second leg forming an outer recess there between. The first mounting portion protrudes from the first leg. The second mounting portion protrudes from the second leg. In some embodiments, the first leg extends further than the second leg.

In other embodiments, the first plate is a top plate configured to contact a femur during repair of the joint, and the second plate is a bottom plate where the plate portion is configured to contact a tibia during repair of the joint and the mounting portion extends up beyond the top plate. In embodiments, the transition portion includes a first transition leg extending from the plate portion and a second transition leg extending from the plate portion. The mounting includes a first leg, a second leg, a first mounting portion, and a second mounting portion. The first leg extends upward from the first transition leg. The second leg extends upward from second transition leg and is joined to the first leg at the distal end of the bottom mounting portion. The first mounting portion protrudes from the first leg. The second mounting portion protrudes from the second leg.

In some embodiments, the actuator is a pneumatic actuator including a bellows made of an inflatable material and the bellows is configured to inflate and pneumatically distribute the force to the first plate and to the plate portion.

In embodiments, the second plate includes a mounting guide. The mounting guide includes a flange protruding from the mounting portion.

In some embodiments, the device is a joint balancing system for balancing the joint during repair of the joint. The joint balancing system includes any of the embodiments of the insert, such as the embodiments described above. The joint balancing system also includes a cutting guide and a mounting fastener. The cutting guide includes a guiding slot configured to guide a cut during the repair of the joint. The mounting fastener couples the cutting guide to the mounting portion with the mounting fastener extending into the flange. In embodiments, the mounting fastener is a guide pin and the insert includes an adjustment device affixed to the mounting portion configured to adjust a placement of the guide pin.

In embodiments, the joint balancing system includes a first bone angle sensor for affixing to the tibia during repair of the joint and an insert angle sensor coupled to the insert. In further embodiments, the joint balancing system further includes a second bone angle sensor for affixing to the femur during repair of the joint.

In some embodiments, the device is a distal femoral cutting guide. The distal femoral cutting guide includes a guide body, a blade guiding feature, and a guide rod. The guide body includes a bottom portion, a transition portion, and a front portion. In embodiments, the bottom portion includes a plate like shape and an insertion end. The transition portion extends from the bottom portion in a direction opposite the insertion end and curves towards a direction that is transverse to the direction opposite the insertion end. The front portion extends from the transition portion in the transverse direction. The blade guiding feature is a slot extending through the guide body and is configured to guide a distal femoral cut during a joint surgery. The guide rod extends from the bottom portion generally in the transverse direction.

In embodiments, the guide rod includes a base adjoining the bottom portion and an end distal to the bottom portion. The guide rod is narrower at the end than at the base and taps from the base to the end. In embodiments, the guide rod is formed in the shape of the intramedullary canal of the patient's femur. The shape of the guide rod is based off of measurements taken from an image of the joint of the patient. In embodiments, the guide rod extends in an initial direction that is less than ninety degrees relative to the plane of the bottom portion and curves towards extending in a direction that is closer to ninety degrees than the initial direction relative to the plane of the bottom portion.

In embodiments, the distal femoral cutting guide includes a cutting guide sensor and a bone angle sensor. The cutting guide sensor is affixed to the guide body and the bone angle sensor is configured to be affixed to the patient's femur while the guide rod is located in the intramedullary canal.

In embodiments, the distal femoral cutting guide includes an adjustment device affixed to the guide body. In embodiments, the adjustment device is affixed to the transition portion. The adjustment device is configured to adjust the position of the femoral cutting guide and to adjust the position of the blade guiding feature.

In embodiments, the front portion includes a top edge that is curved. In some embodiments, the top edge has an asymmetric curve with the apex shifted toward one side with the one side being higher than the other. In embodiments, the cutting guide sensor is affixed to the front portion adjacent to the apex of the top edge.

In some embodiments, the device is a distal femoral balancer for balancing the joint during repair of the joint. The distal femoral balancer includes a first condyle portion and a second condyle portion. The first condyle portion includes a first front portion, a first bottom portion, a first inner surface, and a first pin guide. The first front portion is configured to be located anterior to a first condyle of the joint. The first bottom portion extends from the first front portion. The first bottom portion is configured to be located inferior to the first condyle. The first inner surface is shaped to match a surface of the first condyle. The first pin guide is configured to receive a first pin and guide the first pin into the first condyle.

The second condyle portion includes a second front portion, a second bottom portion, a second inner surface, and a second pin guide. The second front portion is configured to be located anterior to a second condyle of the joint. The second bottom portion extends from the second front portion. The second bottom portion is configured to be located inferior to the second condyle. The second inner surface is shaped to match a surface of the second condyle. The second pin guide is configured to receive a second pin and guide the second pin into the second condyle.

In embodiments, the first pin guide includes a first bore extending through the first front portion and a first flange extending from the first bore, and the second pin guide includes a second bore extending through the second front portion and a second flange extending from the second bore. The first flange and the first bore are aligned, and the second flange and the second bore are aligned. In embodiments, the first flange and the first bore are coaxial, and the second flange and the second bore are coaxial.

In embodiments, the first condyle portion includes a first outer surface and the second condyle portion includes a second outer surface. The first outer surface and the second outer surface are configured to match the outer surface of the first condyle and the second condyle respectively.

In embodiments, the distal femoral balancer includes a balancer actuator located between the first bottom portion and the first condyle and the second bottom portion and the second condyle. In some embodiments, the balancer actuator is adjacent a distal femoral cut. In some embodiments, the balancer actuator includes a plurality of actuators.

In some embodiments, the device is a posterior femoral balancer for balancing the femur in flexion. The posterior femoral balancer includes a balancer body, a first posterior condyle portion, a second posterior condyle portion, a first posterior pin guide, and a second posterior pin guide. The balancer body is configured to be adjacent to the distal end of the femur. The first posterior condyle portion extends from the balancer body in a direction transverse to the balancer body. The second posterior condyle portion extends from the balancer body in the same direction as the first posterior condyle portion. The first posterior pin guide and the second posterior pin guide each include a flange extending outward from the balancer body and a bore extending through the balancer body. In embodiments, the flange is coaxial to the bore.

In embodiments, the balancer body includes a connection portion, a first leg, and a second leg. The connection portion joins the first leg and the second leg distal to the first posterior condyle portion and the second posterior condyle portion. The first posterior pin guide is located on the first leg and the second posterior pin guide is located on the second leg. In embodiments, the connection portion, the first leg, and the second leg form a 'U' shape.

In embodiments, the first leg includes a first rounded end distal to the first posterior condyle portion and the second leg includes a second rounded end distal to the second posterior condyle portion. In embodiments, the second rounded end protrudes further from the second posterior condyle portion than the first rounded end protrudes from the first posterior condyle portion. In embodiments, the first and second rounds protrude further than the connection portion forming an indent there between.

In embodiments, the first posterior condyle portion includes a first inner surface and the second posterior condyle portion includes a second inner surface. In embodiments, the posterior femoral balancer includes a balancer actuator adjoining the first inner surface and the second inner surface. The balancer actuator locates between the first and second posterior condyle portions and the condyles of the femur. In embodiments, the balancer actuator adjoins the posterior femoral cut. In embodiments, the balancer actuator includes a first actuator adjoining the first inner surface and a second actuator adjoining the second inner surface.

In embodiments, the first posterior condyle portion includes a first outer surface and the second posterior condyle portion includes a second outer surface. The first and second outer surfaces are shaped to resemble the posterior of a femoral condyle.

In some embodiments, the device is a whole femoral balancer for balancing the alignment of the entire femoral component simultaneously. The whole femoral balancer includes an anterior portion, a distal portion, a posterior portion, anterior pin guides, and distal pin guides. The anterior portion locates adjacent the anterior of the femoral component. The anterior portion includes an anterior edge. The anterior portion extends from the anterior edge in a first direction then transitions into a second direction that is transverse to the first direction. The distal portion extends in the second direction from the anterior portion and locates adjacent the distal end of the femoral component. The posterior portion extends from the distal portion. The posterior portion transitions from the second direction to a third direction that is opposite the first direction and extends in the third direction. The posterior portion locates adjacent the posterior of the femoral component. The anterior pin guides are located at the anterior portion. The anterior pin guides are configured to guide pins into the anterior of the femoral component. The distal pin guides are located at the distal portion. The distal pin guides are configured to guide pins into the posterior of the femoral component.

In embodiments, the anterior pin guides each include an anterior bore extending through the anterior portion and an anterior flange extending from the anterior portion and aligned with the anterior bore. The distal pin guides each include a distal bore extending through the distal portion and a distal flange extending from the distal portion and aligned with the distal bore. In embodiments, the anterior bore and the anterior flange are coaxial, and the distal bore and the distal flange are coaxial.

In embodiments, the anterior portion includes an anterior outer surface. The anterior outer surface includes rounds to form the general shape of the anterior of the femoral component. The distal portion includes a distal outer surface. The distal outer surface includes rounds to form the general shape of the distal end of the femoral component. The posterior portion includes a posterior outer surface that includes rounds to form the general shape of the posterior of the femoral component.

In embodiments, the anterior portion includes an anterior inner surface extending in the first direction. The distal portion includes a distal inner surface extending perpendicular to the anterior inner surface. The posterior portion includes a posterior inner surface extending parallel to the anterior inner surface. In embodiments, the anterior inner surface, the distal inner surface, and the posterior inner surface are flat surfaces. In embodiments, the anterior portion includes an anterior chamfer surface extending between the anterior inner surface and the distal inner surface. The posterior portion includes a posterior chamfer surface extending between the distal inner surface and the posterior inner surface. In embodiments, the anterior chamfer surface extends at a forty-five degree angle relative to the anterior inner surface and the distal inner surface. The posterior chamfer surface extends at a forty-five degree angle relative to the distal inner surface and the posterior inner surface.

In embodiments, the distal portion includes a first distal leg and a second distal leg, each following the shape of a condyle of the femoral component. The posterior portion includes a posterior first condyle portion and a posterior second condyle portion. The posterior first condyle portion extends from the first distal leg, and the posterior second condyle portion extends from the second distal leg. In some embodiments, the first distal leg and the second distal leg each extending from the anterior portion. In embodiments, a distal pin guide is located at each of the distal legs.

In some embodiments, the whole femoral balancer includes actuators for balancing the femoral component. In embodiments, the actuators include an anterior actuator adjoining the anterior inner surface, a distal actuator adjoining the distal inner surface, and a posterior actuator adjoining the posterior inner surface. In embodiments, the anterior actuator is located between the anterior inner surface and an anterior cut. The distal actuator is located between the distal inner surface and a distal cut. The posterior actuator is located between the posterior inner surface and a posterior cut. In embodiments, the anterior actuator includes multiple actuators. The distal actuator includes multiple actuators, such as one adjacent each distal leg. The posterior actuator includes multiple actuators, such as one adjacent each posterior condyle portion.

In embodiments, the whole femoral balancer includes an anterior adjustment device located at the anterior portion for adjusting the anterior portion relative to the femoral component and a distal adjustment device for adjusting the distal portion and the posterior portion relative to the femoral component.

In embodiments, the anterior portion includes an end portion and a middle portion. The middle portion forms the transition between the end portion and the distal portion. The whole femoral balancer includes relief slots extending inward from the side edges. In embodiments, two anterior relief slots extend inward between the end portion and the middle portion and two distal relief slots extend inward between the middle portion and the distal portion.

In embodiments, the whole femoral balancer includes an anterior sensor affixed to the anterior portion and a distal sensor affixed to the distal portion. In some embodiments, the whole femoral balancer also includes a bone angle sensor that affixes to the femur.

Methods for performing cuts to bones and balancing joints is also disclosed herein. In embodiments, the method includes inserting the insert into the joint. In some embodiments, the joint is the knee. The method also includes deploying the actuators. In some embodiments, deploying the actuators includes inflating the bellows. The method further includes drilling a hole or holes into the bone. In embodiments, the holes are located in the femur or tibia. In embodiments, the pin guides or mounting guides are used to guide the drill. The method yet further includes placing a pin into each hole(s) in the bone. In embodiments, the pin guides or mounting guides are used to guide the pin(s) into the bone. The method still further includes mounting the cutting guide onto the pins. In embodiments, the cutting guide is mounted adjacent the pin guides or the mounting portion of the insert. The method further includes cutting the bone using the guiding slot to guide the cut. In embodiments, the cut is made parallel to the plate opposite the bone, at a fixed distance from the plate or at a predetermined angle relative to the plate. For example, the cut may be made parallel to the bottom plate, at a fixed distance from the bottom plate, or at a predetermined angle relative to the bottom plate 150. In other embodiments the cut may be made parallel to the top plate, at a fixed distance from the top plate, or at a predetermined angle relative to the top plate.

In embodiments, the method also includes adjusting the angle and/or location of the pin guides or the mounting guides. In embodiments, adjusting the angle and/or location of the pin guides or the mounting guides includes manually adjusting or actuating the adjustment device. In embodiments, adjusting the angle and or location of the pin guides or the mounting guides is performed prior to cutting the bone.

A method for performing a femoral cut using the femoral cutting guide 500 is also disclosed. In embodiments, the method includes inserting the guide rod into the intramedullary canal of the femur. In embodiments, the guide rod is inserted so that the guide rod is aligned with the long axis of the femoral shaft. The method also includes cutting the bone at a fixed angle relative to the guide rod.

In embodiments, the method includes affixing a bone angle sensor to the femur. And measuring the angle between the cutting guide sensor affixed to the femoral cutting guide and the bone angle sensor. In embodiments, the method further includes adjusting the angle and position of the blade guiding feature. In some embodiments, adjusting the angle and position of the blade guiding feature relative to the femur includes manually adjusting or actuating the adjustment device until the blade guide feature is at the predetermined angle for the cut.

In embodiments, the device is a distal femoral balancer used to balance the joint. In embodiments, the method includes making a distal femoral cut. Any of the cutting methods and tools described herein may be used to make the cut. In some embodiments, the method includes removing the insert after making the cut. The method also includes placing the distal femoral balancer on the distal femoral cut and deploying the distal femoral balancer to distract the joint. In embodiments, placing the distal femoral balancer includes locating the distal femoral balancer as shown in the figures and as described herein. The method further includes forming holes into the bone and placing pins into the holes. In some embodiments, the bone is a femur. In embodiments, the pin guides are used to make the holes and to place the pins. In embodiments, placing the pins includes locating the pins at a fixed distance and at a fixed angle from the bottom portion of the distracted device. In embodiments, the method includes mounting a cutting block to the pins and using the guiding slot to make a second cut to the bone.

In some embodiments, the device is a posterior femoral balancer used to balance the joint. In embodiments, the method includes making a posterior femoral cut. Any of the cutting methods and tools described herein may be used to make the cut. In some embodiments, the method includes removing the insert after making the cut. The method also includes placing the posterior femoral balancer on the posterior femoral cut and deploying the posterior femoral cut to distract the joint. In embodiments, placing the posterior femoral balancer includes locating the posterior balancer as shown in the figures and as described herein. The method further includes forming holes into the bone and placing pins into the holes. In embodiments the bone is a femur. The pin guides 740 may be used to make the holes and to place the pins. In embodiments, placing the pins includes locating the pins at a fixed distance and at a fixed angle from the bottom portion of the distracted device. In embodiments, the method also includes mounting a cutting block to the pins and using the guiding slot to make a second cut to the bone.

In some embodiments the device is a whole femoral balancer used to balance the joint. In embodiments, the method includes placing the whole femoral balancer over the femoral component. In embodiments, placing the whole femoral balancer includes locating the whole femoral balancer as shown in the figures and described herein. The method also includes cutting the bone. In embodiments, cutting the bone includes performing anterior, distal and/or posterior cuts to the femoral component. The cuts may be made before or after placing the whole femoral balancer over the femoral component. The method also includes deploying the whole femoral balancer to distract the joint.

The method may also include forming holes into the bone and placing pins into the holes. In embodiments, the bone is a femur. In embodiments, the pin guides are used to make the holes and to place the pins. One or more sets of holes are formed and one or more sets of pins are placed in the holes. In embodiments, placing the pins includes locating the pins at a fixed distance and at a fixed angle from a predetermined portion of the distracted device. The method may also include mounting a cutting block to the pins or to one set of pins and using the guiding slot to make a cut to the bone. In embodiments, the method includes mounting a second cutting block to another set of pins and making another cut to the bone.

In some embodiments, the method includes adjusting the relative angle and position of all or a portion of the whole femoral balancer, such as the anterior portion or the distal portion. In embodiments, adjusting the relative angle and position of all or a portion of the whole femoral balancer may include manually adjusting or actuating the anterior adjustment device and/or the distal adjustment device. In some embodiments, the method also includes measuring the angle of all or a portion of the whole femoral balancer relative to the bone, such as the femur 8. In embodiments, measuring the angle of all or a portion of the whole femoral balancer relative to the bone may include measuring the relative angle between the anterior sensor and the bone sensor and measuring the relative angle between the distal sensor and the bone sensor. Other sensors, such as a sensor located on the posterior portion may also be used. In embodiments, the method includes affixing a bone sensor to the bone. The step of adjusting the relative angle and position of the whole femoral balancer may be performed prior to making the cuts.

BRIEF DESCRIPTION OF THE DRAWINGS

Various embodiments disclosed herein are described in detail with reference to the following figures. The drawings are provided for purposes of illustration only and merely depict typical or exemplary embodiments. These drawings are provided to facilitate the reader's understanding and shall not be considered limiting of the breadth, scope, or applicability of the embodiments. It should be noted that for clarity and ease of illustration these drawings are not necessarily made to scale.

The various embodiments mentioned above are described in further detail with reference to the aforementioned figured and the following detailed description of exemplary embodiments.

DETAILED DESCRIPTION

Figure 1:
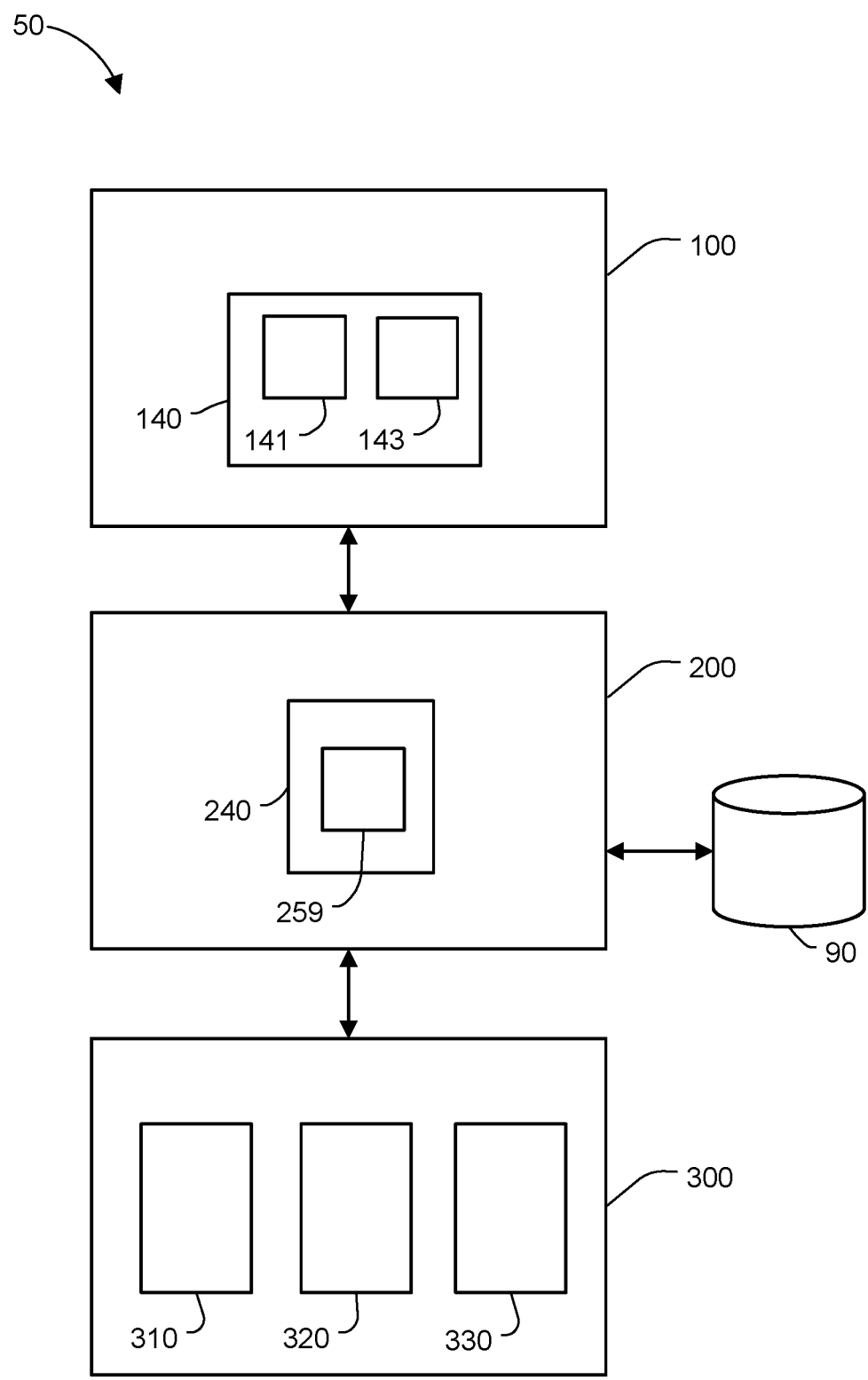
FIG. 1 is a functional block diagram of a joint balancing system, according to one embodiment of the invention.

Disclosed herein are systems, devices, and methods for balancing a joint during surgical procedures on joints, such as prosthetic arthroplasty. FIG. 1 is a functional block diagram of a joint balancing system 50, according to one embodiment of the invention. Joint balancing system 50 may include a trial insert ("insert") 100, a controller assembly 200, and a display system 300. The joint balancing system 50 includes an insert 100 with one or more plates, one or more sensors and at least one actuator/actuated mechanism for actuating the device against one or more parts of the joint as illustrated in FIGS. 2-11. The actuated mechanism may be fluid powered, such as by air, electromechanical, electromagnetic, mechanical, piezoelectric, or a combination thereof. Other actuated mechanisms may also be used. The one or more plates are disposed between bone structures which define the joint, such as the femur and the tibia in a knee joint. The one or more sensors may provide force, position and angular data about the movement of the joint, which, along with the applied force data from the actuation mechanism, provide for highly accurate and dynamic adjustments of the joint. Various configurations of the actuators and sensors may be implemented in or on the insert 100 to provide for control of the insert 100 and measurement of numerous parameters relating to the balancing of the joint. The addition of an actuated mechanism to the inserts provides numerous benefits to the process of balancing a joint during surgical procedures, such as arthroplasty. The surgeon is able to apply a known and controlled amount of force to the joint and correlate the measured load, movement and angular data with the applied force to more precisely determine if adjustments should be made. The actuated mechanism may also be capable of dynamic actuation from a variety of different actuation points on the insert, providing the ability to apply different load amounts, different amounts of movement and different angles of movement to more accurately simulate the movement of the joint and measure the results. The load can be measured across any range of motion to provide significant improvements in load balancing.

The insert 100 may include an electronics board 140. The electronics board 140 may include a board module 141 and a board communication module 143. The board module 141 may be configured to obtain the data from the sensors and send the data to the controller assembly 200 via the board communication module 143. The board module 141 may also be configured to relay a signal from the controller assembly 200 to the actuators. The board module 141 may also be configured with a safety override to control the actuator force or the magnitude of distraction or displacement. The board module 141 may further be configured to communicate a signal when the insert 100 is unbalanced and communicate another signal when the insert is balanced. The signal may cause an alert, such as an auditory alert or a visual alert provided by electronic hardware attached to the electronics board 140 and/or from the display system. The auditory alert may be provided by a sound source, such as a speaker or a piezoelectric sound generator. The visual alert may be provided by a light source, such as a light emitting diode. The board module 141 may yet further be configured to provide guidance for alignment during surgery to surgical instruments, such as drills and saws. The communications module 143 may be configured to send/receive electronic signals to/from the controller assembly over a wired or wireless connection. In some embodiments, the communications module 143 is configured to communicate with other surgical instruments such as drills and saws.

The controller assembly 200 may be used to manually or remotely control the actuators within the insert 100. In some embodiments, the controller assembly 200 physically or mechanically controls the actuators which may allow for manual manipulation of the movement of the actuators by a surgeon or medical technician. In other embodiments, the controller assembly 200 electronically controls the actuators which can be monitored and programmed as a computing device with a processor and memory.

Controller assembly 200 may include a controller 240. Controller 240 may include a controller communication module 259. The controller communication module 259 is configured to send/receive signals from the insert 100 and from the display system 300 over a wired and/or a wireless connection. In some embodiments, the controller communication module 259 is configured to communicate with other surgical instruments, such as drills and saws. The controller communication module 259 may relay the guidance provided by the board module 141 to the surgical instruments.

Controller assembly 200 may be manipulated through one or more input devices, such as a mouse, a keyboard, capacitive buttons, or an interactive display. The interactive display may be part of the display system 300 and may display the controls for each actuator along with the relevant values and other measured parameters for easy comparison during joint balancing. A single controller 240 may be configured to apply the same pressure to all of the actuators. This may simplify the design and ensure that an equal force/pressure is applied at each actuator.

Display system 300 may be a computing device with a processor and memory, such as a computer, tablet, smartphone, or other electronic device that may be used to display the GUI. Display system 300 may include a display communication module 310, a display module 320, and a display 330, such as a monitor. Display communication module 310 is configured to send/receive wired or wireless communications to/from the controller assembly 200.

Display module 320 may provide customized graphical user interfaces (GUIs) for viewing on display 330. The GUIs may display relevant data for real-time control and visualized feedback of adjustments through visual alignment guides that indicate when all of the measured parameters are within preferred ranges. The GUIs may also present the values for the parameters measured by the various sensors.

Sensor data may also be collected and compared with expected or preferred data sets to provide adjustment recommendations and achieve better outcomes based on historical data. A GUI may provide visual or audio indications as to whether the joint is balanced by comparing the measured parameters with known accepted ranges of the values. In embodiments, the GUI may provide the force applied to the top plate 110 and the bottom plate 150. The force may be determined using the height and pressure measurements provided by the sensors. The force may be determined by the display system 300, such as by the display module 320, or by another system/module.

Joint balancing system may also include a data store 90. The data store 90 may be a separate system connected to either the display system 300 or the controller assembly 200, or may be located within either the display system 300 or the controller assembly 200. In embodiments, the data in the data store 90 may be uploaded to a central server for analysis.

In one embodiment, a visual alignment guide may be presented which graphically illustrates the alignment of the two plates and the movement of the actuators within the joint in real-time. The visual alignment guide may provide guide lines or circular targets that will help the surgeon achieve a desired alignment. The alignment guide may also provide color-coded visual graphics to indicate whether an alignment is good (green) or bad (red).

In some embodiments, the GUI displays one or more diagrams related to the positioning of the insert 100. The diagrams may display the relative displacement between the top and bottom plates in one or more of the sensor locations. The GUI may also display the tilt between the top and bottom plates. The GUI may include multiple graphs. One graph may display the history of the tilt in the mediolateral (side to side) direction. Another graph may display the tilt in the anteroposterior direction. The GUI may also display the knee flexion angle, pressure, force, and battery voltage. The GUI may also provide buttons to save the data or to generate a screen capture for future reference. This data and information may be archived in the data store 90. A third graph may display the history of the distance between the top and bottom plates. The GUI may also display previously recorded data against which the real time data can be compared.

In some embodiments, the GUI displays three diagrams. One diagram displays the data collected while the knee is at 0 flexion, another diagram displays the data collected while the knee is at 90 degrees flexion, and the third diagram displays the data in real time.

In some embodiments, the GUI can be used prior to surgery to set up a custom or patient-specific balance that is unique to the patent and/or the insert 100. The GUI can also contain a list of instructions as to where the problem is within the joint and can provide a recommendation to the surgeon on how to correct the problem. The GUI can also display information from other devices or instruments, such as computer navigation systems, surgical robots, instruments, such as drills and saws, tourniquet sensors, etc.

Figure 2:
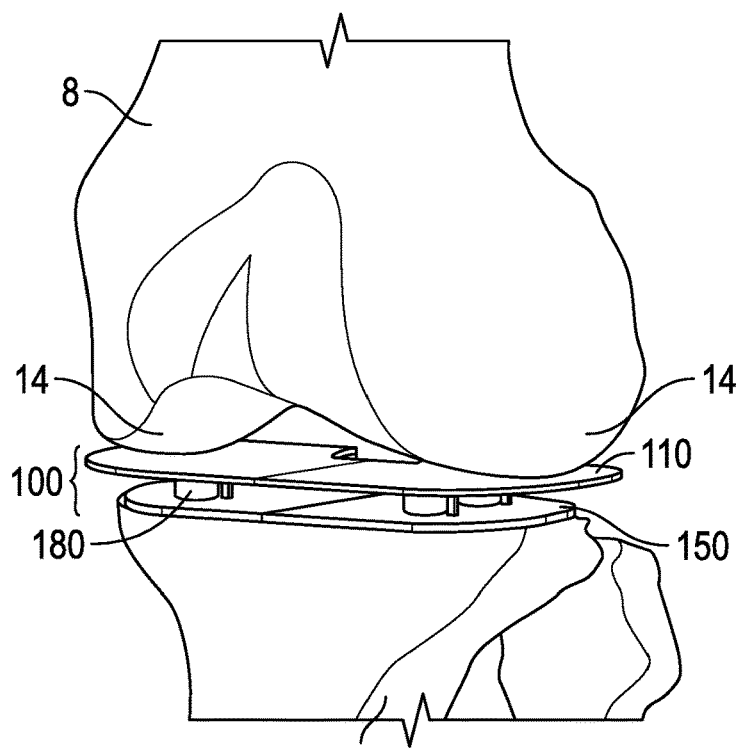
FIG. 2 is an illustration of an embodiment of the insert of FIG. 1 disposed in a knee joint.

FIG. 2 is an illustration of an embodiment of the insert 100 of FIG. 1 disposed in a knee joint. In the embodiment illustrated, the insert 100 includes a top plate 110 and a bottom plate 150 separated by actuators 180 positioned at various points on the interior surfaces of the top plate 110 and bottom plate 150. The top plate 110 is disposed against a femur 8, while the bottom plate 150 is disposed against a tibia 10. The insert 100 is additionally configured with one or more sensors (shown in FIG. 3) disposed along the top plate 110 and/or the bottom plates 150. The sensors are configured to measure and determine various parameters related to the balancing of the joint, as described herein.

The insert 100 may be designed as a temporary insert that is positioned into the joint only during a joint balancing procedure, such that it is replaced by a permanent insert of similar shape and size once the joint balancing is complete. In another embodiment, the insert 100 may be permanent, such that it will remain in position between the adjacent bones once the joint has been balanced.

The insert 100 may be a standalone device before insertion into the joint. The top plate 110 and bottom plate 150 may vary in shape and size and be aligned in parallel planes. The general shape of the top plate 110 and corresponding bottom plate 150 (is designed to fit within the knee joint and provide a large surface area to interface with, such as contacting, the bony surfaces of the adjacent femur 8 and tibia 10. In the embodiment illustrated, insert 100 includes four total actuators 180 (three visible) disposed between the top plate 110 and the bottom plate 150. The actuators 180 may be evenly spaced and positioned within different quadrants of the insert 100 to provide for actuation from different points within the insert that will allow for dynamic load balancing at each actuator and different angles of actuation of the insert 100. For example, if two adjacent actuators 180 are actuated, the insert may be disposed at an angle which slopes from one side of the insert 100 to the other. The number of actuators 180 may vary and may be as few as one. The actuators 180 may be placed in other configurations, such as triangular, circular, or irregular placements. The actuators may also be tilted or angled to generate shear or rotational forces (torque).

A method of balancing a joint using the insert 100 in accordance with one embodiment of the invention will now be described. The balance of the joint may be measured at several stages of the surgical procedure. For example: measurements may be taken before making any bone cuts, or after making the tibial bone cut against the uncut femoral surface, or after making the femoral cut against the cut femoral surfaces or against a trial femoral prosthesis, or with trial femoral or tibial prostheses in place, or with the final femoral and tibial prostheses in place. During a first step, the insert is positioned in a gap or opening of a joint between two opposing bone structures, such as an opening between a femur 8 and a tibia 10 in a knee joint. In some embodiments, insertion/extraction tools are used to insert the insert 100 into the opening. Next, one or more of the actuators 180 is activated to apply a load to the bone structures of the femur 8 and tibia 10. The sensors measure one or more parameters relating to the joint, such as the movement, pressure, angle, position, range of motion, gap, load applied by each actuator, etc. The measurements may provide an indication as to whether the joint is balanced—i.e. whether pressure is being evenly applied to the insert by the opposing bone structures, whether the joint is able to move within a desired range of motion, the magnitude of the gap between the surfaces of the femur 8 and tibia 10 and the change in gap when the knee is flexed or extended, whether the ligaments surrounding the joint are under too much tension, etc. The measurements may also indicate that the bone cuts are not optimum, for example, the tibia 10 may have been cut in too much varus or valgus, the femur 8 may have been cut in too much varus or valgus, or in external or internal rotation, or the distal cut of the femur may have been made too deep resulting in a mismatch of the gap between the surfaces of the femur and tibia at different flexion angles. If the measurements and analysis of the measurements indicates that the joint is not properly balanced or the bone cuts are not appropriate, the surgeon will make one or more adjustments to some portion of the joint to improve the balance of the joint. The adjustments may include: re-cutting the bones, releasing or tightening ligaments, adjusting the placement or rotation of the prosthetics or the insert 100; cutting away portions of the bones, ligaments or cartilage; or increasing or decreasing the height of the insert 100 to better fit the gap in the joint. The joint may be tested again by actuating one or more of the actuators and measuring the parameters to determine if improvements have been made. This process may be repeated till the surgeon is satisfied with the measurements. In embodiments including a fluid powered actuator, measuring the distraction while changing the pressure of the fluid powered actuator may be used to characterize the biomechanical properties of the soft tissues and aid in selecting the optimal balance.

At the point where the measurements fall within certain acceptable ranges, the joint is considered to be balanced. If the insert 100 is designed to function as a permanent prosthetic, it is left in place in the joint opening. If the insert 100 is configured only as a measurement and testing tool, it is removed and then replaced with a permanent prosthesis of identical dimensions. In some embodiments, the data collected by the sensor(s) are used to generate a custom implant on demand.

Further details of the properties and function of the insert 100 will be described below with regard to the actuators, sensors, shape and configuration of the device, controllers and user interface and additional tools for joint balancing.

Sensors

Sensors disposed on or within the insert 100 can be configured to measure and be used to determine numerous different parameters related to the balancing of the joint. For example, the sensors can be configured to measure and be used to determine the force, or load, being applied by the actuators and the resulting pressure received on various sections of the top or bottom plates by the adjacent bone. Examples of these sensors are load cells, strain gages, pressure sensors, etc. For spring actuators, the spring force may be calculated indirectly, for example using the known spring stiffness and the measured spring length using displacement sensors. Sensors can also be configured to monitor distance of movement, either total movement between the top and bottom plates or movement of each individual actuator. Examples of these sensors are magnetic sensors, optoelectric sensors, and monitoring the stroke of the actuator mechanism (e.g. screw driven actuators). Sensors may also measure angles of motion, and even angular positions through the use of accelerometers, magnetometer, and gyroscopes.

The inserts 100 may incorporate a plurality of different sensors in order to measure different types of parameters or to measure the same types of parameters at different places on the insert 100. The sensors communicate via a wired or wireless connection, and may be powered by an external power source or an internal power source within each sensor or a power source located within the insert 100.

Figure 3:
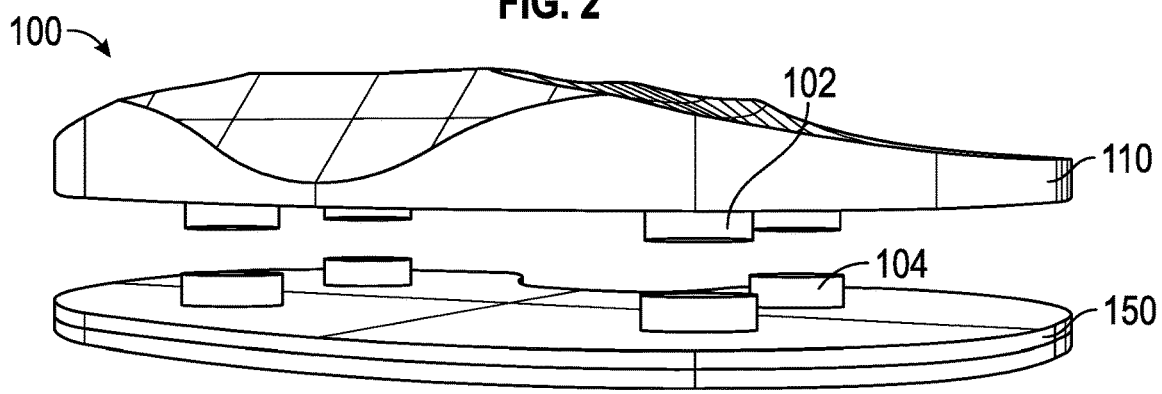
FIG. 3 is a perspective view illustration of an embodiment of the insert of FIG. 1 with displacement sensors.

FIG. 3 is a perspective view illustration of an embodiment of the insert 100 of FIG. 1 with sensors 102. The actuators 180 are not shown for clarity. Sensors 102 may be used to determine the relationship between the top plate 110 and the bottom plate 150, such as the spatial relationship, including the distance and angle between the top plate 110 and bottom plate 150, and the pressure between the top plate 110 and the bottom plate 150. In the embodiment illustrated, sensors 102 are displacement sensors with corresponding magnets 104. The sensors 102 and magnets 104 may be located on opposite interior surfaces of the top plate 110 and the bottom plate 150. Insert 100 may include any number and configuration of sensors 102 and magnets 104. In the embodiment illustrated, the insert 100 has four sensors 102 on an interior surface of the bottom plate 150 and four corresponding magnets 104 configured on an interior surface of the top plate 110 for holding the two plates together. The sensors 118 measure displacement between the top plate 110 and bottom plate 150 at multiple locations and calculate tilt in two directions. The sensors 102 may be Hall Effect sensors. The sensors 102 and magnets 104 may be aligned between the top plate 110 and the bottom plate 150.

In some embodiments, a single sensor 102 is positioned in a center area of the insert 100, such that the top plate 110 and bottom plate 150 pivot around the sensor 102 and the corresponding magnet 104. The single sensor 102 is therefore able to measure displacement between the top plate 110 and the bottom plate 150, as well as rotational movement in three directions. In one embodiment, the single sensor 102 is a three dimensional magnetometer.

In some embodiments, the sensor 102 is a pressure sensor. In these embodiments, the sensor 102 may cover a substantial portion of a surface of the top plate 110 or bottom plate 150 and may adjoin that surface. In these embodiments, the pressure sensors may be configured such that a pressure map can be determined and provided by the GUI including the relative position of femoral condyles during the balancing of a knee. In one embodiment, the sensor is positioned above a substantial portion of an interior surface of the bottom plate 150. In another embodiment, the sensor 102 is positioned on an exterior surface of the bottom plate 150. In yet another embodiment, the sensor 102 is positioned on an interior surface of the top plate 110. In a further embodiment, the sensor 102 is positioned on the articular exterior surface of the top plate 110. The sensor 102 is capable of measuring pressure distribution over the entire surface area of the adjoining surface and may be configured to measure contact pressure between the femur 8 and tibia 10.

Additionally, one or more of the sensors 102 may be angle measurement sensors (including accelerometers, magnetometers and gyroscopes) that are configured to measure the angle of the insert relative to the leg, thigh, or any other part of the body, as well as relative to the ground. This information can be used to determine whether there is an imbalance in the joint and to assess if the imbalance is due to ligament imbalance or improper bone cuts.

Pneumatic-Actuated Mechanisms

Figure 4:
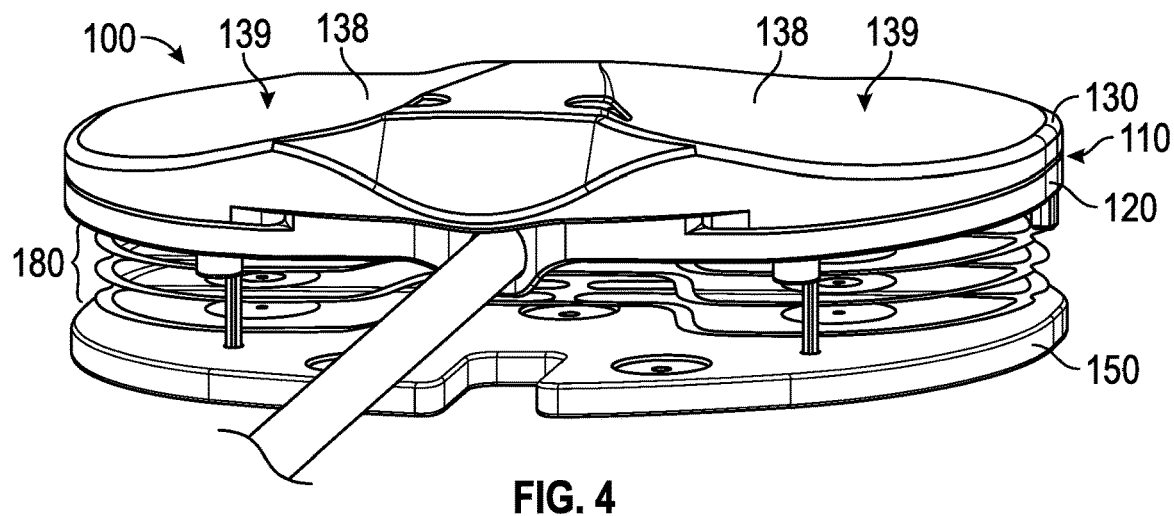
FIG. 4 is an illustration of a perspective view of an embodiment of the insert of FIG. 1 with a pneumatic actuator.

In some embodiments, the insert 100 may be actuated by fluid power, such as by pneumatics or hydraulics. Fluids such as air, saline, or more viscous fluids, such as gels, may be used to as the actuating fluid. FIGS. 4-7 illustrate an embodiment of the insert 100, where the insert 100 is a pneumatic insert. FIG. 4 is an illustration of a perspective view of an embodiment of the insert of FIG. 1 with a pneumatic actuator 180.

In the embodiment illustrated, top plate 110 includes a plate portion 120 and an articular portion 130. The articular portion 130 attaches to plate portion 120 and is configured to interface with, such as by direct or indirect contact, the natural or artificial femur. The top plate 110 or bottom plate 150 may include one or more grooves 138. The grooves may be oval shaped to match the natural shape of the condyles of the adjacent bone. In the embodiment illustrated, grooves 138 are located on the outer surface of the top plate 110 with a groove 138 on each side of the top plate 110 which would receive corresponding condyles 14 (see FIG. 2) of the femur 8.

The grooves 138 may include an articular contact surface 139 that articulates with the articular surface of the natural or artificial femur. In the embodiment illustrated, the grooves 138 and articular contact surface 139 are located on an outer surface of the articular portion 130, located opposite both the top portion 120 and the bottom plate 150. The articular portion 130, including the grooves 138 and the articular contact surfaces 139, can be shaped to accommodate any femoral articular size or shape.

Figure 5:
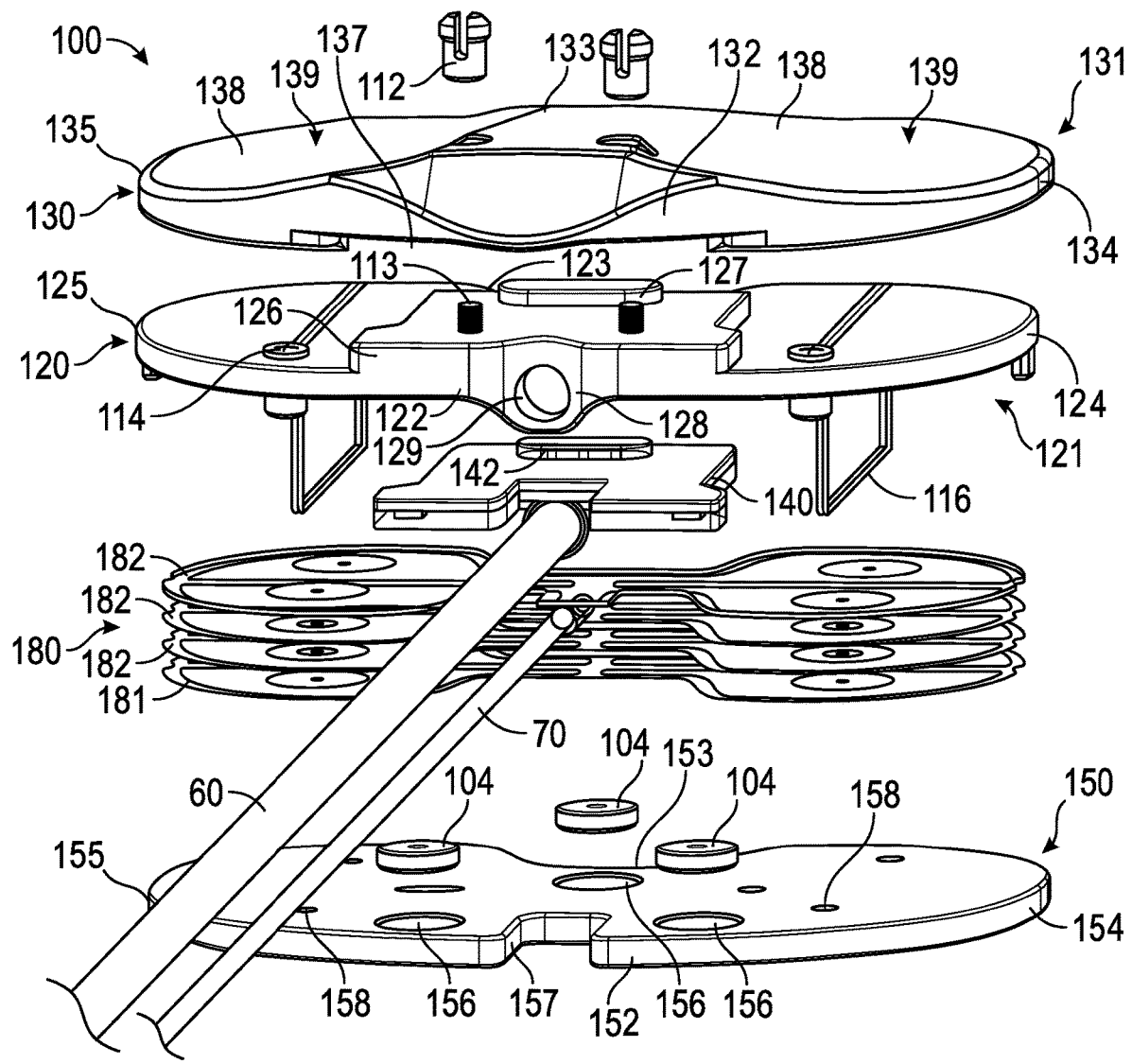
FIG. 5 is an illustration of an exploded view of the insert of FIG. 4.

FIG. 5 is an illustration of an exploded view of the insert 100 of FIG. 4. The actuator 180 is located between the top plate 110 and the bottom plate 150. The top plate 110 and the bottom plate 150 may be combined to or may individually match the natural shape of the tibial bone or match the shape of an implant, such as a tibial tray. A pneumatic actuator 180 may be formed of one or more bellows. The actuator may include multiple configurations of bellows, such as first bellows 181 and second bellows 182. In the embodiment illustrated, the actuator 180 includes four layers of bellows with one first bellows 181 and three second bellows 182. In embodiments, the first bellows 181 and the second bellows 182 are stacked between the top plate 110 and the bottom plate 150. The actuator 180 is connected and fluidly coupled to a fluid supply line 70. The fluid supply line 70 allows the fluid, such as air, to be added or removed from the one or more bellows to position the top plate 110 relative to the bottom plate 150.

Plate portion 120 may include a plate body 121, a board receiving feature 124, a connection feature 128, and a connection hole 129. Plate body 121 may include a plate body connection end 122, a plate body insertion end 123, a plate body first side 124, and a plate body second side 125. Plate body connection end 122 may generally have a convex shape. The curvature of the convex shape may be similar to the curvature of the flatter portion of an ellipse. Plate body insertion end 123 is opposite plate body connection end 122. Plate body insertion end 123 may include a concave portion and may generally have the shape of a portion of a Cassini oval that is between an oval and a lemniscate. Plate body first side 124 and plate body second side 125 may be symmetrical and may each have a circular shape. Plate body connection end 122, plate body insertion end 123, plate body first side 124, and plate body second side 125 may form the perimeter of plate portion 120.

Board receiving feature 126 may protrude from plate body 121 towards articular portion 130 and away from bottom plate 150. Board receiving feature 126 may generally include a T-shape. Board receiving feature 126 may also include a cavity for receiving electronics board 140. Board receiving feature 126 may further include one or more electronics receiving features 127. The electronics receiving features 127 may be a protrusion or a recess configured to receive electronic hardware 142 coupled to electronics board 140.

Connection feature 128 may extend from plate portion 120 at plate body connection end 122 generally towards bottom plate 150. Connection feature 128 may extend in the opposite direction relative to board receiving feature 124. Connection hole 129 may extend through connection feature 128 to provide access to electronics board 140.

Articular portion 130 may include an articular portion body 131, a recess 137, and a connection end bevel 136 along with the grooves 138 and the articular surfaces 138. Articular portion body 131 may generally include the same shape about its perimeter as plate body 121. Articular portion body 131 may include an articular portion body connection end 132, an articular portion body insertion end 133, an articular portion body first side 134, and an articular portion body second side 135. Articular portion body connection end 132 may generally have a convex shape. The curvature of the convex shape may be similar to the curvature of the flatter portion of an ellipse. Articular portion body insertion end 133 is opposite articular portion body connection end 132. Articular portion body insertion end 133 may include a concave portion and may generally have the shape of a portion of a Cassini oval that is between an oval and a lemniscate. Articular portion body first side 134 and articular portion body second side 135 may be symmetrical and may each have a circular shape. Articular portion body connection end 132, articular portion body insertion end 133, articular portion body first side 134, and articular portion body second side 135 may form the perimeter of articular portion 130.

Recess 137 may be located opposite grooves 138 and articular surfaces 139. Recess 137 may include a T-shape and may be configured to receive board receiving feature 126. Connection end bevel 136 may be located at connection end 132 and may be centered in connection end 132 between to grooves 138.

The insert 100 may include attachment mechanisms 112. Attachment mechanisms 112 may be fasteners, such as detent posts. The articular portion 130 may be attached to the top portion 120 using the attachment mechanisms 112. Screws 113 may extend through and up from board receiving feature 126. Attachment mechanisms 112 may be configured to couple to screws 113 to hold plate portion 120 to articular portion 130.

The bottom plate 150 may include a bottom plate body 151, one or more magnet recesses 156, a connector recess 157, and restraining holes 158. The bottom plate body 151 may generally include the same shape about its perimeter as plate portion body 121 and articular body portion 131.

Bottom plate body 151 may include bottom plate body connection end 152, a bottom plate body insertion end 153, a bottom plate body first side 154, and a bottom plate body second side 155. Bottom plate body connection end 152 may generally have a convex shape. The curvature of the convex shape may be similar to the curvature of the flatter portion of an ellipse. Bottom plate body insertion end 153 is opposite bottom plate body connection end 152. Bottom plate body insertion end 153 may include a concave portion and may generally have the shape of a portion of a Cassini oval that is between an oval and a lemniscate. Bottom plate body first side 154 and bottom plate body second side 155 may be symmetrical and may each have a circular shape. Bottom plate body connection end 152, bottom plate body insertion end 153, bottom plate body first side 154, and bottom plate body second side 155 may form the perimeter of bottom plate body 151.

Each magnet recess 156 may extend into bottom plate body 151 from an interior surface of bottom plate body 151 and may be configured to hold one or more magnet 104. In the embodiment illustrated, insert 100 includes one magnet in each magnet recess 156. Each magnet recess 156 may be adjacent actuator 180. The embodiment illustrated includes three magnet recesses 156 arranged in a triangular pattern. In other embodiments, different numbers of magnetic recesses 156 and magnets 104 are used and arranged in different patterns. Each magnet recess 156 and the magnet 104 therein may be aligned with a sensor 102.

Connector recess 157 may extend into bottom plate body 151 from bottom plate body connection end 152. In the embodiment illustrated, connector recess 157 is a cuboid shaped recess. Connector recess 157 is configured so that bottom plate 150 does not interfere with connector feature 128 when actuator 180 is in its narrowest configuration, such as when the bellows 182 are empty.

Restraining holes 158 may be used to secure bottom plate 150 to top plate 110. The insert 100 may include a restraining device 115. The restraining device 115 is configured to hold the top plate 110 and the bottom plate 150 together. The restraining device 115 is also configured to prevent the top plate 110 and the bottom plate 150 from separating beyond a desired distance and is configured to allow the actuator 180 to expand up to a predetermined amount. In the embodiment illustrated, the predetermined amount of expansion is 6 millimeters, which may allow the insert 100 to expand from eight millimeters to fourteen millimeters. In the embodiment illustrated, the restraining device 115 is made of medical suture material. In other embodiments, the restraining device 115 is integral to each chamber of the pneumatic actuator 180. In other embodiments, the restraining device 115 is a skirt around the perimeter extending between the top plate 110 and the bottom plate 150. Some embodiments may be configured to expand beyond fourteen millimeters. Other embodiments are configured shims are added to the bottom plate 150 to increase the distraction. In yet other embodiments, an articular portion 130 with an increased thickness is attached to the top plate 110 to further expand the height of the insert 100 beyond fourteen millimeters.

In the embodiment illustrated, the insert 100 includes two restraining devices 115, one on each side of the insert 100. The restraining device 115 may contact the outer surface of the bottom plate 150, pass through the restraining holes 152 and be affixed to the top plate 110. In the embodiment illustrated, each restraining device 115 is affixed to the top portion 120 with retaining fasteners 124, such as screws.

The insert 100 may also include an electronics board 140. The electronics board 140 may be housed within the top plate 110 or the bottom plate 150. In the embodiment illustrated, the electronics board 140 is located within board receiving feature 126 and is adjacent actuator 180. An electronics connector 60 may be electronically coupled to the electronics board 140 and may extend from the electronics board 140, through connector hole 129, and to the controller assembly 200. The electronics connector 60 may be an electric wire with an outer casing. Electronic hardware 142 may be coupled to and adjacent the electronics board 140. The electronic hardware 142 may include sensors, sound sources, such as speakers and piezoelectric sound generators, and light sources, such as light emitting diodes.

Figure 6:
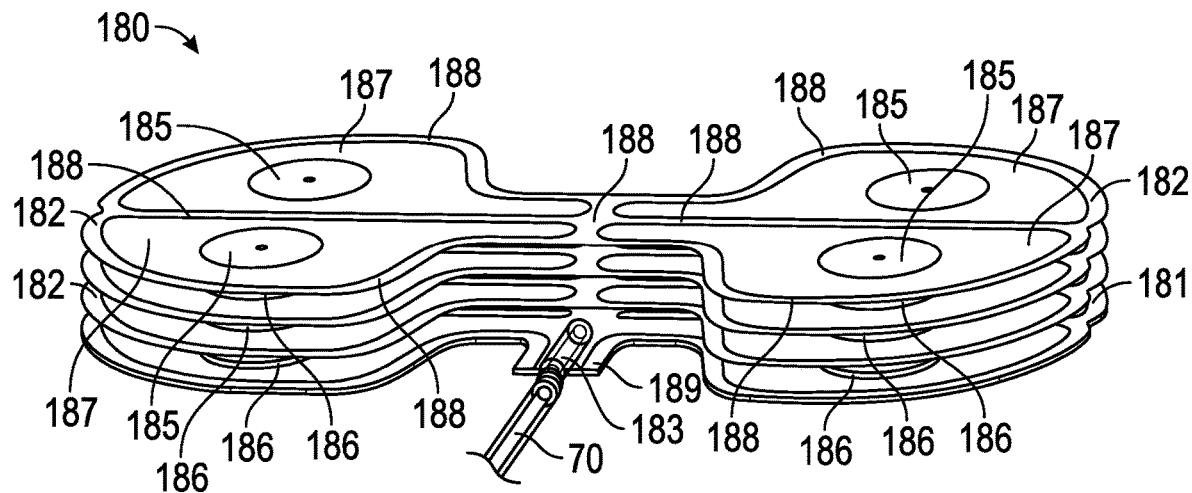
FIG. 6 is an illustration of a perspective view of the pneumatic actuator of FIGS. 4 and 5.
Figure 7:
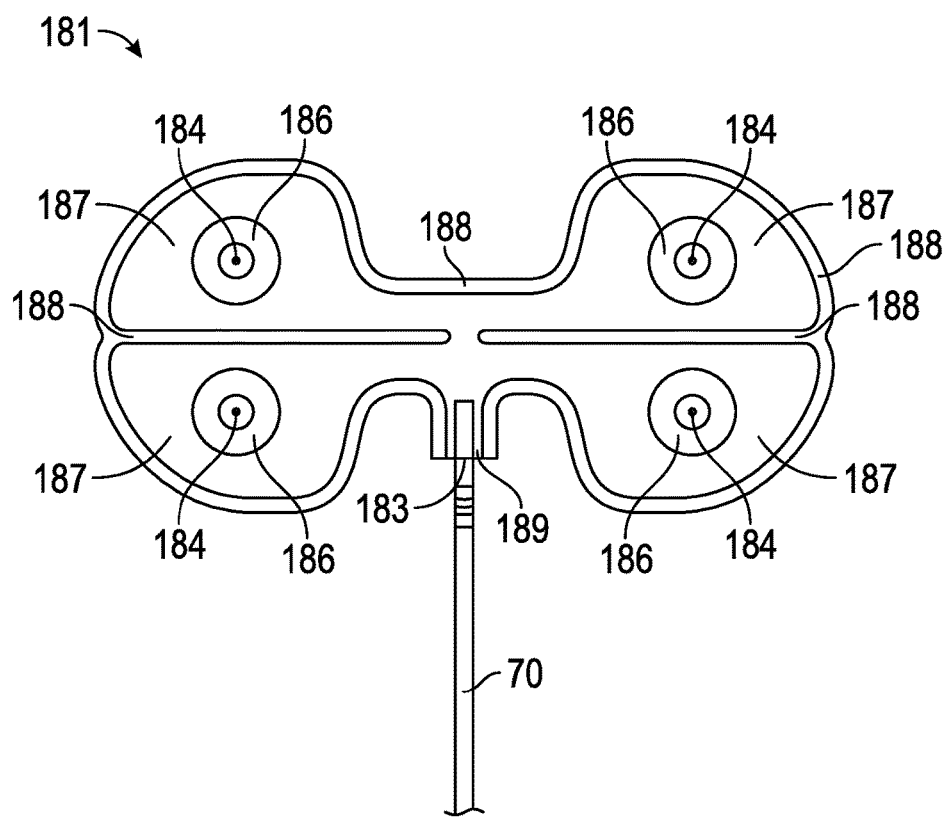
FIG. 7 is a top view of a bellows 182 of FIG. 6.

FIG. 6 is an illustration of a perspective view of the pneumatic actuator 180 of FIGS. 4 and 5. FIG. 7 is a top view of the first bellows 181 of FIGS. 5 and 6. Referring to FIGS. 6 and 7, each bellows is made of an inflatable material that includes one or more pneumatic compartments 187 surrounded by a compartment boundary 188. The bellows and the various compartments 187 are manifolded together. In the embodiment illustrated, the bellows have manifolds between compartments 187 of adjacent bellows as described herein. In other embodiments, a manifold can be used to plumb each bellows separately. In other embodiments, each bellows is plumbed to a separate fluid source and actuated separately. The pneumatic compartments are configured to inflate such that the pneumatic compartments expand and distribute the pneumatic force over different regions of the top plate 110 and bottom plate 150. The shape, size, and number of layers of the bellows 182 within the actuator 180 may be selected based on the desired force at a given pressure. In embodiments, the nominal force is 20 lbf. In some embodiments, the force should not vary by more than 15%. In some embodiments, the force should not vary by more than 3 lbf.

The shape of the bellows 182 may also be configured to maximize the transmission of forces as well as the magnitude of distraction. Changing the shape of the bellows 182 may change the surface area which may change the magnitude of the force (for the same pressure). Changing the shape of the bellows 182 can also affect the location of the center of application of the force.

In the embodiment illustrated, the first bellows 181 and the second bellows 182 have the same general dog bone shape. The first bellows 181 has four compartments 187 with each compartment 187 in one quadrant of the first bellows 181. Each compartment 187 is a quarter of the dog bone shape. In the first bellows 181 the four compartments 187 are in direct fluid communication. The compartment boundary 188 for each compartment is open to the other compartments 187 along the neck of the dog bone shape. The first bellows 181 may include a fluid communication hole 184 through the top of each compartment 187, on the bottom of each compartment 187, or through both.

The first bellows 181 also has a fluid connection tab 189 and a fluid supply connector 183. The fluid connection tab 189 may extend out from the neck of the dog bone shape and be in fluid communication with the fluid supply connector 183. The fluid supply connector 183 is configured to fluidly connect the first bellows 181 to the fluid supply line 70.

The second bellows 182 has four compartments 187 with each compartment 187 in one quadrant of the second bellows 182. Each compartment 187 is a quarter of the dog bone shape. In the second bellows 182 the four compartments 187 are not in direct fluid communication. The compartment boundary 188 for each compartment completely encloses the compartment off from the other compartments 187. The second bellows 182 may include a fluid communication hole 184 through the top of each compartment 187, on the bottom of each compartment 187, or through both.

The actuator 180 may include multiple annular seals 186 and multiple seals 185. In the embodiment illustrated, annular seals 186 are adhesive rings and seals 185 are adhesive disks. In other embodiment, annular seals 186 and seals 185 are formed by bonding the bellows to the adjacent structure, such as an adjacent bellows, a top plate 110, or a bottom plate 150. In some embodiments, the annular seals 186 and seals 185 are formed using RF welding. An annular seal 186 may be located between adjacent compartments 187 of adjacent bellows, such as the first bellows 181 and a second bellows 182 or two adjacent bellows 182. The annular seal 186 seals the adjacent compartments 187 around the adjacent fluid communication holes 184 so that the adjacent compartments 187 are manifolded together in fluid communication. In embodiments, the annular seals 186 and manifold formed by thereby can withstand a vacuum. The seals 185 are located at the outer surface of a compartment 187 that is not adjacent to another compartment 187. The seals 185 may be configured to seal a fluid communication hole 184 and may attach the first bellows 181 or the second bellows 182 to either the top plate 110 or the bottom plate 150.

Figure 8:
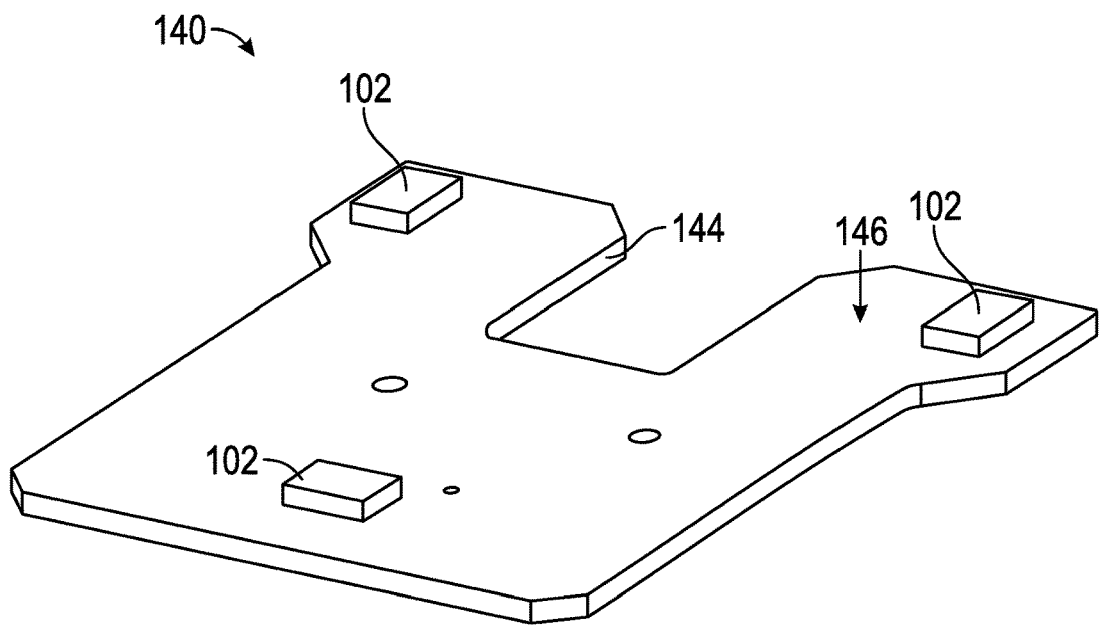
FIG. 8 is an illustration of a perspective view of the electronics board of FIGS. 4 and 5.

FIG. 8 is an illustration of a perspective view of the electronics board of FIGS. 4 and 5. The electronics board 140 may include a board surface 731 that faces the bottom plate 150 with the actuator 180 there between (as shown in FIGS. 5 and 6). One or more sensors 102 may be connected to the electronics board 140. The location and number of sensors 102 may correspond to the number and placement of the one or more magnets 104 located at the bottom plate 150 (shown in FIG. 7B). The sensors 102 may detect the distance from the magnets 104, which may allow the distance and the angle between the top plate 110 and the bottom plate 150 to be determined.

Spring-Actuated Mechanisms

In some embodiments, the insert 100 is configured with one or more mechanical actuators 180, such as constant or variable force springs, which apply a load to the plates and the adjoining bone structures of the joint. The number and type of actuators 180 may vary depending on numerous factors, including the intended function of the device and the amount of control needed over the actuation process.

Figure 9:
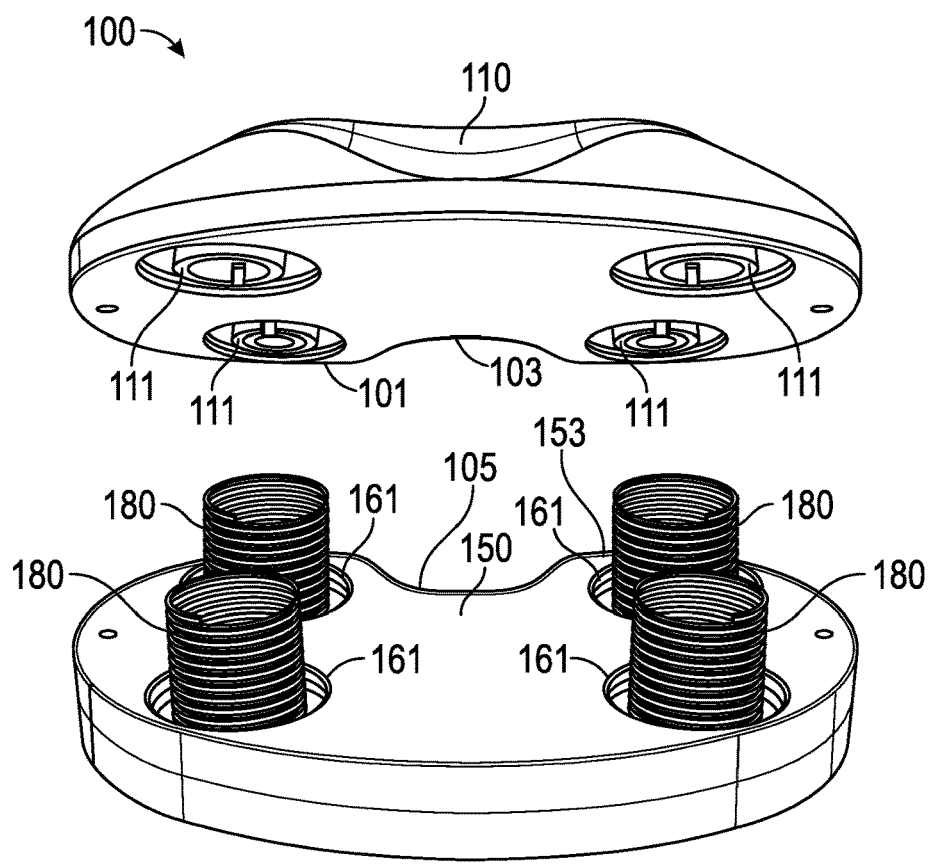
FIG. 9 is an exploded view illustration of an embodiment of the insert of FIG. 1 with a plurality of spring actuators.

FIG. 9 is an exploded view illustration of an embodiment of the insert of FIG. 1 with a plurality of spring actuators. Referring to FIG. 9, the actuators 180 are springs. The actuators 180 are not permanently attached with the top plate 110 and bottom plate 150 and can therefore be easily removed in order to exchange them with different actuators that have a different stiffness. In addition, the unattached actuators 180 also allow for the exchange of the top plate 110 and/or bottom plate 150 with plates of different size, shape and thickness in order to best match the needed dimensions of the area where the insert 100 is being positioned. The unattached actuators 180 may then be secured within the insert 100 by providing top actuator recesses 111 in top plate 110 and bottom actuator recesses 161 in bottom plate 150. The top plate 110 and bottom plate 150 may also be connected with each other by a flexible or elastic tether that holds the entire insert assembly together.

Alternatively, the actuators 180 may be attached (either permanently or removably) with the top plate 110 or bottom plate 150 (or both) by one or more attachment mechanisms. In one example, the ends of the actuators 180 may be bonded to the top plate 110 and the bottom plate 150 with various glues such as cyanoacrylate or potted in plate with epoxy, polyurethane, etc. The actuators 180 could also be manufactured with customized ends which snap into a corresponding retaining mechanism on the respective top plate 110 and bottom plate 150 and lock the ends of the actuators 180 into place. The actuators 180 could also be manufactured and formed within one or both of the top plate 110 and bottom plate 150.

The shape and dimensions of the spring-actuated mechanism may also vary considerably, but in the embodiments described and illustrated herein, the actuators 180 are springs which are cylindrically-shaped with a diameter of approximately 4-8 millimeters (mm) and an expandable height of approximately 6-10 mm. The actuators 180 may be configured to apply a force in the range of 1-50 pounds per actuator, have a force accuracy of approximately 1 percent and a displacement accuracy of approximately 0.2 mm. When a plurality of actuators 180 are used, each actuator 180 may be independently controlled and expanded or contracted in order to obtain an angled, or tilted top plate 110 or bottom plate 150, as has been previously described. The number of actuators 180 used may vary between one to four or more, and may depend on the size of the actuator 180 and surface areas of the top plate 110 and the bottom plate 150 on which they are disposed. The actuators 180 may have varying stroke lengths, shapes, dimensions and force capacities.

In one embodiment, actuators 180 are helical or coil springs that generate force when compressed. In another embodiment, actuators 180 are conical or volute springs, in which the coils slide over each other, thus permitting greater travel for the same resting length of the spring. In yet another embodiment, actuators 180 are cantilever springs that bend when compressed. The springs could be made of common materials such as metals (steel, titanium, aluminum), polymers, or rubbers. In the embodiment illustrated in FIG. 9, 4 coil springs are located between a top plate 110 and bottom plate 150. The bottom plate 150 may contain the force, displacement, and angle measurement sensors, a microprocessor powered by a battery, and a radio for wireless communication.

As illustrated in FIG. 9, the top plate 110 can include a top plate insertion end 101 in the shape of a portion of a cassini oval. The general shape may result in each side of the top plate insertion end 101 being rounded and including a top plate indent 103 between each rounded side. Similarly, the bottom plate 150 can include a bottom plate insertion end 153 in the shape of a portion of a cassini oval. The general shape may result in each side of the bottom plate insertion end 153 being rounded and including a bottom plate indent 105 between each rounded side.

Different configurations of actuators 180 provide advantages and disadvantages. The choice of a particular configuration of actuators 180 may therefore depend on the specific intended use and desired features for the actuation and measurement, which could vary from one surgeon to another. The use of a mechanical spring as an actuator would allow for the insert to be an entirely wireless device. Wireless sensors coupled with constant force springs provide an insert which would not require any physical connections, and as such could be easily removed and replaced during the balancing process. In addition, a spring-actuated device could be permanently implanted into the joint, whereas other inserts would need to be removed and then replaced with an identically-shaped permanent prosthesis. In a further embodiment, the actuators may be locked into a final position and then disconnected from the external controller and power source.

Figure 10:
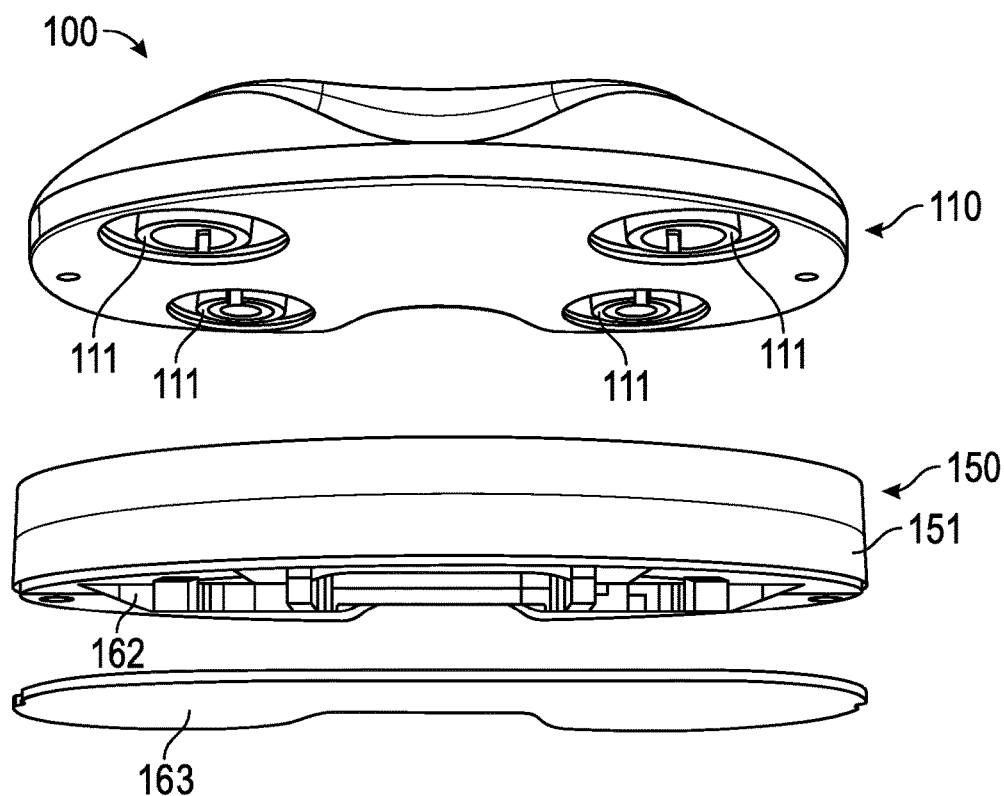
FIG. 10 is an alternate exploded view illustration of the insert of FIG. 9 without the actuators.

FIG. 10 is an alternate exploded view illustration of the insert 100 of FIG. 9 without the actuators. In the embodiment illustrated, bottom plate 150 includes an electronics recess 162 extending from the outer surface of the bottom plate body 151, opposite the bottom actuator recesses 161. The electronics recess 162 may house the electronics board 140 and other electronics, such as any sensors, microprocessors, power modules or radios which communicate the sensed data to. The insert 100 may include a bottom plate cover 163 that connects to the bottom plate body 151 and covers the electronics recess 162.

Materials, Shapes and Configurations

The insert 100 may be made from any combination of biocompatible or medical-grade polymers or metal alloys, as known to one of skill in the art. The biocompatible material may be rated for limited contact. The materials would be required to meet structural and mechanical specifications needed to sustain the pressures, temperatures, fluids and frictions with other components of the insert and any adjoining bone surfaces, cartilage, ligaments and other tissues. The material of the top plate 110 and in particular of the articular contacting surface 139 should be a material that will not damage the articular surface of the femoral bone or component. The insert 100 should also be made from materials which can be sterilized in order to minimize the risk of infection during surgery. The material requirements will also apply to the actuators and in some aspects to the sensors, particularly with regard to the sterilization and durability requirements. In embodiments, the insert 100 may include radiopaque markers or material for use in fluoroscopic x-ray verification.

The size of the insert 100 may vary depending on the patient or the type of joint. The insert could conceivably be manufactured in several different sizes for different sized joints, such as a small, medium and large option. In one embodiment, a medium-sized insert would be approximately 70 millimeters (mm) by 45 mm and have an adjustable height of 8-14 mm. The height of the insert may need to be adjusted separately from the actuation mechanism in order to initially fit within the space of the joint between opposing bone structures. This may be accomplished using shims. In some embodiments, shims include a height from 1-6 mm and may be provided in 1 mm increments. In embodiments, the articular portion 130 may be switched out for one with a different height for the initial fit of the insert 100 within the space of the joint. The actuator 180 could then provide additional movement and spacing of at least a maximum height change. In one embodiment, the maximum height change of the insert is of 4-8 mm. In another embodiment, the maximum height change is 5-7 millimeters. In yet another embodiment, the maximum height change is at least 6 mm. The other dimensions of the device may also be adjustable in order to better fit a desired shape and size of the joint and the adjoining bones, ligaments or cartilage. The insert 100 may also be configured to be stable in shear between the top plate 110 and the bottom plate 150 throughout the range of motion of the knee. In some embodiments, the stiffness of the bellows under inflation may be configured to resist shear. In embodiments, the insert can resist a side load of 5 lbf. In some embodiments, the range of dynamic knee flexion angle measurement of the insert 100 may be from 10 degrees of hyperextension to 140 degrees of flexion.

Figure 11:
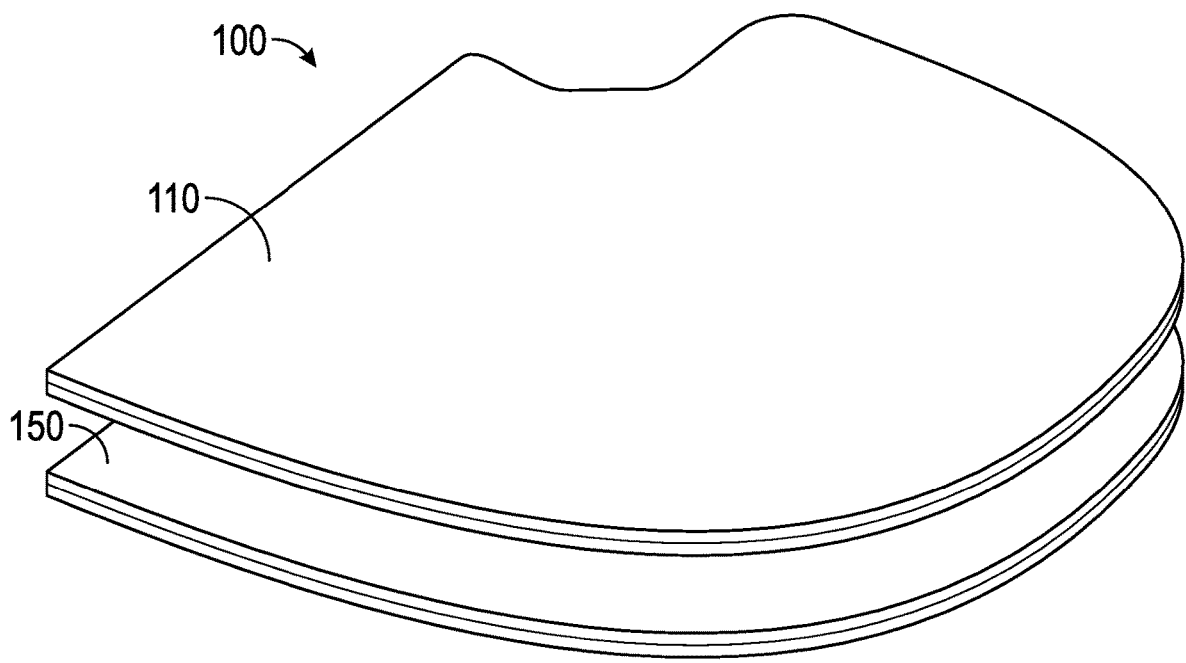
FIG. 11 is a perspective view illustration of an embodiment of the insert of FIG. 1 with a unicompartmental configuration.

The shape of the insert may also vary depending on the intended use of the device. The insert 100 may have a tricompartmental, bicompartmental, or a unicompartmental design. The embodiments illustrated in FIGS. 2 to 10 have a tricompartmental design. FIG. 11 is a perspective view illustration of an embodiment of the insert of FIG. 1 with a unicompartmental configuration. The insert 100 with a unicompartmental design may be essentially half of the tricompartmental design bisected down a longitudinal middle of the device. The insert 100 with a unicompartmental design still includes a top plate 110 and a bottom plate 150 separated by one or more actuators. An insert 100 with a unicompartmental design may be advantageous for various types of surgical procedures, such as arthroplasty, in particular a partial knee replacement where only one half of the knee joint is replaced. A partial knee replacement arthroplasty preserves some of the ligaments in the knee, and the insert 100 can be placed on only one half of the joint to allow for balancing of the joint with actuation that similarly avoids the need to remove additional ligaments in the knee. The number of actuators in a partial knee replacement may vary according to user preference or the specifications of the joint balancing process when only part of the knee joint is being replaced.

Multiple inserts 100 with a unicompartmental design may also be utilized in a full knee replacement where the central cruciate ligaments are to be preserved by sliding each insert 100 from lateral sides of the knee joint.

The top plate 110 and the bottom plate 150 may be modular to allow for easy placement of different types of sensors and actuators. Although the illustrated embodiments of the plates are substantially flat, the plates may take different shapes to accommodate certain types of sensors, actuators and adjoining bone or other tissue. In one embodiment, the plates may have an elastic property to allow them to slightly deform when a load from an adjoining bone is applied (such as that of the femoral condyles). The elastic plates may be made from rubbers, polyurethane, silastic, gel-filled or air-filled containers.

In some embodiments, the insert may be configured with a rotating bearing disposed in a central portion of the space between the top plate and the bottom plate. The bearing would provide for the top plate to rotate relative to the bottom plate, providing an additional adjustment that can be made to better balance the joint. The bearing may be configured to provide for approximately 5-10 degrees of rotation of the top plate with respect to the bottom plate (or vice versa depending on the configuration of the bearing) or translation from side-to-side and front-to-back.

The insert may also be configured with only a single plate and a set of actuators which interface with an opposing bone surface, in one embodiment of the invention.

Controller

Figure 12:
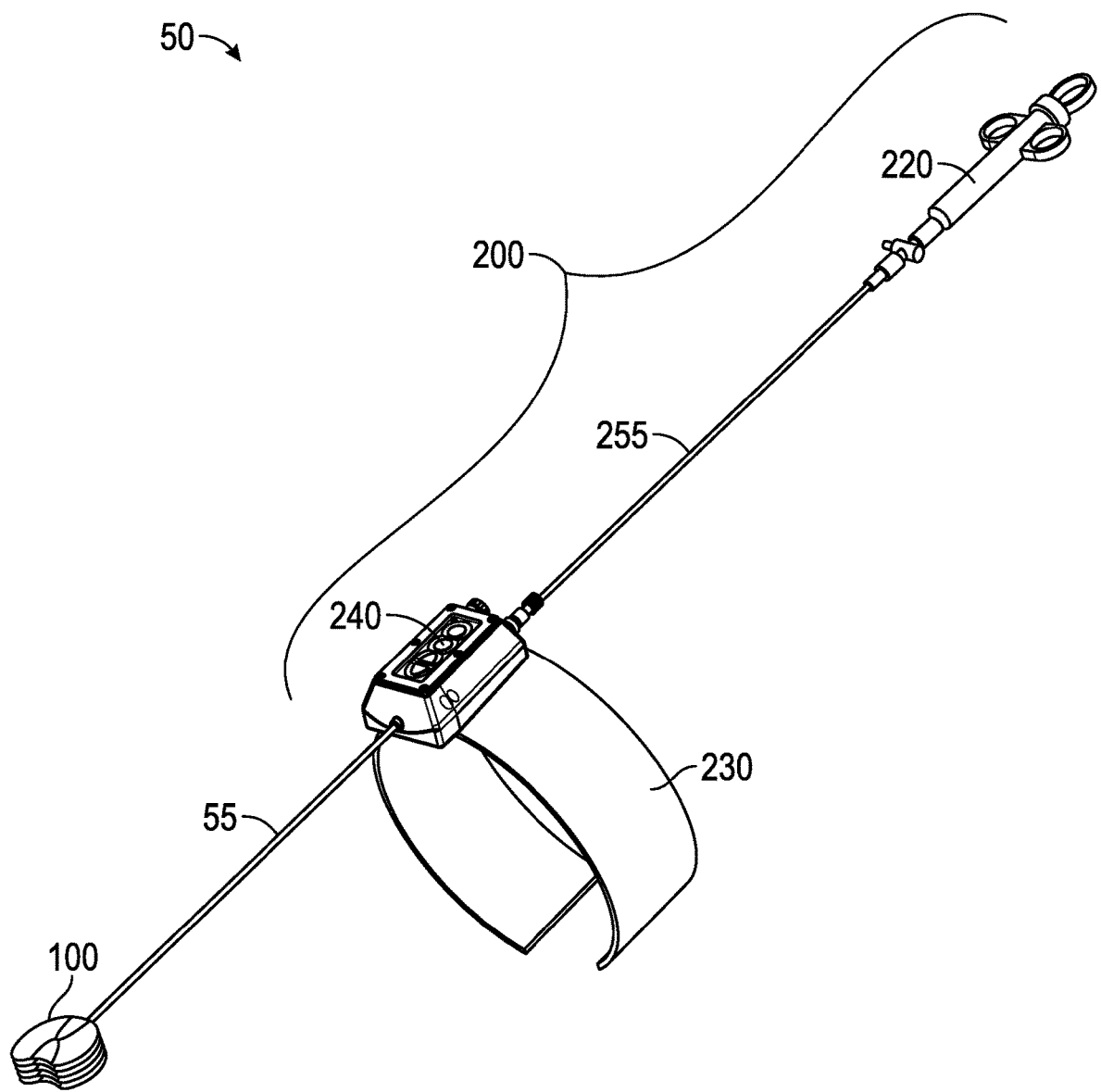
FIG. 12 is an illustration of a perspective view of an embodiment of the controller assembly of FIG. 1 connected to an insert.

FIG. 12 is an illustration of a perspective view of an embodiment of the controller assembly 200 of FIG. 1 connected to an insert 100. In the embodiment illustrated, the insert 100 is a pneumatic insert, such as the insert 100 of FIGS. 4 and 5. Controller assembly 200 may include a controller 240, a controller mount 230, and a fluid supply device 220. The controller mount 230 may be a strap or a similar mechanism for mounting the controller 240 on to the patient's limb, such as the thigh. In embodiments, the controller mount 230 has a width that is the length of controller 240. The controller mount 230 may be affixed to the patient's limb using a fastener, such as a hook and loop fastener. The insert 100 may be connected to the controller 240 by an insert connection 55. The insert connection 55 may include the fluid supply line 70 and the electronics connector 60 shown in FIGS. 4 to 7.

The fluid supply device 220 may be an automated source of fluid power, or may be a manually operated source of fluid power, such as a pneumatic syringe as illustrated in FIG. 12. The fluid supply device 220 may be configured to supply fluid, such as a gas, to the controller 240 and to the insert 100 to actuate the bellows 182 (shown in FIGS. 4 to 6) of the insert 100. The gas may be air, such as room air, carbon dioxide, nitrogen, or helium. The fluid supply device 220 may be connected to the controller 240 by a controller supply line 225. The controller supply line 225 may be a tube extending from the controller 240 to the fluid supply device 220. In some embodiments, a pressure relief valve 226 may be located at the end of controller supply line 225 adjacent controller 240. The pressure relief valve 226 may ensure that the pneumatic actuator 180 is not filled above a predetermined maximum pressure, such as 30 psi.

Figure 13:
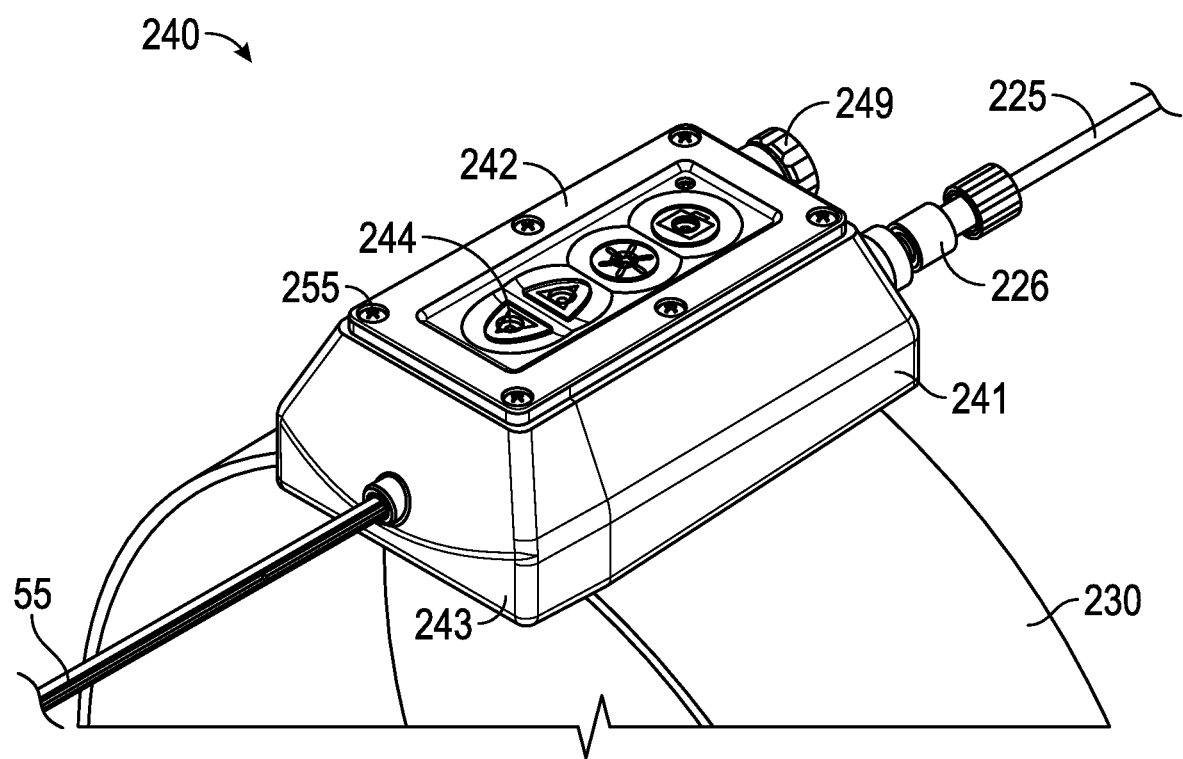
FIG. 13 is an illustration of a perspective view of the controller of the controller assembly of FIG. 12.

FIG. 13 is an illustration of a perspective view of the controller 240 of the controller assembly 200 of FIG. 12. The controller 240 may include a housing body 241, a housing side 243, and a housing cover 242. The housing body 241 may include the back and three sides of the housing of controller 240. Housing side 243 may attach to an end of housing body 241 forming the fourth side of the housing. Housing cover 242 may fasten to the housing body 241 and the housing side 243 to form the enclosure of the housing. A button membrane 244 may cover a number of buttons 251 (shown in FIG. 15) that are accessible through housing cover 242. A battery cover 249 may attach to an end of housing body 241, opposite housing side 243 and may provide access to a battery 248 (shown in FIG. 14).

Figure 14:
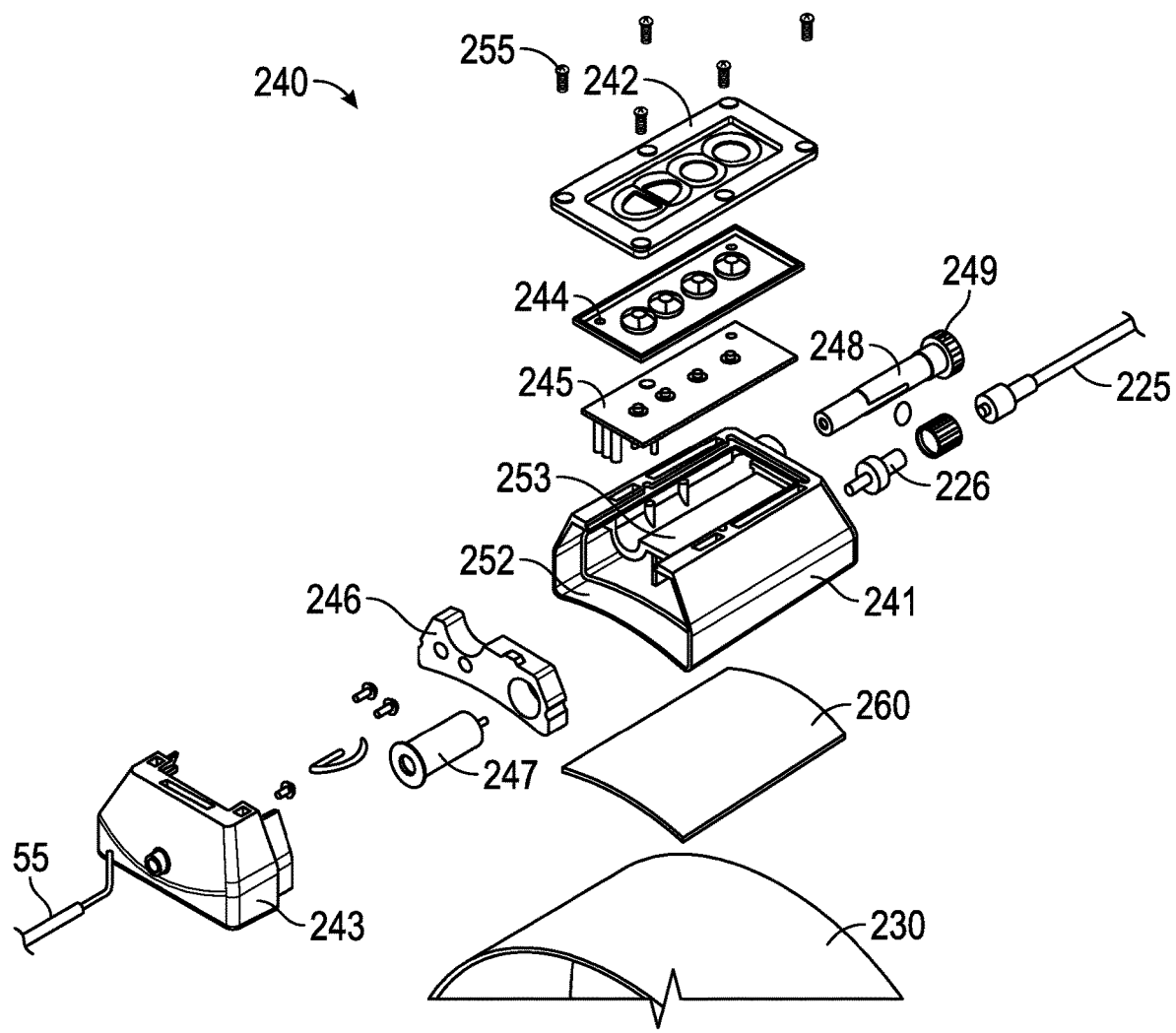
FIG. 14 is an illustration of an exploded view of the controller of FIG. 13.

FIG. 14 is an illustration of an exploded view of the controller 240 of FIG. 13. Housing body 241 may be configured with an electronics chamber 253 and an accumulator chamber 252. A battery 248 and controller electronics 245 may be housed within electronics chamber 253. In embodiments, the battery 248 has enough power for the controller 240 to operate for at least an hour. Controller electronics 245 may include, inter alia, a controller electronics board 250, buttons 251, a transmitting radio, and sensors, such as an angle sensor 254. Controller electronics board 250 is in electronic communication with electronics board 140, such as wireless or wired communication. In embodiments, the electronics connector 60 electronically connects and is coupled to the controller electronics board 250 and the electronics board 140. Buttons 251 may be affixed to controller electronics board 250. The angle sensor 254 may provide the angle of the thigh which may indicate the angle of the knee flexion. The angle sensor 254 may be an accelerometer, an inclinometer, or a similar device.

The accumulation chamber 252 may smooth out pressure fluctuations as the pneumatic actuator(s) of the insert 100 undergo compression and expansion. Housing side 243 may form a seal with housing body 241 to prevent leaking from accumulation chamber 252.

Controller 240 may also include a pressure sensor 247 for detecting the pressure of the actuating fluid within accumulation chamber 252, and a sensor mount 246 configured to hold pressure sensor 247 in place. The sensor mount 246 may be sized and shaped to be held within housing body 241 by housing side 243. In embodiments the controller 240 also includes a Light emitting diode (LED). The LED may show, inter alia, when the controller 240 is activated.

Controller 240 may be fastened to controller mount 230 with a mounting fastener 260. In the embodiment illustrated, mounting fastener is a hook and loop fastener. In other embodiments, other types of fasteners may be used.

In some embodiments, controller functions as a wireless remote and may be configured to transmit the data from the insert 100, including the various sensors and the data from the controller 240, including the pressure sensor 247, to the display system. In other embodiments, controller 240 may also serve as a display device when a suitable display screen is included as part of the controller 240. In further embodiments, the controller 240 is directly wired to a display device.

When using the joint balancing system 50, the insert 100 may be placed within the appropriate joint (such as the knee joint in this example). The controller 240 may be charged by the surgeon/operator using fluid supply device 220, such as a pneumatic syringe, to pump up the pressure. In embodiments, the pneumatic syringe is a 20 mL syringe. The pressure may be monitored by a pressure sensor 247. The pressure may be displayed by the display module 320 in the graphic user interface on a display screen. In some embodiments, the optimum pressure is between 20 and 30 psi. In some embodiments, the pressure may be modified to exert a defined force. The optimum force may be between 40 and 200 N. Joint balancing system 50 may be configured to supply pressures at different ranges, depending on the application. With the insert 100 inflated (i.e. bellows expanded under pressure to actuate the insert 100), the knee is flexed (bent) through the full range of available motion. As the knee is flexed, the sensors may measure knee flexion angle, the distance between the top and bottom plates of the insert, and the tilt between the top and bottom plates of the insert. This information may be graphically depicted by wired or wireless transmission to the display.

The surgeon can make the appropriate changes to the placement of the artificial components, to the cuts made in the bone, or to the ligaments of the knee to generate a distraction gap and tilt that is most desirable for the patient.

The joint balancing system 50 may be used to balance the knee during a surgical procedure, such as a total knee arthroplasty or a partial knee arthroplasty. The controller mount 230 may be wrapped around a patient's thigh, such as the lower thigh and tightened firmly. The hook and loop fastener of the controller mount 230 may be placed anteriorly on the thigh. The controller 240 may be aligned with the long axis of the patient's thigh, with the battery cap 249 and the pressure valve 226 facing proximally and the insert connection is facing distally.

The insert 100 may be positioned in between the tibial and femoral surface. The bottom surface of the bottom plate 150 may be flat and may be in direct or indirect contact with the tibial bone cut. The upper surface of the top plate 110 may be curved and may be in direct or indirect contact with the femoral surface. The insert 100 should fit comfortably and may be centered on the tibial cut surface. The surgeon may verify that the curved upper surfaces articulate with the femoral condyles. If the insert 100 cannot be inserted easily, the surgeon may verify that the gap between the tibial cut surface and the femoral condyles is at least the height of the insert 100, such as 8 mm. If the insert 100 is too big or too small for the knee, the surgeon may select an insert of a different size.

The actuator may then be pressurized by the fluid supply device 220 to a predetermined pressure, such as from 20 psi to 25 psi, and the display module 320 may display the current pressure in the GUI. The insert 100 may be expanded from a first predetermined height, such as 8 mm, where the insert 100 is not inflated up to a second predetermined height, such as 14 mm, where the pneumatic actuator is fully inflated. Shims may be used when the tibiofemoral gap is greater than the second predetermined height. In other embodiments, the articular portion 130 may be interchanged with a thicker articular portion 130 when the tibiofemoral gap is greater than the second predetermined height.

Once the insert 100 is positioned in the tibiofemoral gap and inflated, the joint balancing system 50 may be calibrated by holding the knee in 0° flexion and selecting a calibration button displayed by the control module on the GUI.

The display module 320 may also display the net gap between the tibial and femoral surfaces in real time. To check gap in flexion and extension: hold the knee in 0° and read the gap off the display. Then flex the knee to 90° and read the gap off the display. This process can be repeated as many times as needed. If the surgeon desires to recut the bones or reposition the components, the insert 100 can be removed (after deflating the controller). If the surgeon desires to perform soft-tissue releases and there is sufficient access, he or she can perform the soft-tissue releases with the insert in place and monitor the changing gap in real-time on the display.

Joint balancing system 50 may also be used to measure the dynamic knee balance by flexing the knee gently between full extension and full flexion. The display module 320 may display the net gap between the tibial and femoral surfaces in real time in the GUI as well as record the gap and show a plot of the tibiofemoral gap against knee flexion in the GUI.

The balance of the knee can be changed and monitored in real time by releasing a ligament with the insert 100 in place and monitoring the changes in the tibiofemoral gap and tilt while the release is being performed. The balance of the knee can also be changed and monitored in real time by making suitable changes to the femoral or tibial cuts to realign the components.

In some embodiments, the joint balancing system 50 may also include a correction module. The correction module may interpret the data received from the insert 100 and the controller 240 and provide recommendations for a surgical procedure to correct any perceived imbalance. The correction module may receive other inputs including the bone geometry from an imaging modality, such as preoperative CT or MRI scans, the angle between adjacent bony structures, such as the angle between the femoral and tibial bone shafts, and ligament attachments, which may be based on digitizing landmarks using surgical navigation instruments.

The correction module may calculate the forces across the articular surfaces of the insert 210, such as by using rigid bodies to represent the bones and the insert 210, and using springs to represent the ligaments. The correction module may refine the ligament attachments, lengths, and stiffnesses to match force displacement data collected or determined by the sensors in the joint balancing system 50. The correction module may also calculate corrections to bone cuts and to the ligaments based on the lengths, stiffnesses, current angle of bone cuts, and the angle of the tibiofemoral shaft.

If the forces are balanced mediolaterally, but tight in flexion and in extension then the correction module may calculate an amount of bone to be cut from the proximal tibia based on the force-displacement data collected in extension and flexion. If forces are acceptable and balanced mediolaterally in flexion but tight in extension then the correction module may calculate an amount of bone to be cut from the distal femur based on the force versus displacement data collected in extension. The correction module may provide other recommendations, such as modifications to the ligaments based on the measured data.

Cutting Guides and Grinding Surface

Figure 15:
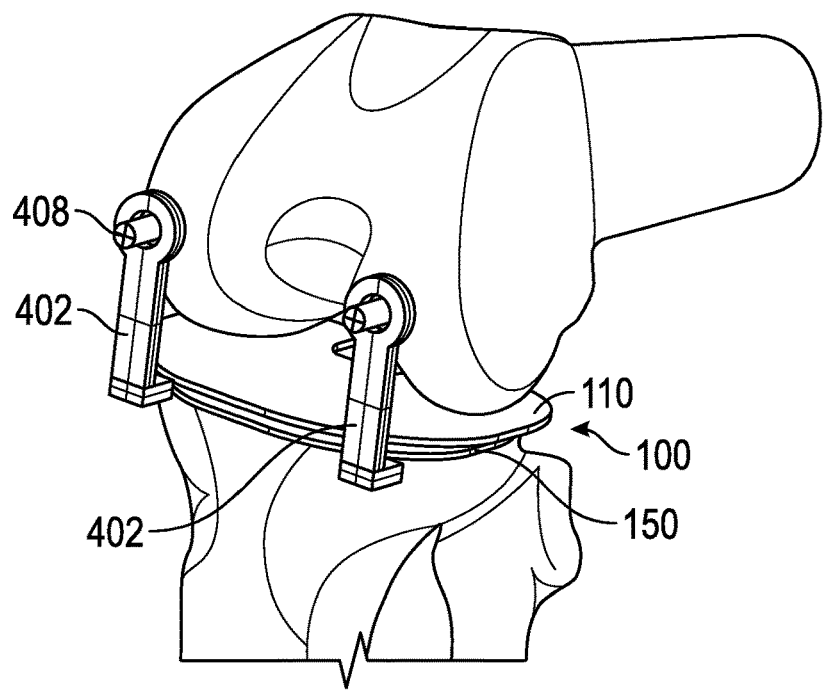
FIGS. 15 and 16 illustrate an embodiment of a cutting guide assembly connected to the insert that is used to guide cutting bone and tissue during balancing of the joint.
Figure 16:
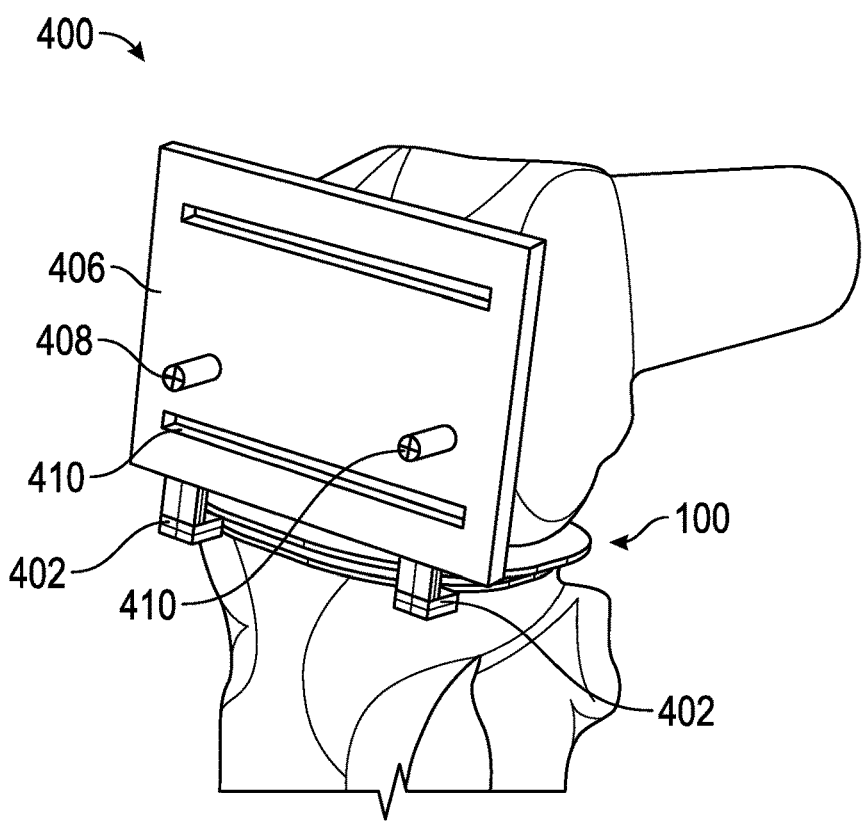
Figure 17:
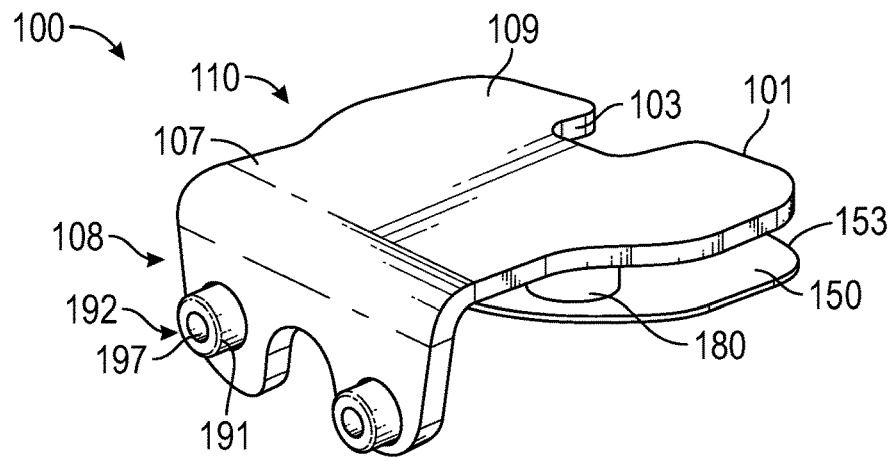
FIGS. 17-20 illustrate an embodiment of an insert with an integrated mount for a tibial cutting block.
Figure 18:
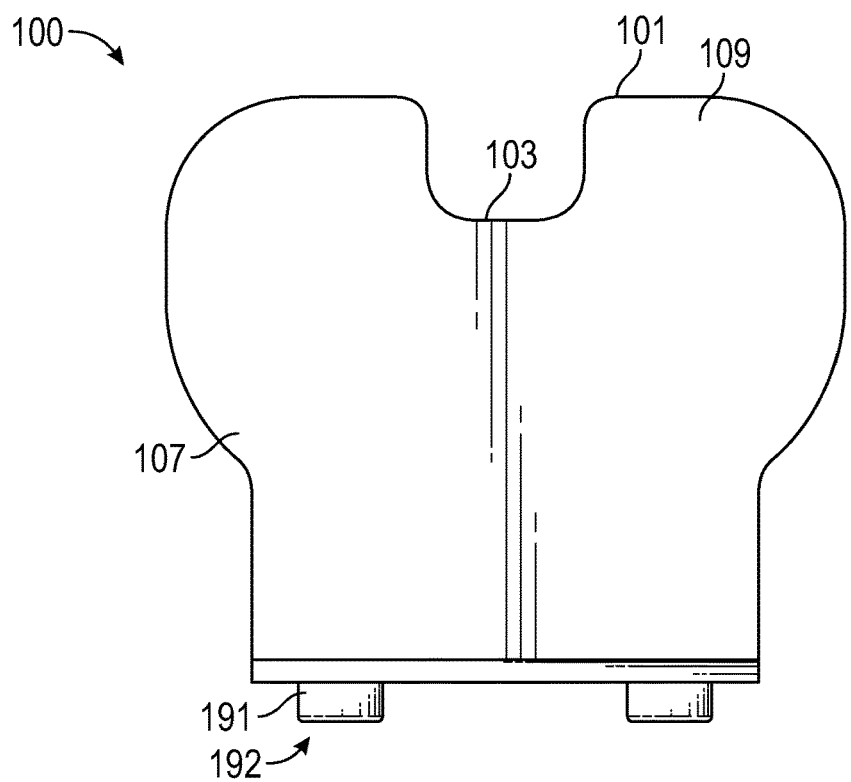
Figure 19:
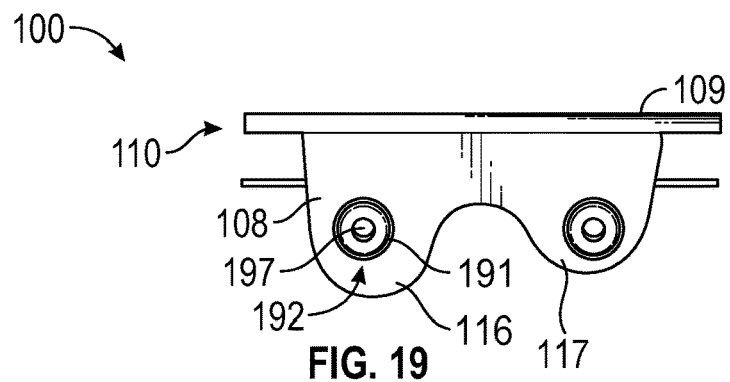
Figure 20:
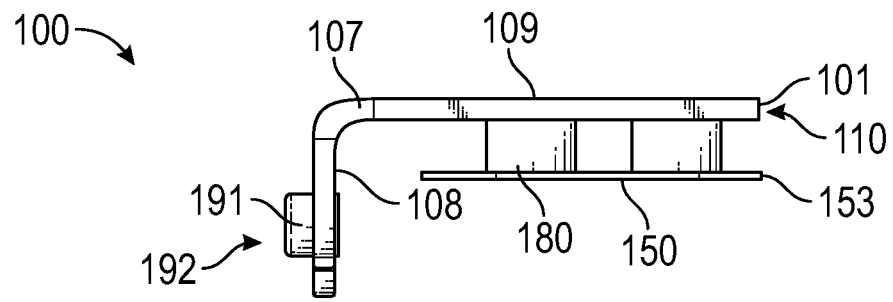
Figure 21:
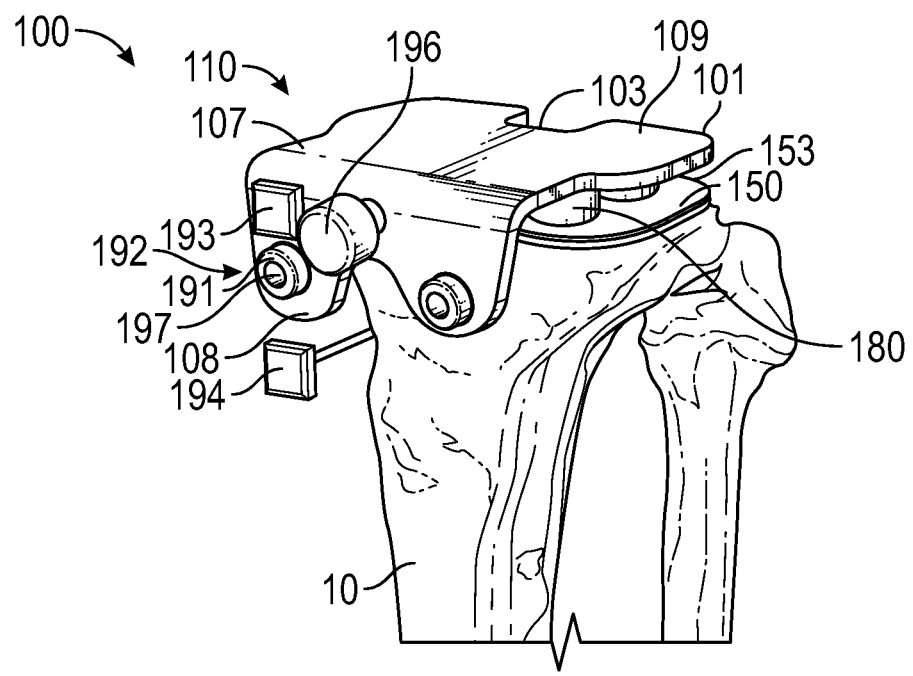
FIGS. 21-24 illustrate an alternate embodiment of the insert 100 of FIGS. 17-20.
Figures 22, 23:
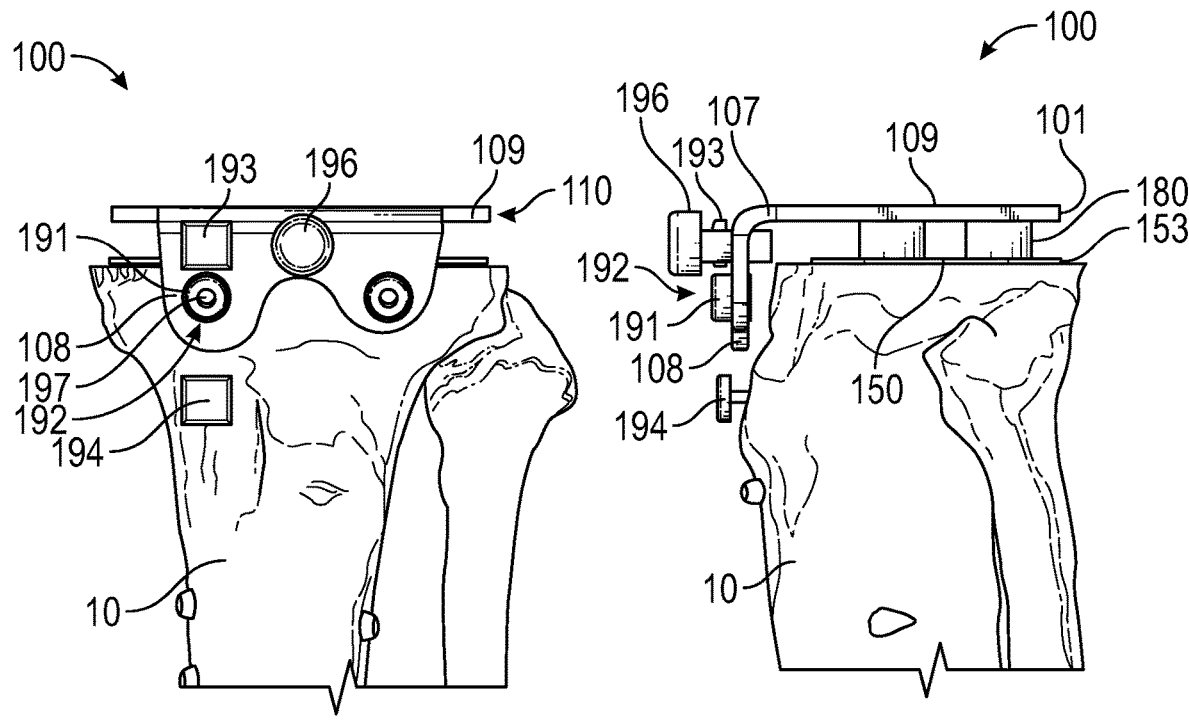
Figure 24:
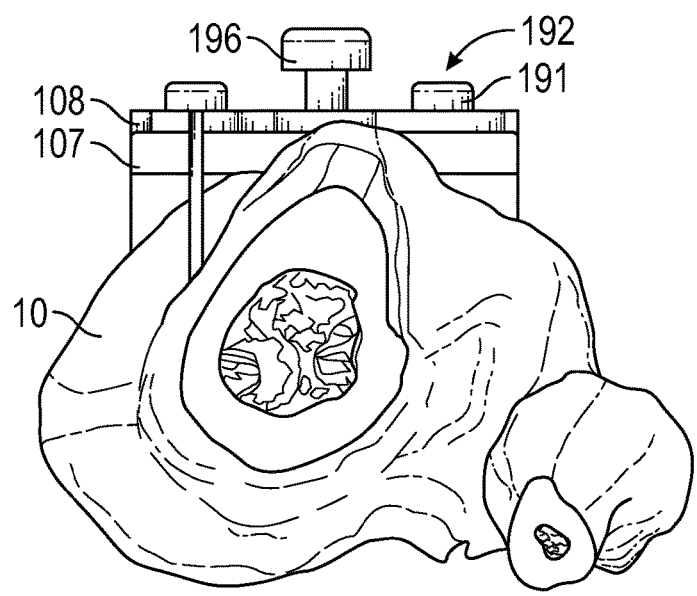
Figure 25:
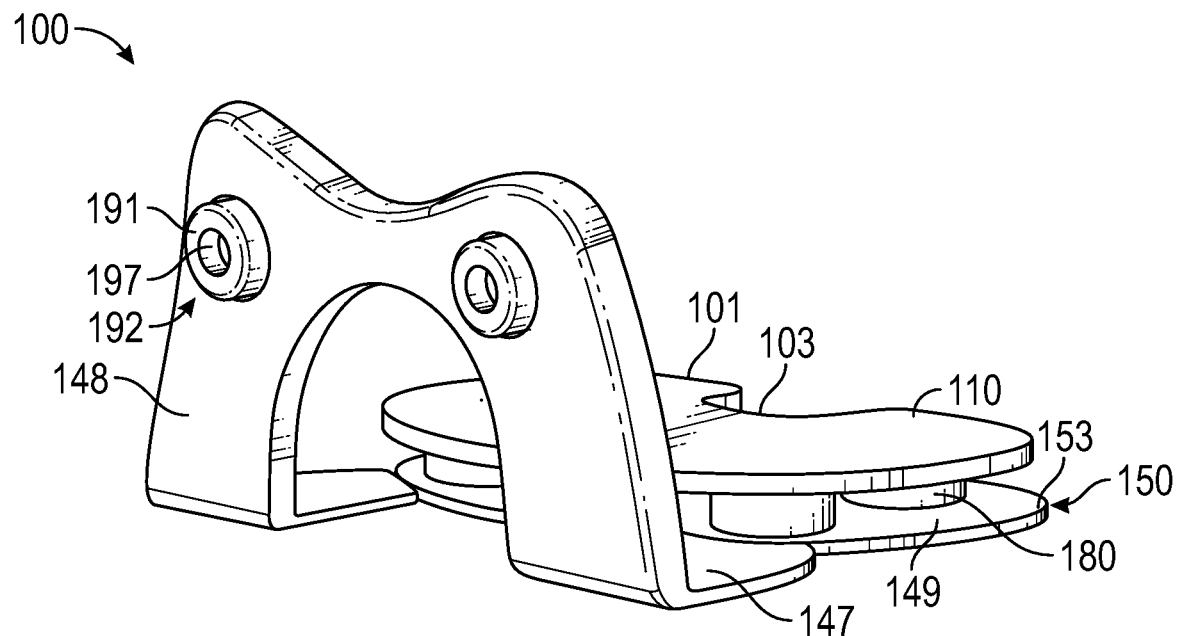
FIGS. 25-28 illustrate an embodiment of an insert with an integrated mount for a femoral cutting block.
Figure 26:
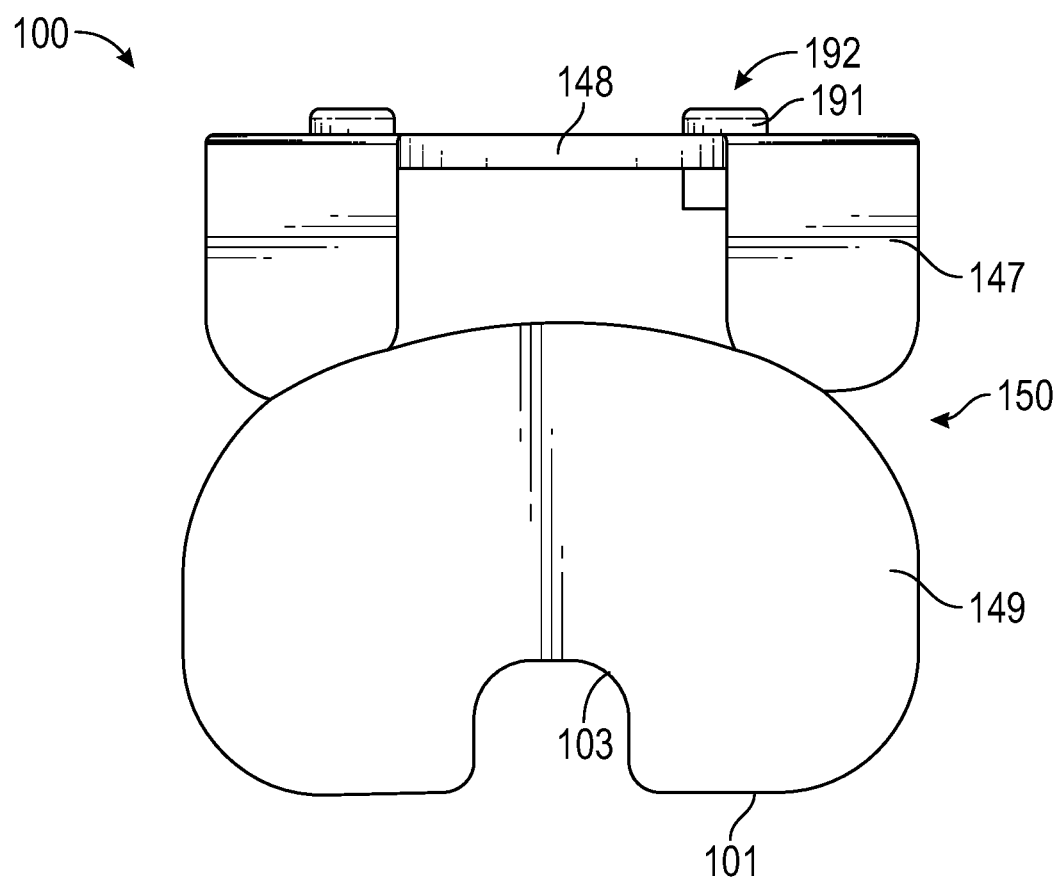
Figure 27:
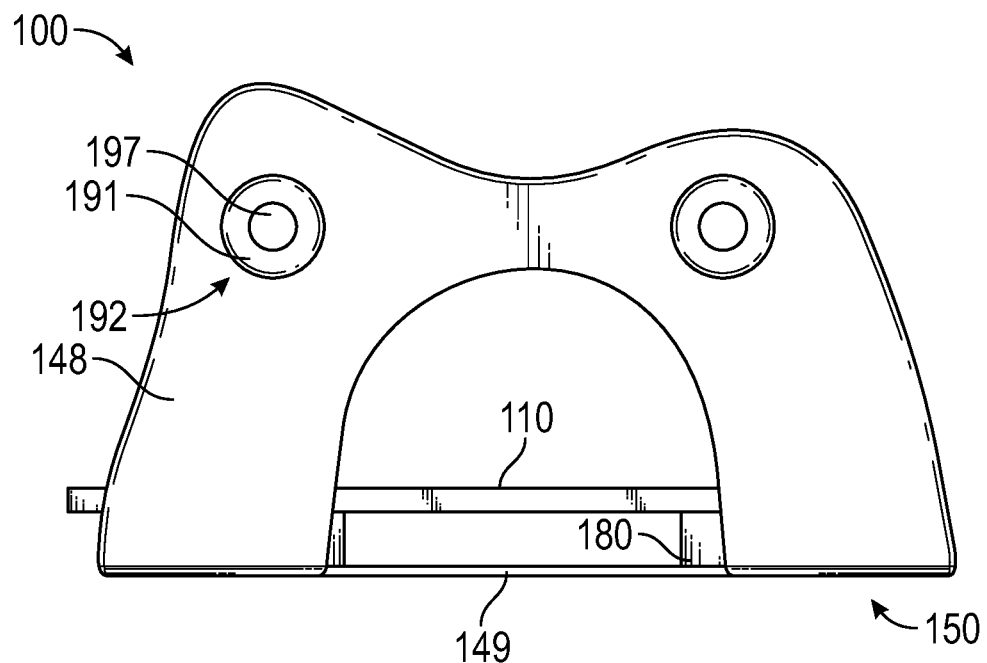
Figure 28:
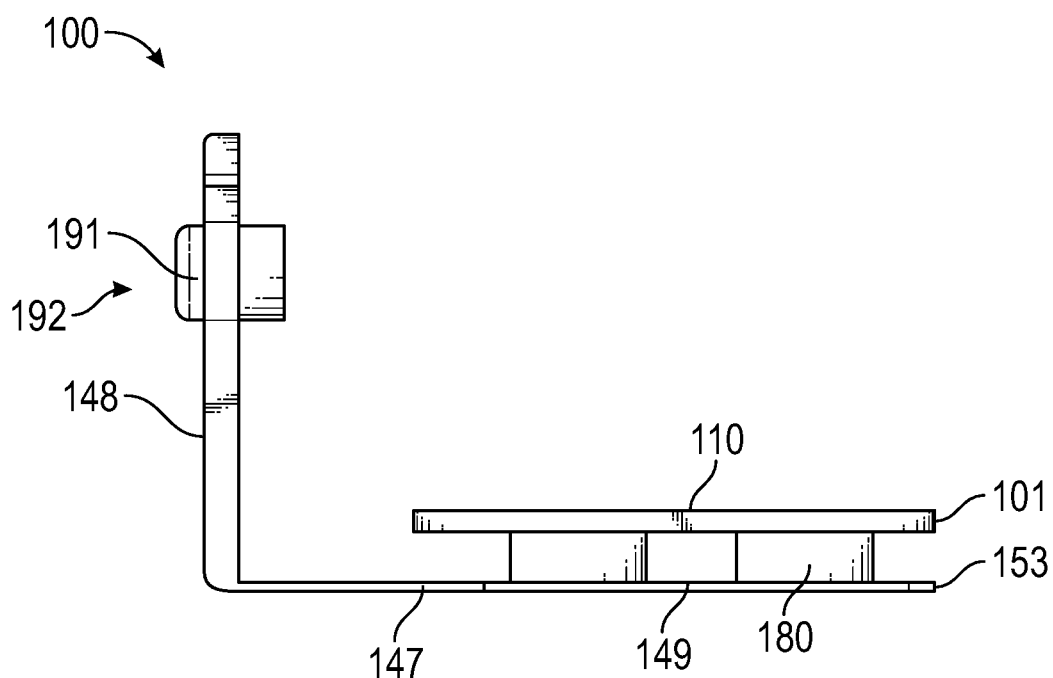
Figure 29:
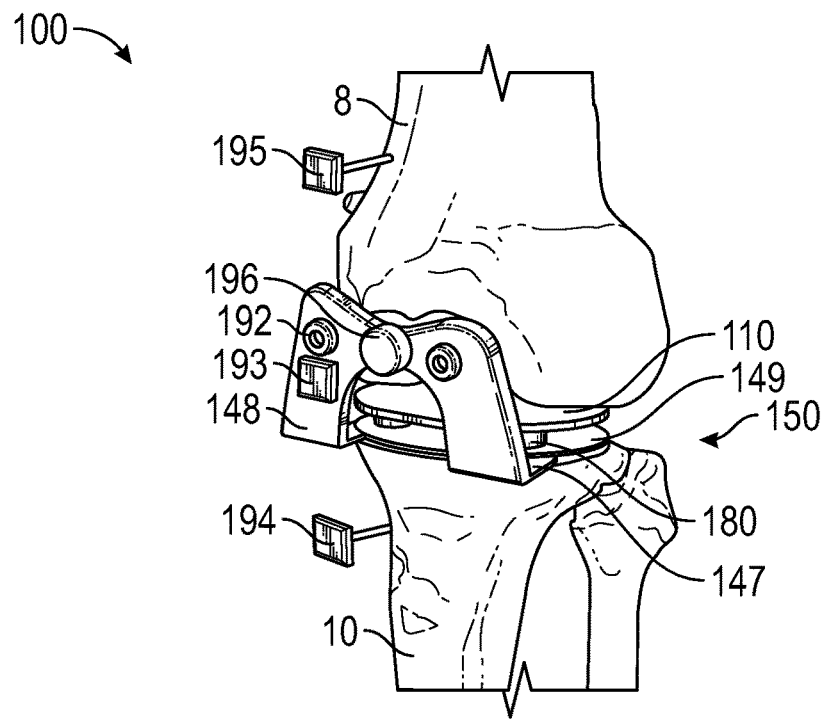
FIGS. 29-32 illustrate an alternate embodiment of the insert of FIGS. 25-28.
Figure 30:
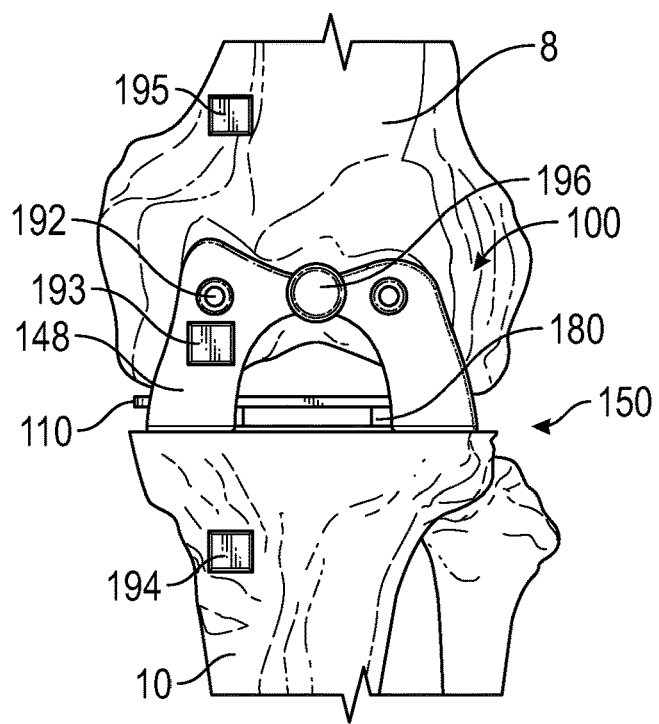
Figure 31:
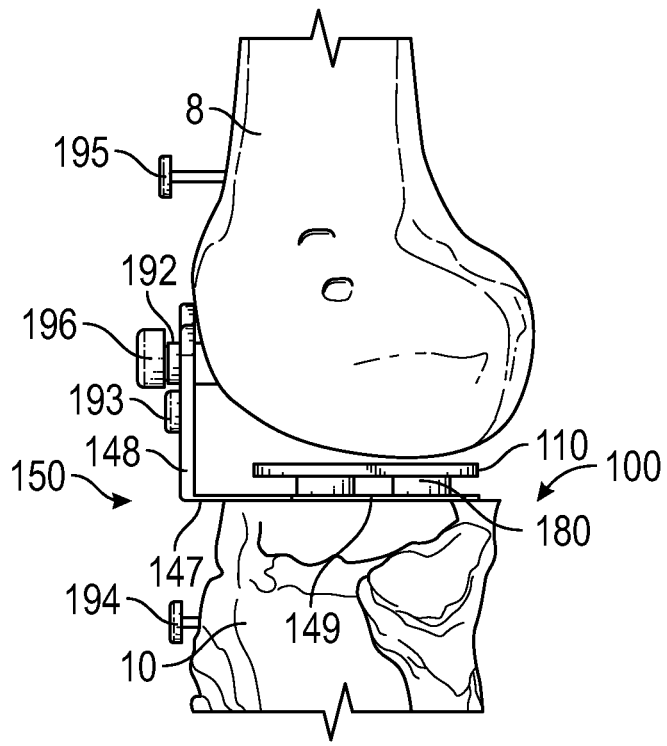
Figure 32:
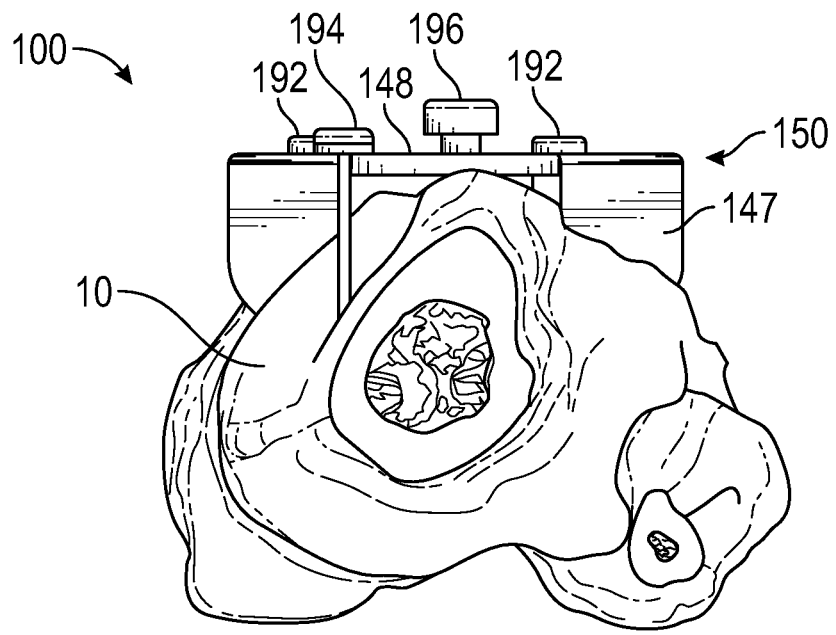
Figure 33:
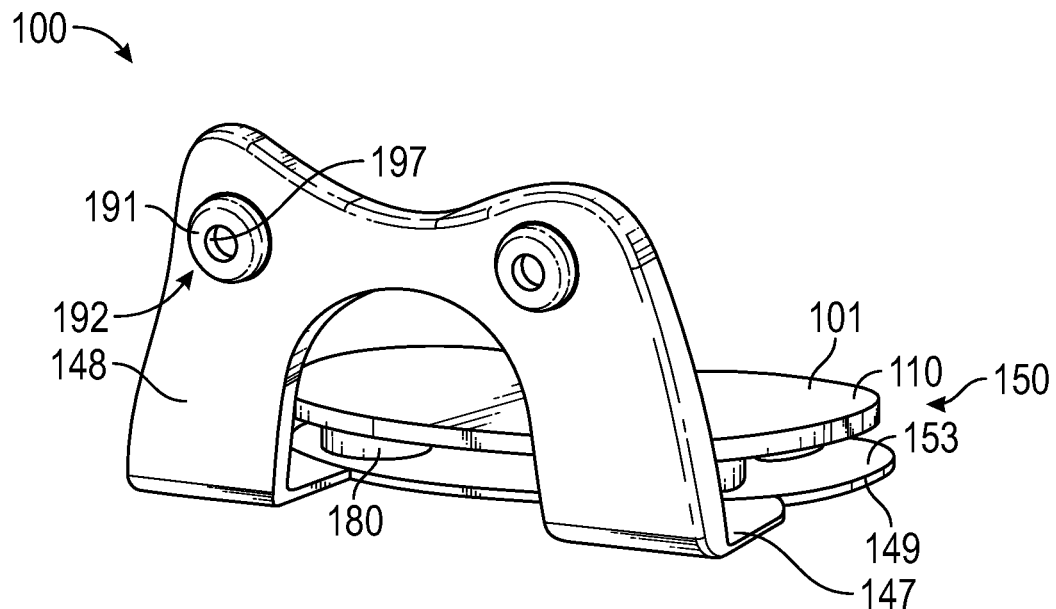
FIGS. 33-40 illustrate an alternate embodiment of the insert of FIGS. 25-32.
Figure 34:
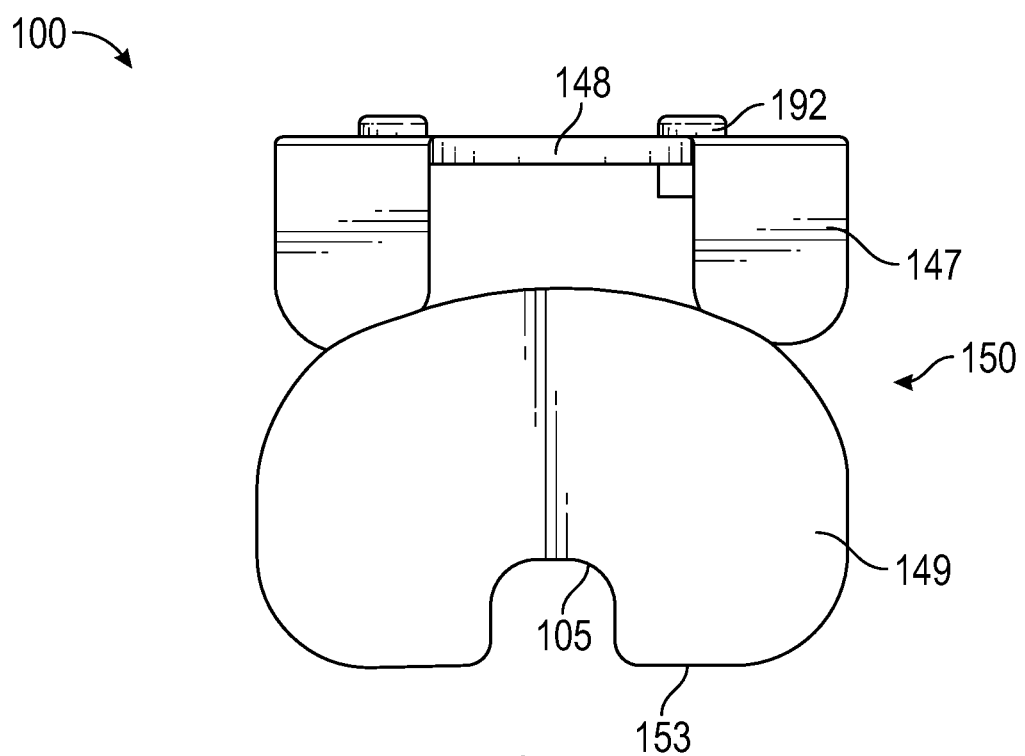
Figure 35:
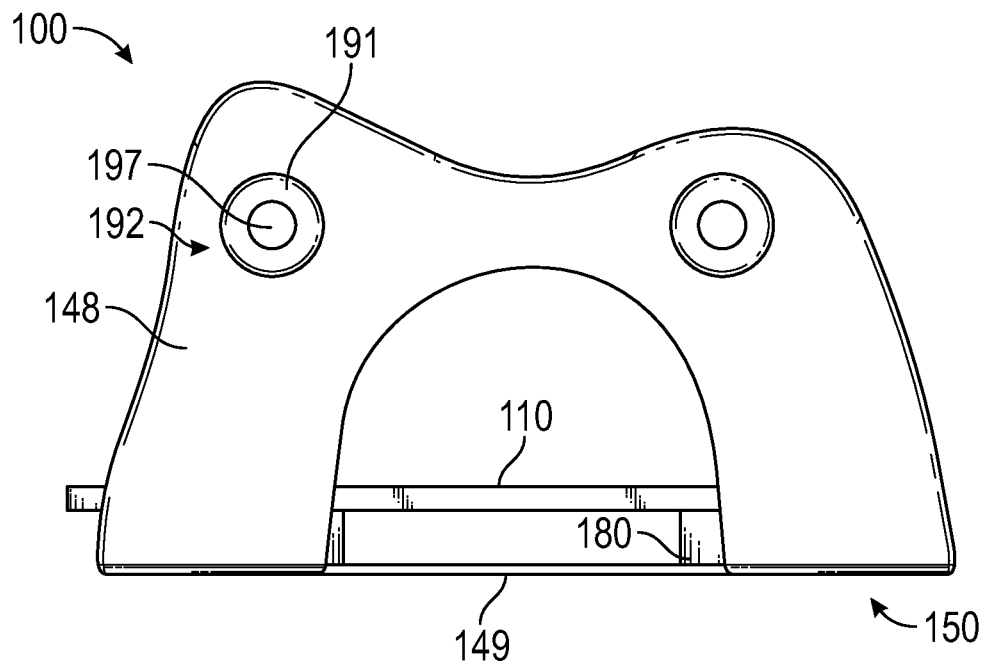
Figure 36:
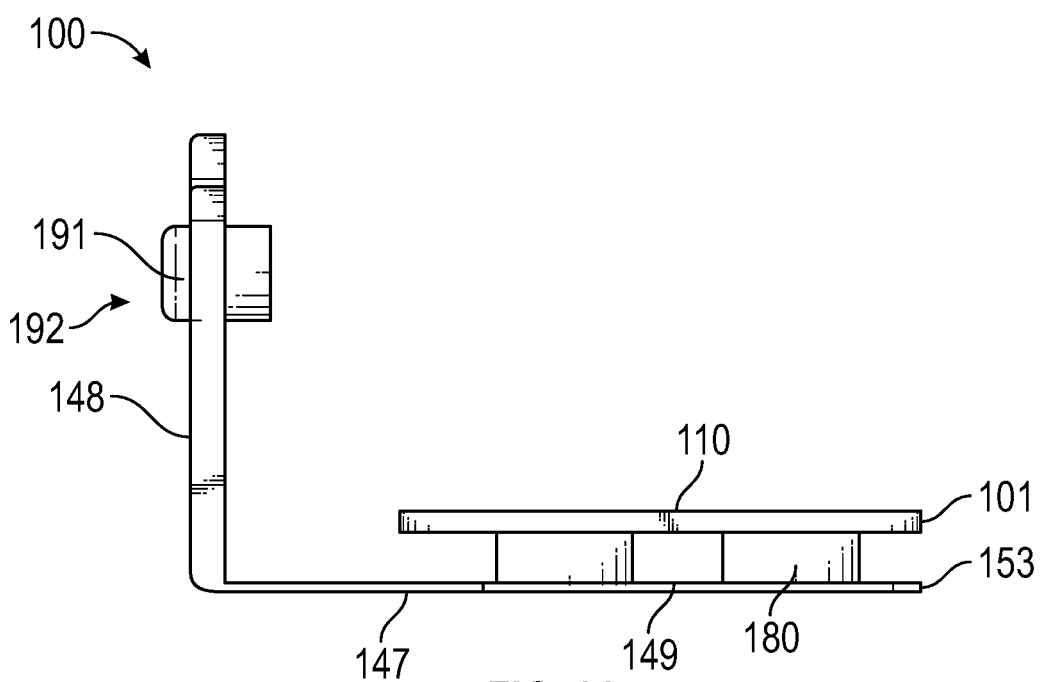
Figure 37:
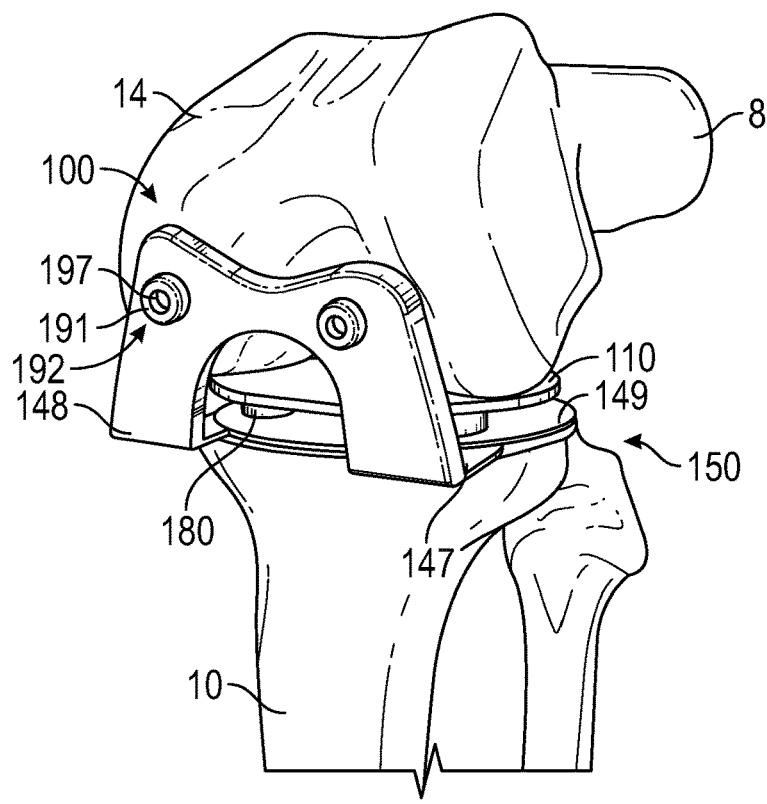
Figure 38:
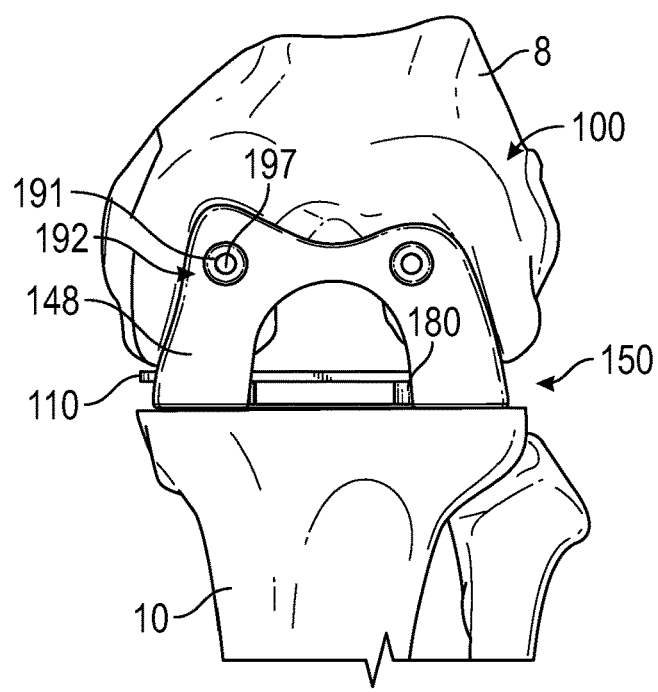
Figure 39:
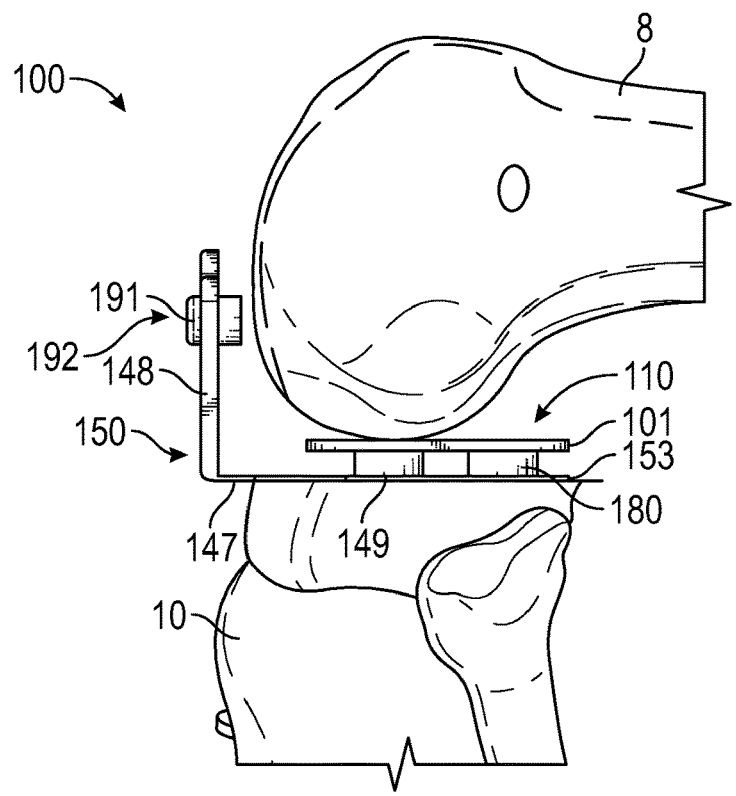
Figure 40:
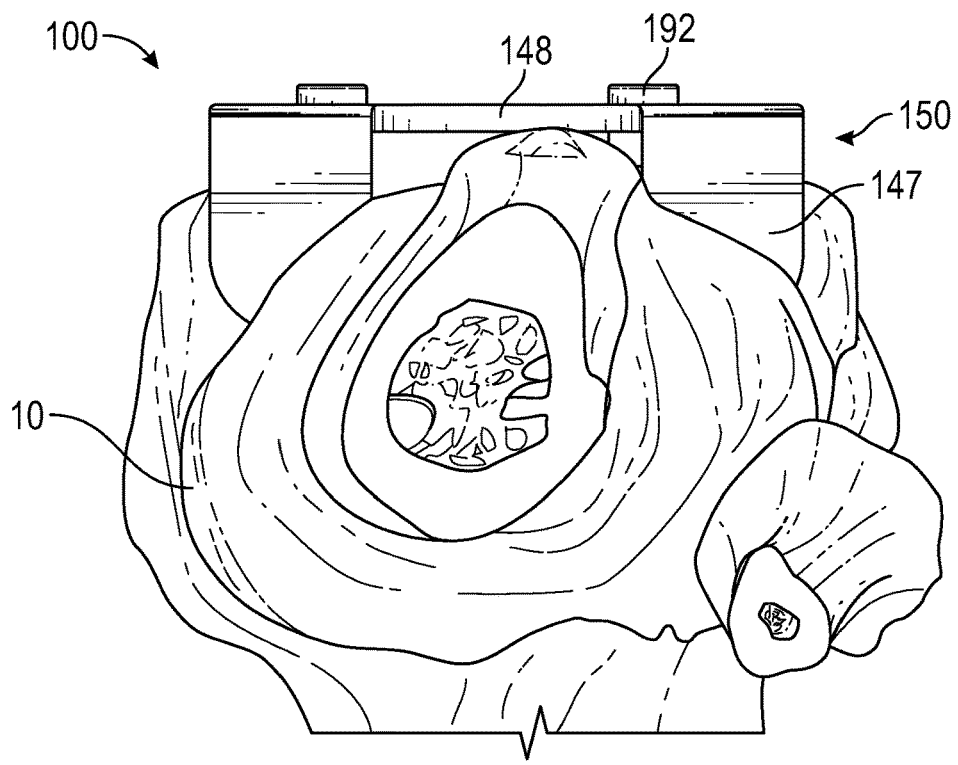
Figure 41:
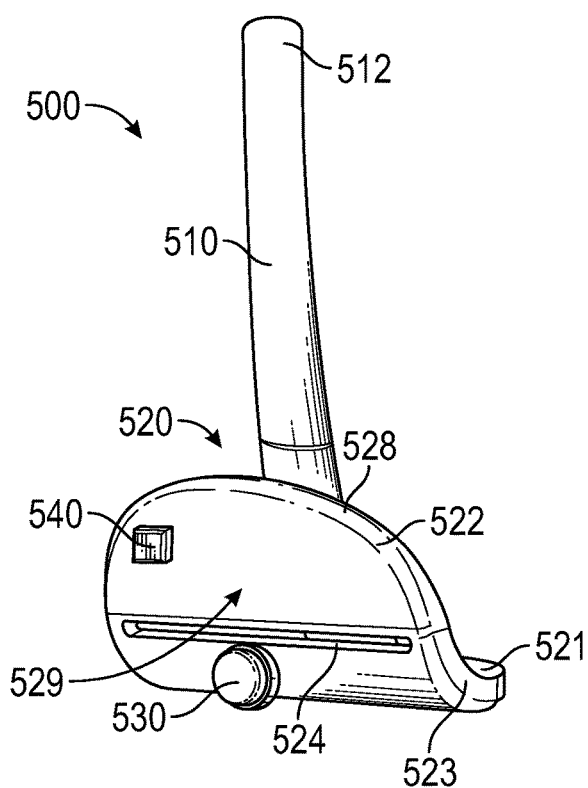
FIGS. 41-48 illustrate an embodiment of a femoral cutting guide.
Figure 42:
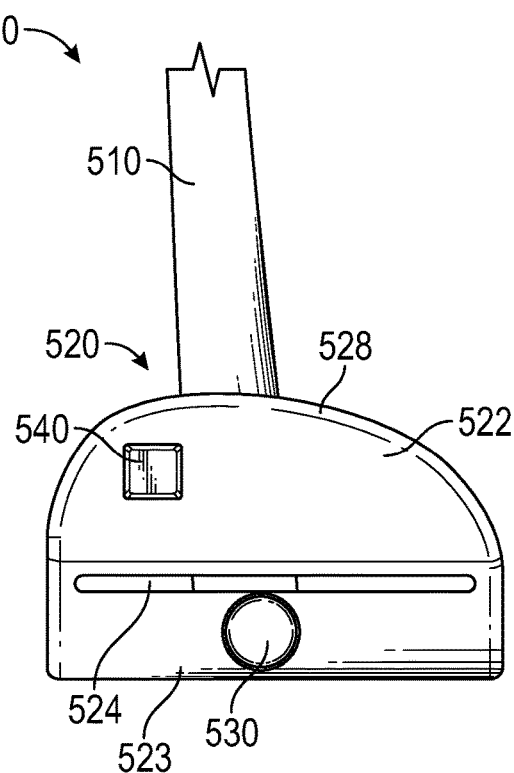
Figure 43:
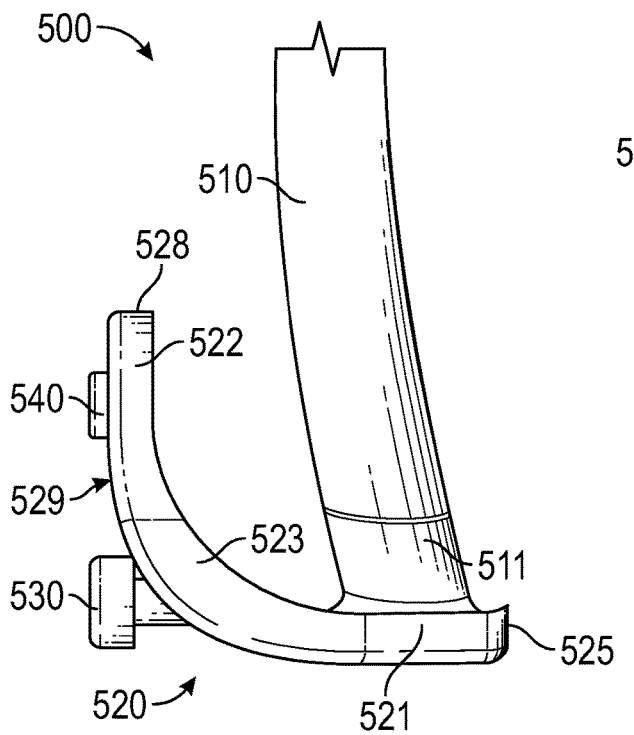
Figure 44:
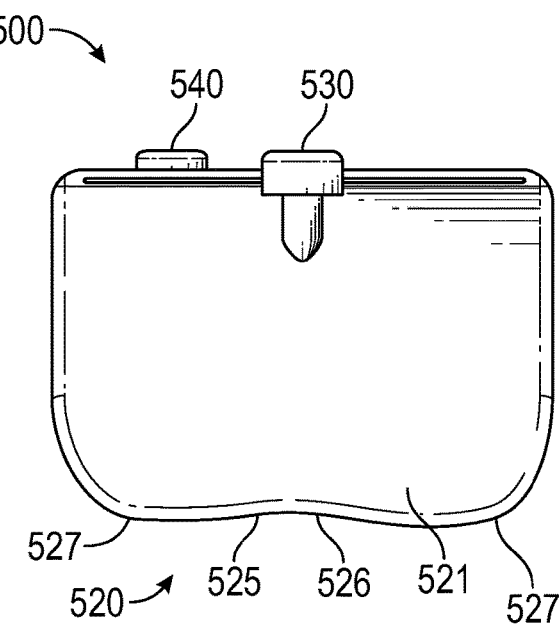
Figure 45:
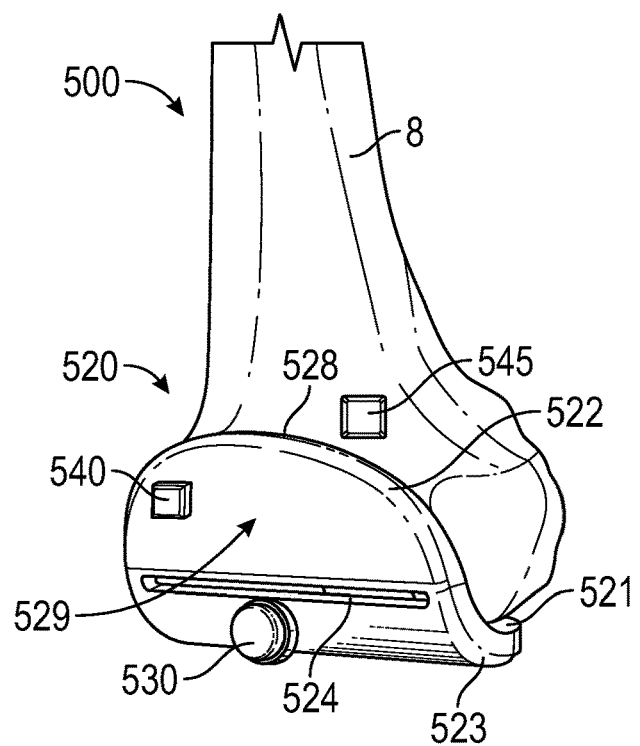
Figure 46:
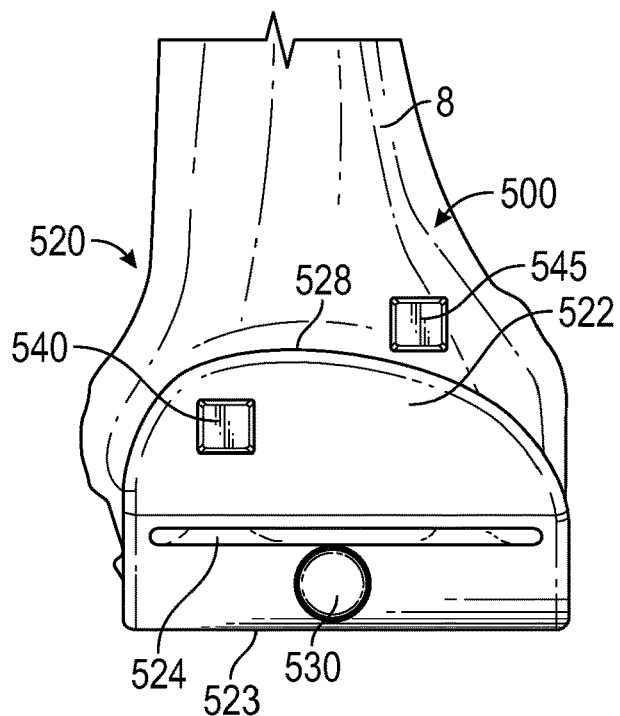
Figure 47:
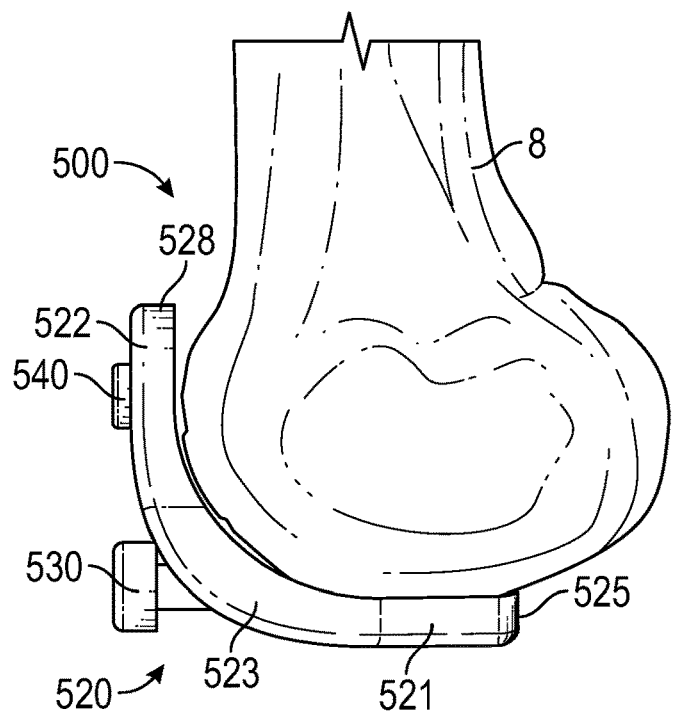
Figure 48:
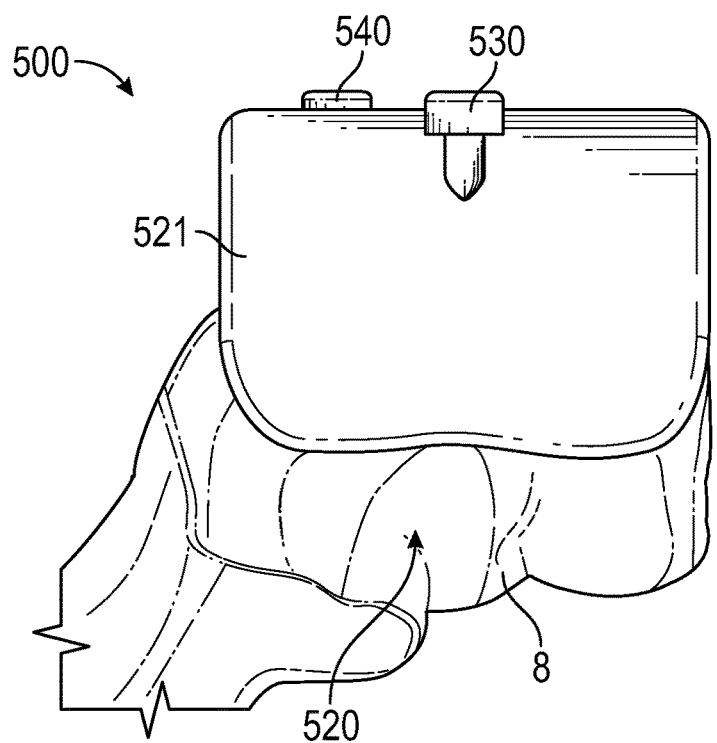
Figure 49:
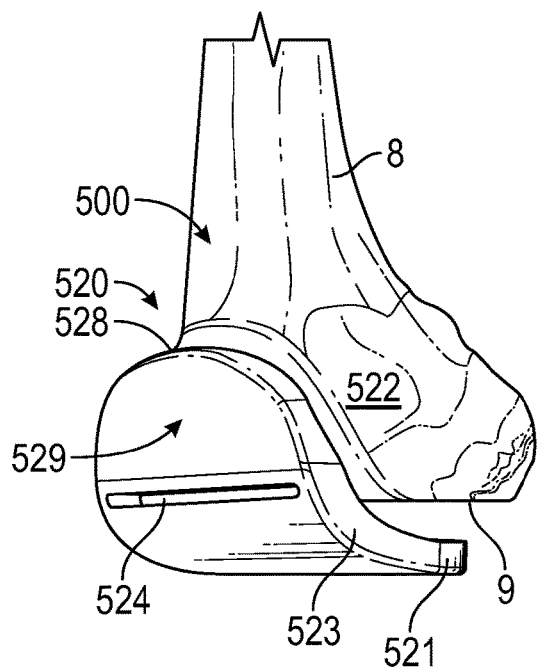
FIGS. 49-52 illustrate an embodiment of the femoral cutting guide of FIGS. 41-48 after the distal femoral cut is made.
Figure 50:
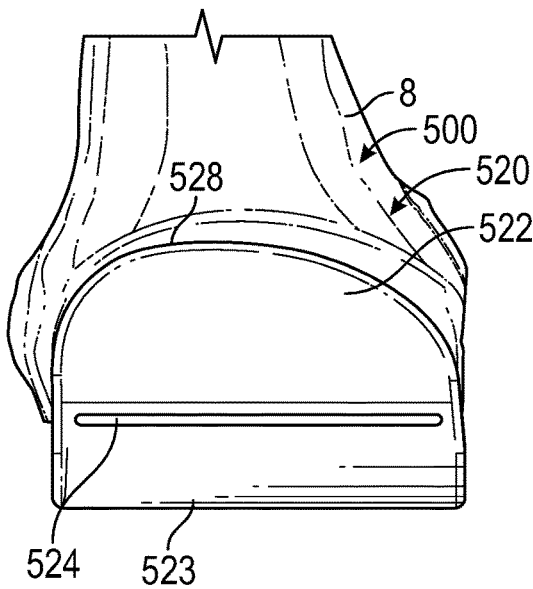
Figure 51:
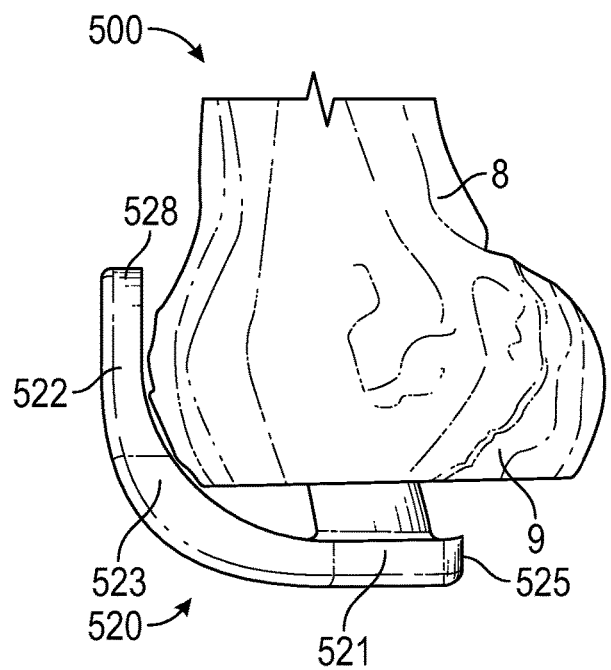
Figure 52:
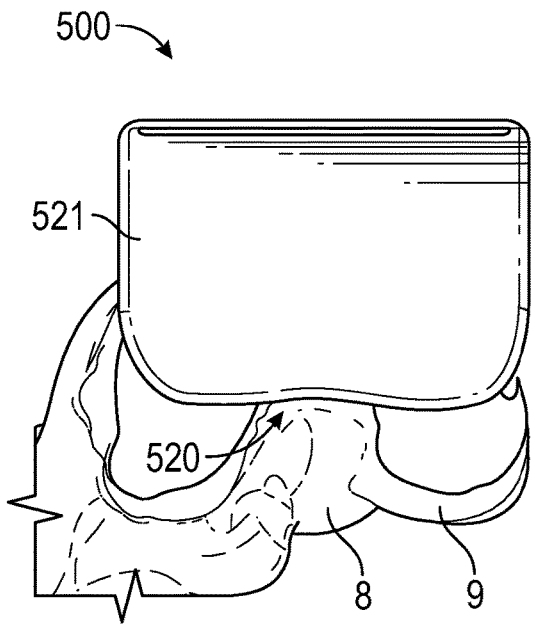
Figure 53:
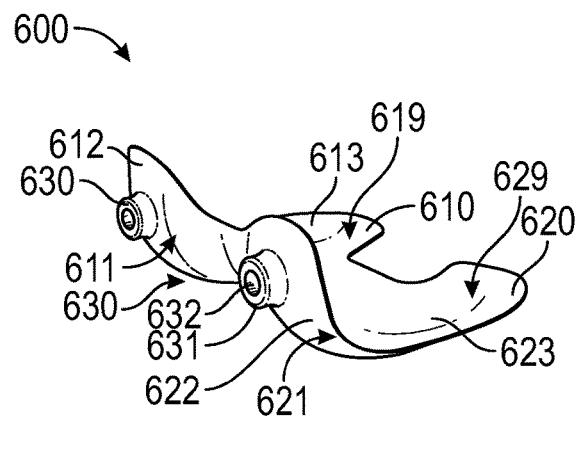
FIGS. 53-60 illustrate an embodiment of a distal femoral balancer.
Figure 54:
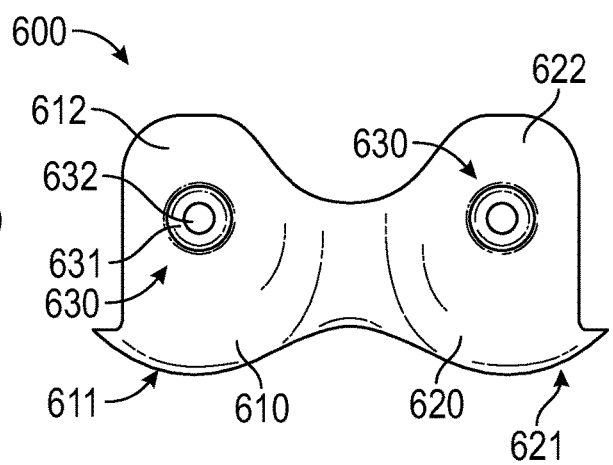
Figure 55:
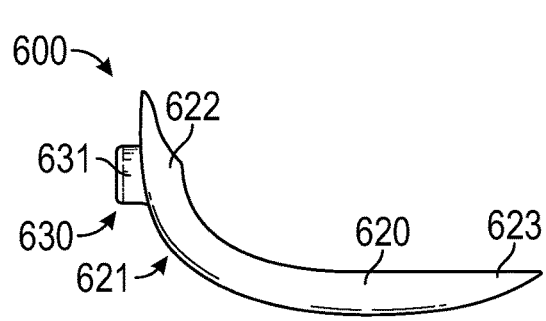
Figure 56:
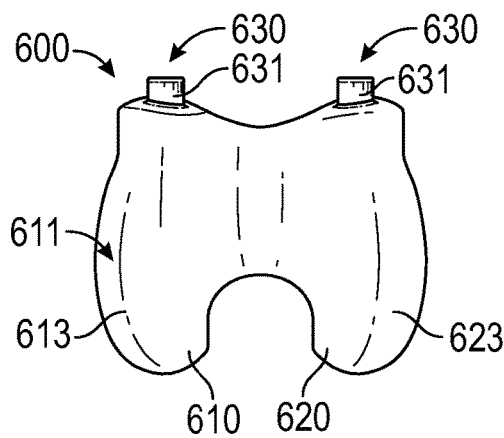
Figure 57:
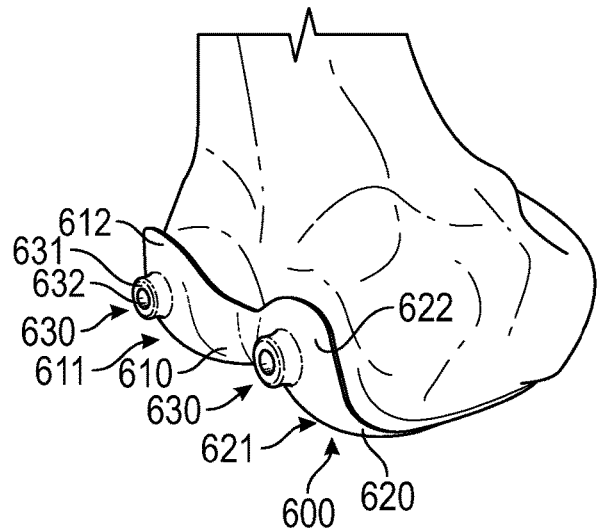
Figure 58:
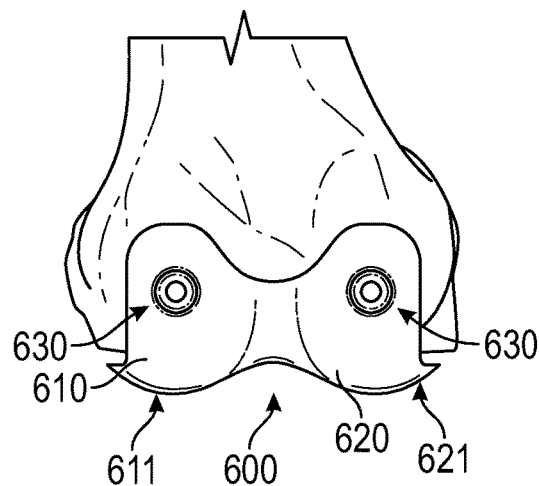

FIGS. 15 and 16 illustrate an embodiment of a joint balancing system including the insert 100 and a cutting guide assembly 400. The cutting guide assembly 400 connects to the insert 100 that is used to guide cutting bone and tissue during balancing of the joint. Cutting guide assembly 400 may be mounted to the insert 100 to provide a surgeon with guides for cutting sections of bone, cartilage or ligaments during the joint balancing.

In the embodiment illustrated, a cutting guide assembly 400 includes cutting guide mounts 402, a cutting guide 406, and mounting fasteners 408, such as pins, screws or bolts. Cutting guide mounts 402 may be attached to the insert 100 at bottom plate 150 or top plate 110.

The cutting guide 406 is attached to the cutting guide mounts 402 using the mounting fasteners 408. Cutting guide 406 includes one or more guiding slots 410. In the embodiment illustrated, cutting guide 406 includes two parallel guiding slots 410. The guiding slots 410 can be used to align and make cuts to the bone, cartilage, ligaments or other tissues during the process of balancing the joint and positioning the artificial joint prostheses.

The guiding slots 410 have flat surfaces that hold and guide the blades of the cutting devices or saws while the surgeon is cutting the bones. The surgeon inserts the cutting saw into the slot of the cutting guide, which helps maintain the location and angle of the guide. In the embodiment described here, the cutting guides are mounted on the plates of the balancing insert such that the cuts are made with the ligaments appropriately tensioned.

In some embodiment, a surface of the top plate or bottom plate may be configured as a grinding (or milling or planing) surface or abrasive surface so that it operates to grind against a corresponding bone structure and grind the bone surface into the appropriate shape or a smoother surface.

In some embodiments, such as the embodiments shown in FIGS. 17-40 the insert 100 includes an integrated mount for a cutting block or guide, such as a tibial cutting guide, a femoral cutting guide, or a posterior femoral cutting guide. The insert 100 with the integrated mount and the cutting guide may form a portion of a joint balancing system, such as the joint balancing systems described herein.

In these embodiments, the insert 100 includes a first plate, a second plate, and one or more actuators. The second plate is adjacent the first plate with the one or more actuators located there between. The second plate includes a plate portion, a transition portion, a mounting portion, and a mounting guide configured to receive the cutting block. The plate portion and the first plate may be substantially parallel and may be aligned on parallel planes. The transition portion may extend from the plate portion protruding beyond the perimeter of the first plate on one side of the insert 100, such as the front end or the side that will be oriented in the anterior direction. The transition portion may extend parallel to the second plate. The mounting portion may extend from the transition portion in a transverse direction relative to the transition portion and in the direction of the first plate relative to the second plate and may extend beyond the first plate, such as beyond the plane of the first plate. The length of the mounting portion may be greater than the distance between the first plate and the second plate. In some embodiments, the mounting portion extends perpendicular to the second plate.

In some embodiments, the transition portion includes a bend towards the direction of the first plate relative to the second plate at the end distal to the plate portion to transition the direction that the plate portion extends to the direction that the mounting portion extends. In some embodiments, the mounting guide may include a flange protruding from the mounting portion and may include a bore extending through the flange and the mounting portion. The bore may be sized to receive a pin for coupling the cutting block or guide to the insert 100.

In the embodiments illustrated, the first plate and the second plate are formed of a rigid material. In other embodiments, the first plate and the second plate are formed of a non-rigid material that inflates, such as a bladder or a balloon.

In the embodiment illustrated in FIGS. 17-24, the second plate is the top plate 110, while the first plate is the bottom plate 150. In the embodiments illustrated in FIGS. 25-40, the second plate is the bottom plate 150, while the first plate is the top plate 110.

FIGS. 17-20 illustrate an embodiment of an insert 100 with an integrated mount for a tibial cutting block. In the embodiment illustrated in FIGS. 17-20, the insert 100 is configured for tibial balancing. Referring to FIGS. 17-20, the insert 100 includes a top plate 110, one or more actuators 180, and a bottom plate 150. The one or more actuators 180 and the bottom plate 150 may be any of combination of the actuators 180 and bottom plate 150 described above. The top plate 110 includes a top portion 109, a top mounting portion 108, and a top transition portion 107. The top portion 109 may include any of the configurations for the top plate 110 described above and is configured to contact the femur 8, such as at a femoral cut or the femoral condyles 14 (refer to FIG. 2). In the embodiment illustrated, the top portion includes a top plate insertion end 101. The top portion 109 may also include a top plate indent 103 extending into the top portion 109 from the top plate insertion end 101. In the embodiment illustrated, the top plate indent 103 is a rectangular slot with rounded corners.

The top mounting portion 108 extends downward and beyond the bottom plate 150. The top mounting portion 108 may extend perpendicular to the top portion 109. In the embodiment illustrated, the top mounting portion 108 includes a body 114, a first leg 116, a second leg 117, and an outer recess 119. The body 114 extends from the top transition portion 107. The legs 116,117 extend downward from the body 114 and may form an outer recess 119 there between. The first leg 116 may extend down further than the second leg 117. The outer recess 119 may assist in mounting the cutting guide, may allow a cut to be made therethrough or may reduce material costs of the insert 100.

The insert 100 may include one or more mounting guides 192 protruding from the top mounting portion 108. In the embodiment illustrated, each leg 116,117 of the top mounting portion 108 is rounded and includes a mounting guide 192. The mounting guides 192 are configured to receive a cutting block, such as cutting guide 406. The cutting block is configured with guides or slots for guiding a tibial cut. The mounting guides 192 may include a bore 197 and a flange 191. The bore 197 may extend through the flange and may extend through the mounting portion 108, such as through the leg. The flange 191 may extend and protrude out from the mounting portion 108, such as the leg, and may be coaxial to the bore. Each mounting guide 192 may be configured to receive a mounting fastener, such as a pin, a screw, or a bolt. The pins may be used to mount the cutting block to the top plate 110.

The top transition portion 107 may extend outward from the top portion 109 in the same general direction as top portion 109, such as extending parallel to top portion 109, and may extend away from the insertion end 101. The top transition portion 107 may curve downward to top mounting portion 108 distal to the top portion 109. In embodiments, top transition portion 107 curves approximately 90 degrees. As illustrated, top portion 109, top transition portion 107 and top guide portion 108 may be formed as an integral piece. The various components of the insert 100 may be formed of the materials disclosed herein and may include any of the material properties disclosed herein. The insert 100 of FIGS. 17-20 may include and be coupled with any of the features and components previously described herein, such as sensors, actuators, and the various embodiments of the top plate 110 and the bottom plate 150. The inset 100 of FIGS. 17-20 may also be used in conjunction with the joint balancing system 50 described herein or with other types of joint balancing systems.

FIGS. 21-24 illustrate an alternate embodiment of the insert 100 of FIGS. 17-20. Referring to FIGS. 21-24, the insert 100 includes an adjustment device 196. The adjustment device 196 may affixed to the insert 100 at the top mounting portion 108. The adjustment device 196 may be configured to adjust the placement of the guide pins located in the mounting guides 192 based on a comprehensive measurement of relative angles as well as ligament balance. The adjustment device 196 may be, inter alia, a knob, a screw, a slider, a wheel, an inflatable device, or an inflation mechanism. The adjustment device 196 may be manually adjustable or may be adjustable through actuation.

The insert 100 may also include an insert angle sensor 193. The insert angle sensor 193 may also be coupled to the insert 100 at the top mounting portion 108. The insert angle sensor 193 may be used along with a first bone angle sensor 194 that is affixed to the tibia during the procedure to provide the relative angle between the tibia 10 and the insert 100 including top plate 110. Adjustments made using the adjustment device 196 may be made at least partially based on the angle between the tibia and the insert 100.

In the embodiments illustrated in FIGS. 17-24, the top plate 110 articulates with the femoral bone or the femoral component so that the cutting block mounted to the top mounting portion 108 will guide the tibial cut relative to the top late 110 and to the femur 10.

FIGS. 25-28 illustrate an embodiment of an insert 100 with an integrated mount for a femoral cutting block. In the embodiment illustrated in FIGS. 25-28, the insert 100 is configured for tibial balancing and to guide a femoral distal cut. Referring to FIGS. 25-28, the insert 100 includes a top plate 110, one or more actuators 180, and a bottom plate 150. The top plate and the one or more actuators may be any combination of the actuators 180 and top plate 110 described above. The bottom plate 150 includes a bottom portion 149, a bottom mounting portion 148, and a bottom transition portion 147. The bottom portion 149 may include any of the configurations for the bottom plate described above and is configured to contact the tibia 10, such as a tibial cut (refer to FIGS. 29-32). The bottom portion 149 may include a bottom plate insertion end 153. The bottom portion 149 may also include a bottom plate indent 105, as shown and described in previous embodiments.

The bottom mounting portion 148 extends upward and beyond top plate 110. The bottom mounting portion 148 may extend perpendicular to the bottom portion 149. The bottom mounting portion 148 may include two legs extending up from the bottom transition portion 147. The two legs may be joined by a narrow piece of material forming an arch like shape. Each leg may include a mounting guide 192. The mounting guide 192 is configured to receive a cutting block, such as cutting guide 406. The cutting block is configured with guides or slots for guiding a femoral distal cut. The mounting guides 192 may include a bore and a flange. The bore extends through the leg and the flange extends out from the leg coaxial to the bore. Each mounting guide 192 may be configured to receive a pin. The pins may be used to mount the cutting block to the bottom plate 150.

The bottom transition portion 147 may extend outward from the bottom portion 149 in the same general direction as bottom portion 149, such as extending parallel to bottom portion 149, and may extend away from the bottom plate insertion end 153. The bottom transition portion 147 may curve upward to bottom mounting portion 148 distal to the bottom portion 149. In embodiments, the bottom transition portion 147 curves approximately 90 degrees. In the embodiment illustrated, bottom transition portion 147 includes two legs. Each leg extends from bottom portion 149 to a leg of bottom mounting portion 148. The bottom plate 150 including the bottom portion 149, the bottom transition portion 147, and the bottom mounting portion 148 may be formed as an integral piece. The various components of the insert 100 may be formed of the materials disclosed herein and may include any of the material properties disclosed herein. The insert 100 of FIGS. 25-28 may include and be coupled with any of the features and components previously described herein, such as sensors, actuators, and the various embodiments of the top plate 110 and the bottom plate 150. The inset 100 of FIGS. 25-28 may also be used in conjunction with the joint balancing system 50 described herein or with other types of joint balancing systems.

FIGS. 29-32 illustrate an alternate embodiment of the insert 100 of FIGS. 25-28. Referring to FIGS. 29-32, the insert 100 includes an adjustment device 196. The adjustment device 196 may affixed to the insert 100 at the bottom mounting portion 148. The adjustment device 196 may be configured to adjust the placement of the guide pins located in the mounting guides 192 based on a comprehensive measurement of relative angles as well as ligament balance. The adjustment device 196 may be, inter alia, a knob, a screw, a slider, a wheel, an inflatable device, or an inflation mechanism. The adjustment device 196 may be manually adjustable or may be adjustable through actuation.

The insert 100 may also include an insert angle sensor 193. The insert angle sensor 193 may also be coupled to the insert 100 at the bottom mounting portion 108. The insert angle sensor 193 may be used along with multiple bone angle sensors, such as a first bone angle sensor 194 and a second bone angle sensor 195, that are affixed to adjacent bones, such as the tibia, femur, and patella, during the procedure to provide the relative angles between adjacent bones, and the insert 100 including bottom plate 150. In the embodiment illustrated, the first bone angle sensor 195 is affixed to the tibia and the second bone angle sensor 195 is affixed to the femur during the procedure to provide the relative angles between the tibia 10, the femur 8, and the insert 100 including bottom plate 150. Adjustments made using the adjustment device 196 may be made at least partially based on these angles.

In the embodiments illustrated in FIGS. 25-32, the bottom plate 110 articulates with the tibial bone or the tibial component so that the cutting block mounted to the bottom mounting portion 108 will guide the tibial cut relative to the bottom plate 150 and to the tibia 8.

FIGS. 33-40 illustrate an alternate embodiment of the insert 100 of FIGS. 25-32. In this embodiment, the insert 100 is configured for tibial balancing and to guide a femoral posterior cut. The various components of the insert illustrated in FIGS. 25-32 may be the same or similar to the components of the embodiments illustrated in FIGS. 25-32 including the top plate 110, the bottom plate 150, and the one or more actuators 180. While FIGS. 33-40 do not show the various angle sensors and the adjustment device 196, the insert 100 of FIGS. 33-40 may include the various angle sensors and the adjustment device 196. In some embodiments, the lengths and sizes of the bottom transition portion 147 and the bottom mounting portion 148 to may differ from other embodiments to position the cutting block for the femoral posterior cut. In other embodiments, the cutting block may differ rather than the bottom transition portion 147 and the bottom mounting portion 148 to position the guides of the cutting block for the femoral posterior cut rather than the femoral distal cut.

As illustrated in FIGS. 37-40, the knee is in flexion, such as 90 degrees flexion when for the femoral posterior cut.

The bottom plate 150 including the bottom portion 149, the bottom transition portion 147, and the bottom mounting portion 148 may be formed as an integral piece. The various components of the insert 100 may be formed of the materials disclosed herein and may include any of the material properties disclosed herein. The insert 100 of FIGS. 33-40 may include and be coupled with any of the features and components previously described herein, such as sensors, actuators, and the various embodiments of the top plate 110 and the bottom plate 150. The inset 100 of FIGS. 33-40 may also be used in conjunction with the joint balancing system 50 described herein or with other types of joint balancing systems.

A method of cutting a bone during a joint surgery is also disclosed. In embodiments, such as those disclosed in FIGS. 15-40, the method includes inserting the insert 100 into the joint, such as a knee. The method also includes deploying the actuators, such as inflating the bellows 182. The method further includes drilling a hole or holes into the bone, such as the femur 8 or tibia 10. The pin guides 402 or mounting guides 192 may be used to guide the drill. The method yet further includes placing a pin into each hole(s) in the bone. The pin guides 402 or mounting guides 192 may also be used to guide the pin(s) 408 into the bone. The method still further includes mounting the cutting guide 406 onto the pins 408 as shown in FIG. 16. The cutting guide 406 may be mounted adjacent the pin guides 402 or the mounting portion 108, 148 of the insert 100. The method further includes cutting the bone using the guiding slot 410 to guide the cut. The cut may be made parallel to the plate opposite the bone, at a fixed distance from the plate or at a predetermined angle relative to the plate. For example, in the embodiments shown in FIGS. 15 and 25-40 the cut may be made parallel to the bottom plate 150, at a fixed distance from the bottom plate 150, or at a predetermined angle relative to the bottom plate 150. In the embodiments shown in FIGS. 17-24 the cut may be made parallel to the top plate 110, at a fixed distance from the top plate 150, or at a predetermined angle relative to the top plate 110.

The method may also include adjusting the angle and/or location of the pin guides 402 or the mounting guides 192. Adjusting the angle and/or location of the pin guides 402 or the mounting guides 192 may include manually adjusting or actuating the adjustment device 196. Adjusting the angle and or location of the pin guides 402 or the mounting guides 192 may be performed prior to cutting the bone. Each of the steps described herein may be performed by a medical professional, such as a surgeon. Each of the steps described may be performed in conjunction with the methods and steps for the methods described in conjunction with the embodiments disclosed in FIGS. 1-14. Each of the embodiments of the insert 100 disclosed in FIGS. 17-10 may be used in conjunction with the joint balancing system 50 and with the methods for using the joint balancing system 50.

FIGS. 41-48 illustrate an embodiment of a femoral cutting guide 500. In the embodiment illustrated, femoral cutting guide 500 is a distal femoral cutting guide. Cutting guide 500 includes a guide body 520, a blade guiding feature 524, and a guide rod 510. The guide body 520 includes a bottom portion 521, a front portion 522, and a transition portion 523. Bottom portion 521 may have a plate like shape. Bottom portion 521 may include an insertion end 525. The insertion end 525 may be rounded on each side and may include an indent 526. In embodiments, the insertion end 525 includes the shape of a portion of a cassini oval to form the rounded sides 527 and the indent 526.

Transition portion 523 may extend away from bottom portion 521 in the direction opposite the insertion end 525 and curve upward to front portion 522. Transition portion 523 may be a plate with an arcuate shape and may curve approximately 90 degrees.

Front portion 522 may extend in a direction transverse to the direction that bottom portion 521 extends, such as perpendicular to bottom portion 521. Front portion 522 may include a top edge 528. Top edge 528 may be distal to transition portion 523. Top edge 528 may be curved. In the embodiment illustrated, top edge 528 has an asymmetric curve with the apex shifted toward one side so that one side is higher than the other.

Guide body 520 may include a front face 529. Front face 529 may be the surface facing opposite the direction of insertion end 525 and may include the outer surface of front portion and part of the outer surface of transition portion 523.

Blade guiding feature 524 may be a slot or a similar feature configured to guide the distal femoral cut. Blade guiding feature 524 may be located in the guide body 520 and may be adjacent the distal end of transition portion 523.

The guide rod 510 extends from the guide body 520. In the embodiment illustrated, guide rod 510 extends up from bottom portion 521 in the same general direction that transition portion 523 curves towards. Guide rod 510 is configured to be inserted into the intramedullary canal of the femur 8. The guide rod 510 may be shaped to match the shape of the intramedullary canal of the femur 8.

Guide rod 510 includes a base 511 and an end 512. The base 511 adjoins bottom portion 521 and the end 512 is distal to bottom portion 521. The base 511 may be larger than the end 512 with the guide rod 510 tapering down from the base 511 to the end 512. The guide rod 510 may have an arcuate shape. In the embodiment illustrated, guide rod 510 extends up in an initial direction that is less than ninety degrees relative to bottom portion 521 and may curve towards extending in a direction that is closer to ninety degrees relative to bottom portion 521 than the initial direction.

Femoral cutting guide 500 may also include a cutting guide adjustment device 530, a cutting guide sensor 540, and one or more bone angle sensors 545. The bone angle sensor(s) 545 may be affixed to the bone structures adjacent the joint, such as the femur, tibia, or the patella. In the embodiment illustrated, the bone angle sensor 545 is located on the femur. The cutting guide adjustment device 530 may be used to adjust the angle of the femoral cutting guide 500 relative to the femur 8 and adjust the location of blade guiding feature 524. The cutting guide adjustment device 530 may be, inter alia, a knob, a screw, a slider, a wheel, an inflatable device, or an inflation mechanism. The cutting guide adjustment device 530 may be manually adjustable or may be adjustable through actuation. The cutting guide sensor 540 may be used with the bone angle sensor(s) 545 to measure the angle between the femoral cutting guide 500 and the femur 8. The cutting guide sensor 540 may be affixed to the guide body 520 at the front surface 529. In the embodiment illustrated, the cutting guide sensor 540 is affixed to the guide body 520 adjacent to the apex of the top edge 528. The bone angle sensor(s) 545 may be separate from the guide body 520 and may be affixed to the femur 8 while the femoral cutting guide 500 is in place, such as while the guide rod 510 is located in the intramedullary canal of the patient.

Femoral cutting guide 500 may be a custom guide that is created specific to the patient. The exact measurements of the various components may be based on various images taken of the joint of the patient, such as the images from x-rays, CT scans, MRIs, and the like. After measuring the patient's joint and creating the femoral cutting guide 500, the guide rod 510 is then inserted into the intramedullary canal of the patient's femur. The angle between the femur 8 and the femoral cutting guide 500 may then be measured. The cutting guide adjustment device 530 may then be used to properly position the femoral cutting guide 500 relative to the femur 8. Once femoral cutting guide 500 is properly positioned, such as being at a predetermined angle relative to the femur 8, the distal femoral cut is made using a cutting tool, such as a saw blade.

FIGS. 49-52 illustrate an embodiment of the femoral cutting guide 500 of FIGS. 41-48 after the distal femoral cut is made. The femoral cutting guide of FIGS. 49-52 may include the various angle sensors and cutting guide adjustment device shown in FIGS. 41-48. As illustrated, the distal femoral cut 9 is parallel to the blade guiding feature 524. After the distal femoral cut 9 is made an insert 100 may be used to balance the joint and to make additional cuts to the femur 8 or to the tibia.

The guide rod 510 and the guide body 520 may be formed as an integral piece. The various components of the femoral cutting guide 500 may be formed of the materials disclosed herein and may include any of the material properties disclosed herein.

A method for performing a femoral cut using the femoral cutting guide 500 is also disclosed. In embodiments, the method includes inserting the guide rod 510 into the intramedullary canal of the femur 8. The guide rod 510 may be inserted so that the guide rod 510 is aligned with the long axis of the femoral shaft. The method also includes cutting the bone at a fixed angle relative to the guide rod 510.

The method may include affixing a bone angle sensor 545 to the femur 8. The method may also include measuring the angle between the cutting guide sensor 540 affixed to the femoral cutting guide and the bone angle sensor 545. The method may yet further include adjusting the angle and position of the blade guiding feature 524. In some embodiments, adjusting the angle and position of the blade guiding feature 524 relative to the femur 8 includes manually adjusting or actuating the adjustment device 530 until the blade guide feature 524 is at the predetermined angle for the cut.

FIGS. 53-60 illustrate an embodiment of a distal femoral balancer 600. The distal femoral balancer 600 may be configured to balance the femur relative to the tibial surface. The balancing may be performed before and after the distal femoral cut. The distal femoral balancer includes a first condyle portion 610 and a second condyle portion 620. The first condyle portion 610 includes a first outer surface 611, a first inner surface 619, a first front portion 612, and a first bottom portion 613. The first outer surface 611 is configured to resemble the surface of femoral condyle and the first inner surface 619 may be configured to receive a femoral condyle and may generally match the shape of the femoral condyle. The first front portion 611 extends up and is configured to be anterior to the femoral condyle, while the first bottom portion 612 extends from the first front portion 611 and is configured to be inferior to the femoral condyle.

The second condyle portion 620 includes a second outer surface 621, a second inner surface 629, a second front portion 622, and a second bottom portion 623. The second outer surface 621 is configured to resemble the surface of femoral condyle and the second inner surface 629 may be configured to receive a femoral condyle and may generally match the shape of the femoral condyle. The second front portion 621 extends up and is configured to be anterior to the femoral condyle, while the second bottom portion 622 extends from the second front portion 621 and is configured to be inferior to the femoral condyle.

The first outer surface 611 and the second outer surface 621 may be modeled after the femoral condyles of the patient's femur.

The distal femoral balancer 600 may also include pin guides 630. A pin guide 630 may be located on each of the first condyle portion 610 and on the second condyle portion 620. In the embodiment illustrated, a pin guide 630 is located on the first front portion 611 and a pin guide is located on the second front portion 621. The pin guides 630 may include a bore 632 and a flange 631. The bore extends through the condyle portion and the flange extends out from the condyle portion and may be coaxial to the bore 632. Each pin guide 630 may be configured to receive a pin and guide pins into the femur 8. The pins may then be used to make a femoral cut after the distal femoral balancer 600 is removed and a cutting block is mounted to the femur via the pins.

Figure 59:
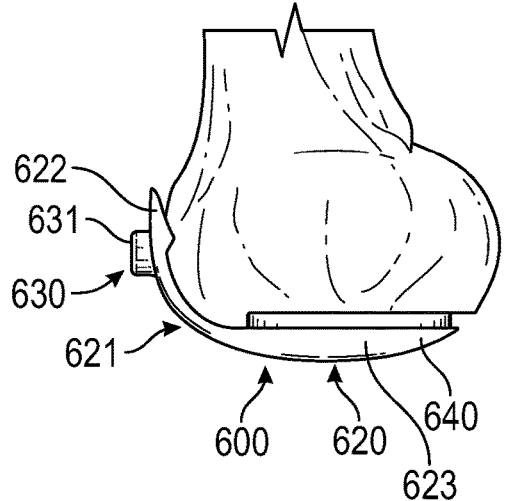
Figure 60:
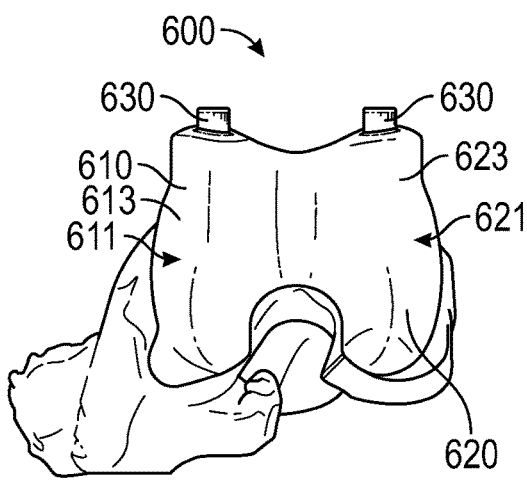
Figure 61:
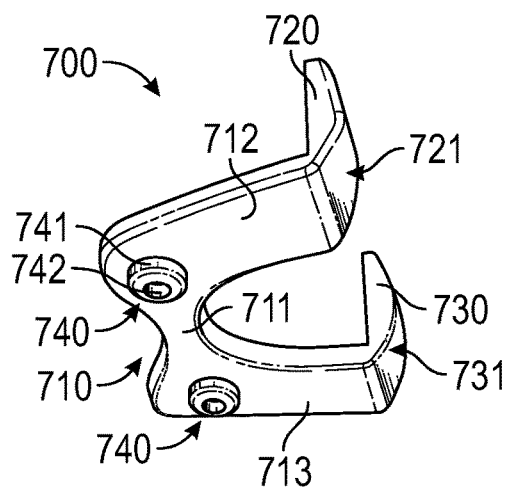
FIGS. 61-68 illustrate an embodiment of a posterior femoral balancer.
Figure 62:
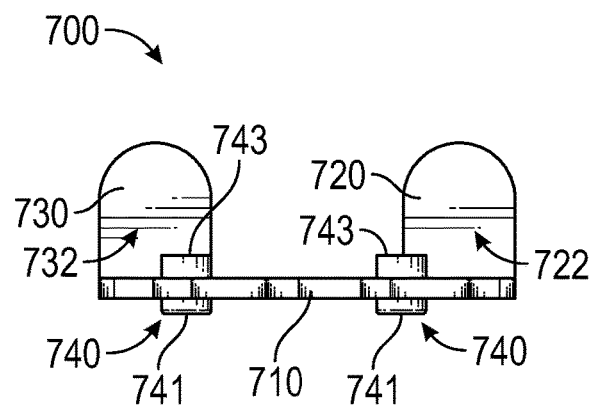
Figure 63:
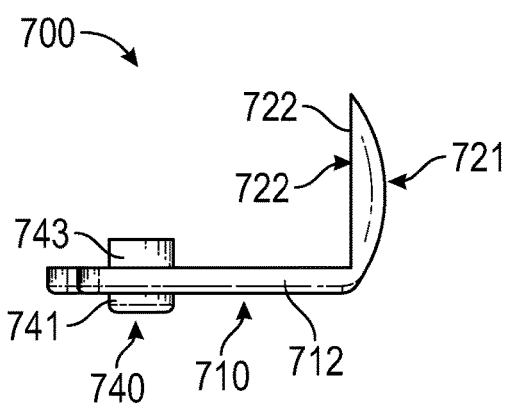
Figure 64:
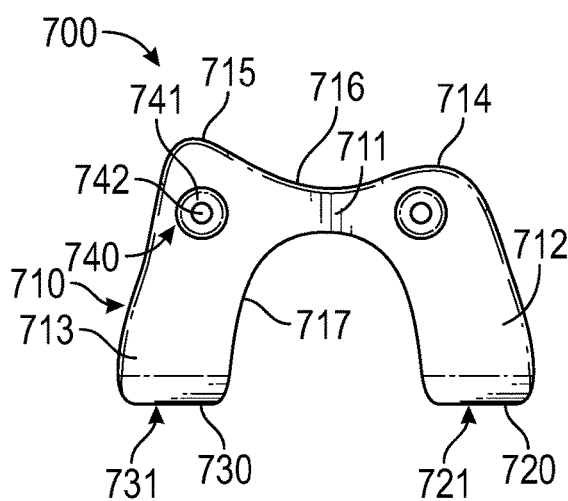
Figure 65:
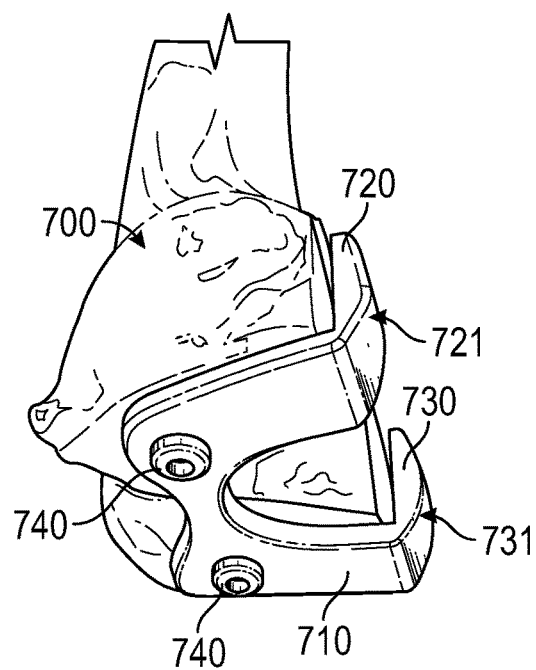
Figure 66:
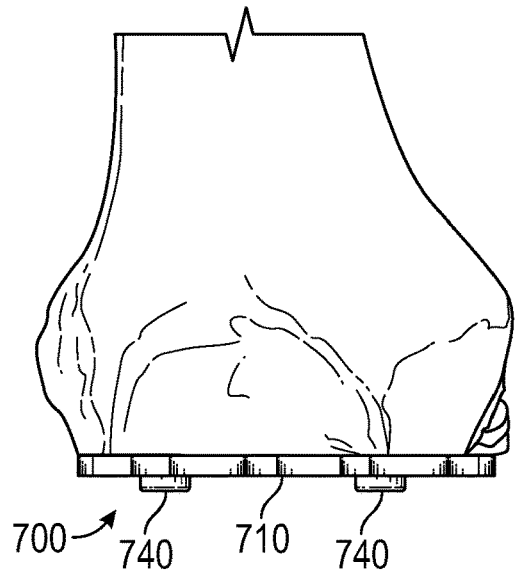

Referring to FIG. 59, the distal femoral balancer 600 may include a balancer actuator 640 for balancing the joint. In the embodiment illustrated, the balancer actuator 640 is configured to be located between the two femoral balancer portions and the distal femoral cut 9. In embodiments where the distal femoral balancer 600 is used prior to the distal femoral cut 9, the femoral balancer actuator 640 is configured to be located between the two femoral balancer condyle portions and the femoral condyles. In embodiments, the balancer actuator includes multiple actuators, such as one actuator between each condyle portion and the adjacent femoral condyle.

In some embodiments, the distal femoral balancer 600 includes a blade guiding feature for making a distal femoral cut, similar to the blade guiding feature of femoral cutting guide 500.

The first condyle portion 610, the second condyle portion 620, and the pin guides 630 may be formed as an integral piece. The various components of the distal femoral balancer 600 may be formed of the materials disclosed herein and may include any of the material properties disclosed herein.

The distal femoral balancer 600 may be used to balance the joint. In embodiments, the method includes making a distal femoral cut. Any of the cutting methods and tools described herein may be used to make the cut. In some embodiments, the method includes removing the insert 100 after making the cut. The method also includes placing the distal femoral balancer on the distal femoral cut and deploying the distal femoral balancer 600 to distract the joint. Placing the distal femoral balancer 600 may include locating the distal femoral balancer 600 as shown in the figures and as described herein. The method further includes forming holes into the bone, such as the femur, and placing pins, such as the pins 402 illustrated in FIGS. 15-16, into the holes. The pin guides 630 may be used to make the holes and to place the pins. In embodiments, placing the pins includes locating the pins at a fixed distance and at a fixed angle from the bottom portion of the distracted device. The method may also include mounting a cutting block 400 to the pins and using the guiding slot 410 to make a second cut to the bone.

FIGS. 61-68 illustrate an embodiment of a posterior femoral balancer 700. The posterior femoral balancer 700 is configured to balance the femur 8 in flexion, such as 90 degrees of flexion relative to the tibia. The posterior femoral balancer 700 may be configured to adjust the posterior femoral cuts relative to the tibia and to the distal femoral cut 9. The posterior femoral balancer 700 includes a balancer body 710, a first posterior condyle portion 720, a second posterior condyle portion 730, and posterior pin guides 740.

Balancer body 710 may include a connection portion 711, a first leg 712, and a second leg 713. The connection portion 711 may be a narrow neck connecting the first leg 712 to the second leg 713. The connection portion 711 may be a narrow piece of material forming plate with an arch like shape. The first leg 712 and the second leg 713 are configured to extend along the distal femoral cut 9. The balancer body 710 may generally have a 'U' shape formed by the connection portion 711, the first leg 712 and the second leg 713. The connection portion 711, the first leg 712 and the second leg 713 may form a rounded slot there between.

The first leg 712 may include a first rounded end 714 adjacent the connection portion 711 and distal to the first posterior condyle portion 720. The second leg 712 may include a second rounded end 715 that is adjacent the connection portion 711 and distal to the second posterior condyle portion 730. In some embodiments, the second rounded end protrudes further from the second posterior condyle portion 730 than the first rounded end 714 extends from the first posterior condyle portion 720. The first rounded end 714 and the second rounded end 715 extend further than the connection portion 711 forming an indent 716 there between.

The first posterior condyle portion 720 extends up from balancer body 710 in a direction transverse to the direction that the balancer body 710 extends and may be perpendicular to the balancer body 710. The first posterior condyle portion 720 may extend from the first leg 712. The first posterior condyle portion 720 may include a first posterior inner surface and a first posterior outer surface 721. The first posterior inner surface 722 may be a flat surface and may be adjacent the posterior femoral cut. The first posterior outer surface 721 may resemble the posterior of a femoral condyle.

The second posterior condyle portion 730 extends up from balancer body 710 in the same direction as the first posterior condyle portion 710, a direction transverse to the direction that the balancer body 710 extends, and may be perpendicular to the balancer body 710. The second posterior condyle portion 730 may extend from the second leg 713. The second posterior condyle portion 730 may include a second posterior inner surface and a second posterior outer surface 731. The second posterior inner surface 732 may be a flat surface and may be adjacent the posterior femoral cut. The second posterior outer surface 731 may resemble the posterior of a femoral condyle.

The first posterior outer surface 721 and the second posterior outer surface 731 may be modeled after the posterior portions of the femoral condyles of the patient's femur.

The posterior pin guides 740 may be located on each leg of the balancer body 710. The posterior pin guides 740 may include a bore 742 and a flange 741. The bore 742 extends through the balancer body 710, such as through one of the legs. The flange 741 extends out from the balancer body 710, such as from one of the legs. In embodiments, the flange 741 is coaxial to the bore 742. Each posterior pin guide 740 may be configured to receive a pin and guide pins into the femur 8 at the distal femoral cut 9. The pins may then be used to make a posterior femoral cut after the posterior femoral balancer 700 is removed and a cutting block is mounted to the femur via the pins. In some embodiments, each posterior pin guide includes a second flange 743 extending inward, coaxial to the bore 742.

Figure 67:
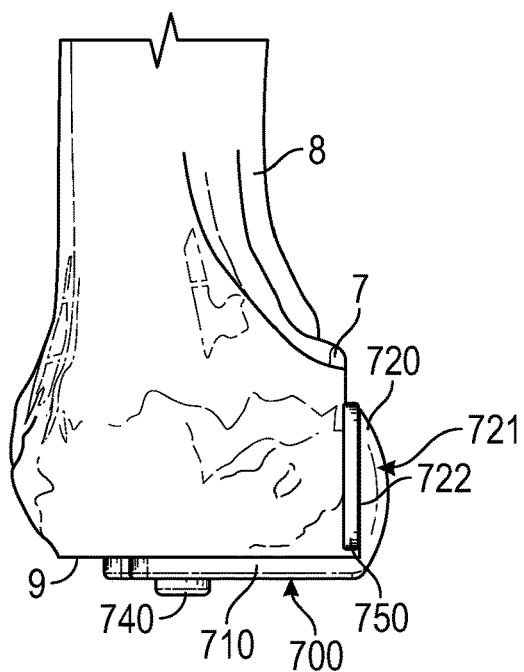
Figure 68:
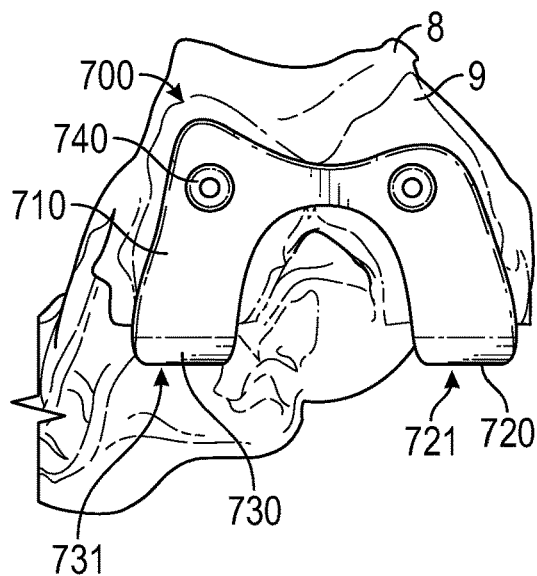
Figure 69:
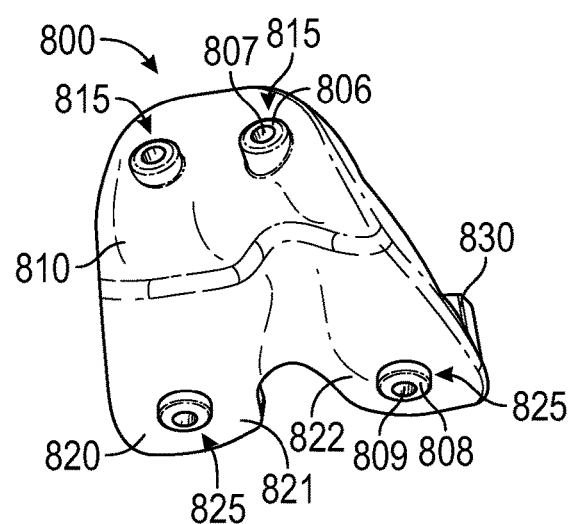
FIGS. 69-76 illustrate an embodiment of a whole femoral balancer.
Figure 70:
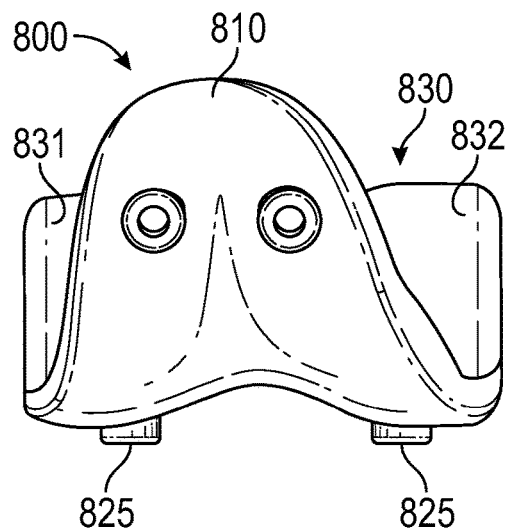
Figure 71:
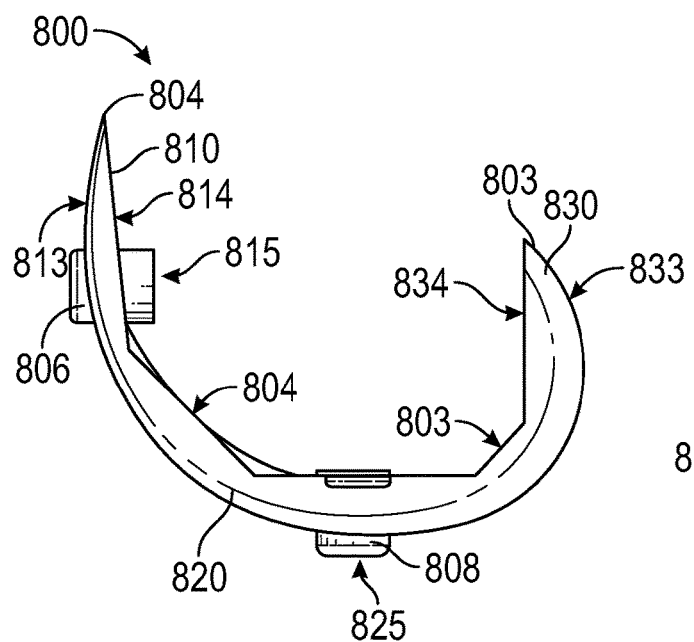
Figure 72:
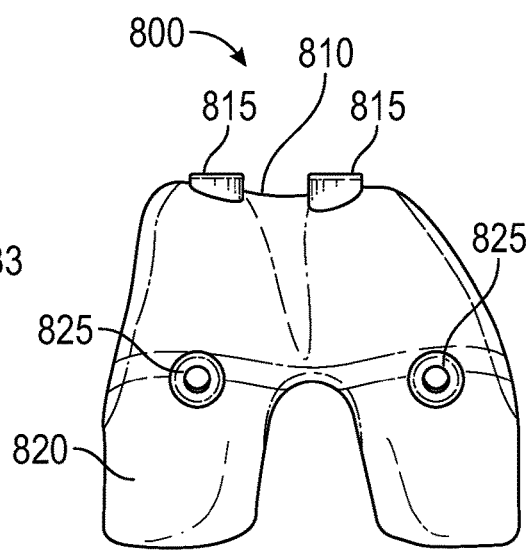
Figure 73:
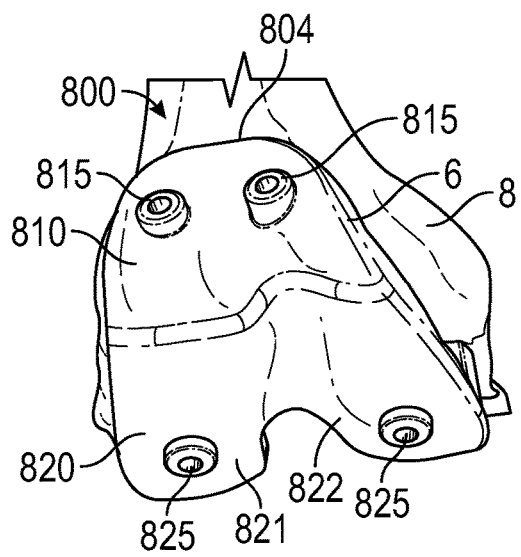
Figure 74:
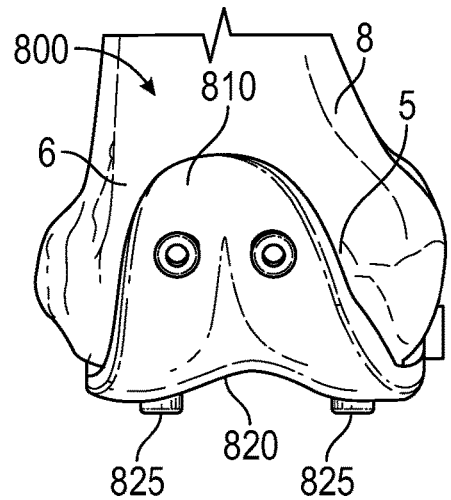

Referring to FIG. 67, the posterior femoral balancer 700 may include a posterior balancer actuator 750. In the embodiment illustrated, the posterior balancer actuator 750 may adjoin the first and second inner surfaces and may adjoin the posterior femoral cut 7. The balancer actuator 750 locates between the first and second posterior condyle portions 720 and 730 and the femur, such as at the posterior femoral cut 7. In embodiments, the posterior balancer actuator 750 includes multiple actuators, such as an actuator between the first posterior condyle portion 720 and the posterior femoral cut 7 and an actuator between the second posterior condyle portion 730 and the posterior femoral cut 7. Once a balance is achieved based on predetermined conditions, pins are inserted into the femur 8 at the distal femoral cut 9 through the posterior pin guides 740. The posterior femoral balancer 700 is then removed and a cutting block is mounted to the femur via the pins. The posterior femoral cuts may then be adjusted using the cutting block, such as cutting block 400.

In some embodiments, the posterior femoral balancer 700 can be mounted to the femur before any posterior femoral cuts are made. In these embodiments, the first and second posterior condyle portions 720 and 730 are contoured to fit the uncut femoral condyles of the patient's knee.

The balancer body 710, the first posterior condyle portion 720, the second posterior condyle portion 730, and the posterior pin guides 740 may be formed as an integral piece. The various components of the posterior femoral balancer 700 may be formed of the materials disclosed herein and may include any of the material properties disclosed herein. While the posterior femoral balancer 700 is described in relation to balancing the posterior of the femoral component of the knee joint, the posterior femoral balancer 700 may be used in balancing the posterior of other bone components and may be used in the balancing of other joints.

The posterior femoral balancer 700 may also be used to balance the joint. In embodiments, the method includes making a posterior femoral cut. Any of the cutting methods and tools described herein may be used to make the cut. In some embodiments, the method includes removing the insert 100 after making the cut. The method also includes placing the posterior femoral balancer 700 on the posterior femoral cut and deploying the posterior femoral cut to distract the joint. Placing the posterior femoral balancer 700 may include locating the posterior balancer 700 as shown in the figures and as described herein. The method further includes forming holes into the bone, such as the femur, and placing pins, such as the pins 402 illustrated in FIGS. 15-16, into the holes. The pin guides 740 may be used to make the holes and to place the pins. In embodiments, placing the pins includes locating the pins at a fixed distance and at a fixed angle from the bottom portion of the distracted device. The method may also include mounting a cutting block 400 to the pins and using the guiding slot 410 to make a second cut to the bone.

FIGS. 69-76 illustrate an embodiment of a whole femoral balancer 800. The whole femoral balancer 800 is configured to balance the alignment of the entire femoral component simultaneously. The shape of the whole femoral balancer 800 may generally be configured to resemble the condyles of a femur 8, such as the patient's femur. The whole femoral balancer 800 may wrap around the end of the femur 8 from the anterior around the distal end to the posterior of the femur. In embodiments, the whole femoral balancer 800 wraps approximately 270 degrees around the femur 8.

The whole femoral balancer 800 includes an anterior portion 810, a distal portion 820, and a posterior portion 830. The anterior portion 810 is configured to be adjacent the anterior of the femur 8, such as adjacent the anterior femoral cut. The anterior portion 810 may be configured to extend around a chamfer cut to the distal portion 820. The anterior portion 810 may include an anterior edge 804. The anterior portion may extend from the anterior edge in a first direction and transition into a second direction that is transverse to the first direction.

The distal portion 820 extends from the anterior portion 810 and is located between the anterior portion 810 and the posterior portion 830. The distal portion 820 may extend in the second direction from the anterior portion 810. The distal portion 820 may include a first distal leg 821 and a second distal leg 822 adjacent the posterior portion 830 to follow the shape of two condyles. In some embodiments, the distal portion 820 separates into the two legs. In other embodiments, each distal leg extends from the anterior portion 810. The distal portion 820 is configured to be adjacent the distal end of the femur 8, such as adjacent the distal femoral cut.

The posterior portion 830 extends from the distal portion 820 and may extend in the same general direction as anterior portion 810. The posterior portion 830 may include a posterior first condyle portion 831 and a posterior second condyle portion 832. The posterior first condyle portion 831 extends from the distal portion 820 and may extend from the first distal leg 821. The posterior second condyle portion 832 extends from the distal portion 820 and may extend from the second distal leg 822.

The whole femoral balancer 800 may also include anterior pin guides 815 and distal pin guides 825. The anterior pin guides 815 are located at the anterior portion 810. The anterior pin guides 815 may include a bore 807 and a flange 806. The bore 807 extends through the anterior portion 810 and the flange 806 extends out from the anterior portion 810 coaxial to the bore 807. Each anterior pin guide 815 may be configured to receive a pin and guide pins into the anterior of the femur 8. The pins may then be used to make a femoral cut after the whole femoral balancer 800 is removed and a cutting block is mounted to the femur via the pins.

The distal pin guides 825 are located at the distal portion 810. The distal pin guides 825 may include a bore 809 and a flange 808. The bore 809 extends through the distal portion 820 and the flange 808 extends out from the distal portion 820 coaxial to the bore 809. Each distal pin guide 825 may be configured to receive a pin and guide pins into the distal end of the femur 8. The pins may then be used to make a femoral cut after the whole femoral balancer 800 is removed and a cutting block is mounted to the femur via the pins.

The anterior portion 810 may include an anterior inner surface 814 and an anterior outer surface 813. The anterior inner surface 814 may adjoin the anterior portion of the femur 8 and may be a flat surface. The anterior inner surface 814 may extend in the first direction. The anterior outer surface 813 may include rounds that form the general shape of the anterior of the femoral component. The anterior portion 810 may also include an anterior chamfer surface 804. The anterior chamfer surface may be adjacent the anterior inner surface and adjacent the distal portion 820. The anterior chamfer surface 804 may extend at a forty-five degrees angle relative to the anterior inner surface 814.

The distal portion 820 may include a distal inner surface 824 and a distal outer surface 823. The distal inner surface 824 may be a flat surface. The distal inner surface 824 may be perpendicular to the anterior inner surface 814. The distal outer surface 823 may include rounds to form the general shape of the distal end of the femur 8 and may match the shape of the distal end of the femoral component. Each of the first and second leg may include a distal inner surface 824 and a distal outer surface 823.

The posterior portion 830 may include a posterior inner surface 834 and a posterior outer surface 833. The posterior inner surface 834 may be a flat surface and may locate adjacent the posterior portion of the condyles. The posterior inner surface 834 may be parallel to the anterior inner surface 814. The posterior outer surface 833 may include the general shape of the posterior portion of the femur and may match the shape of the posterior of the femoral component. Each of the posterior condyle portions may include a posterior inner surface 834 and a posterior outer surface 833. The posterior portion 830 may also include a posterior chamfer surface 803. The posterior chamfer surface 824 may extend from the distal inner surface 824 to the posterior inner surface 834. The posterior chamfer surface 803 may be angled at forty-five degrees relative to the distal inner surface 824 and the posterior inner surface 834.

Each inner surface of the whole femoral balancer 800 may be parallel to a femoral cut or chamfer.

The anterior portion 810, the distal portion 820, the posterior portion 830, the anterior pin guides 815, and the distal pin guides 825 may be formed as an integral piece of material. The various components of whole femoral balancer 800 may be formed of the materials disclosed herein and may include any of the material properties disclosed herein.

Figure 75:
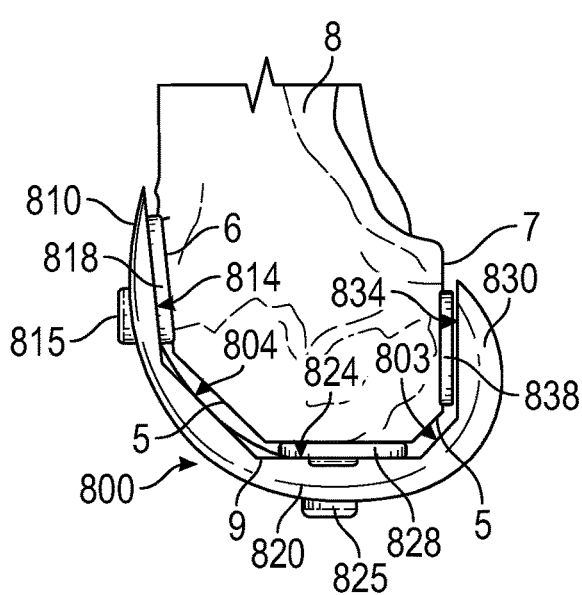
Figure 76:
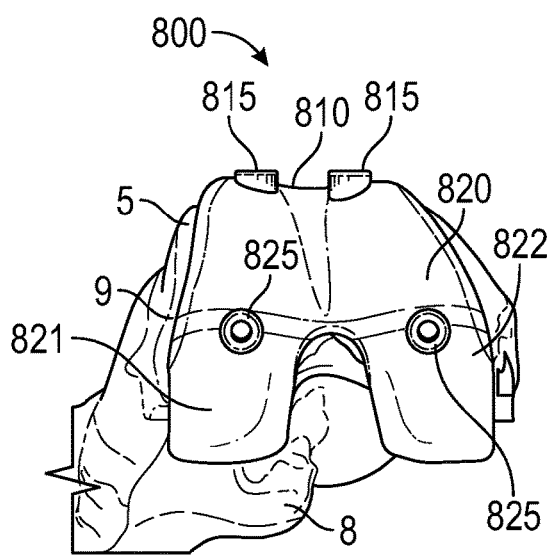
Figure 77:
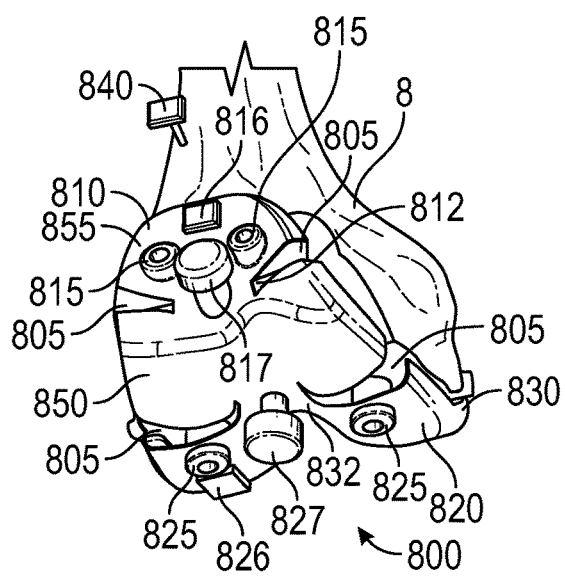
FIGS. 77-80 illustrate an alternate embodiment of the whole femoral balancer of FIGS. 69-76.
Figure 78:
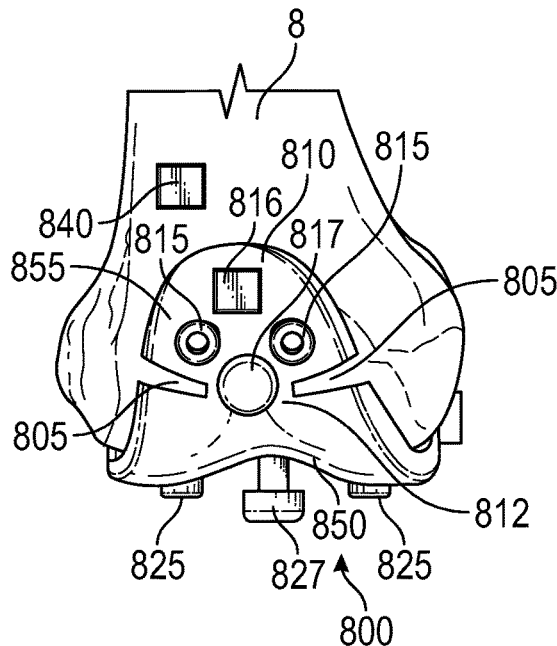
Figure 79:
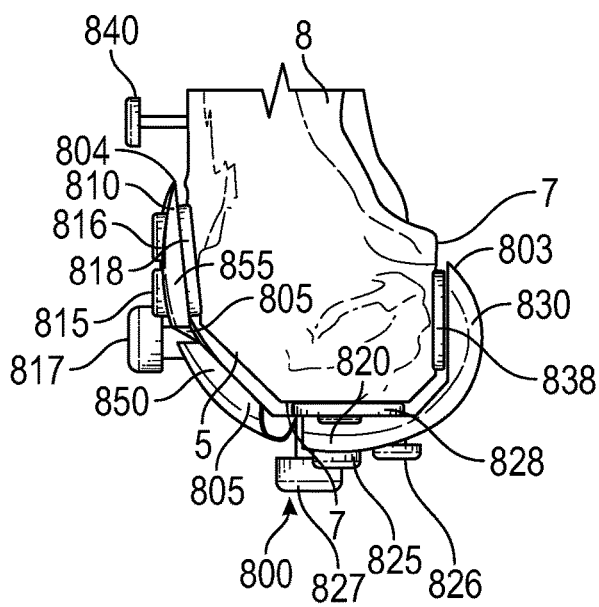
Figure 80:
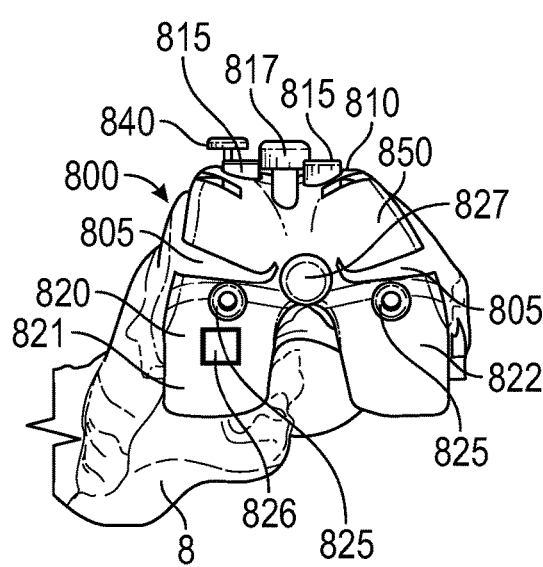

Referring to FIG. 75, the whole femoral balancer 800 may also include an anterior actuator 818, a distal actuator 828, and a posterior actuator 838. The anterior actuator 818 may adjoin and may be joined to the anterior inner surface 814. The anterior actuator 818 locates between the anterior portion 810 and the anterior of the femur 8. In some embodiments, the anterior actuator includes multiple actuators.

The distal actuator 828 may adjoin and may be joined to the distal inner surface 824. The distal actuator 828 locates between the distal portion 820 and the distal end of the femur 8. In some embodiments, the distal actuator 828 includes multiple actuators, such as an actuator between each leg and the distal end of the femur 8.

The posterior actuator 838 may adjoin and may be joined to the posterior inner surface 834. The posterior actuator 838 locates between the posterior portion 830 and the posterior of the femur 8. In some embodiments, the posterior actuator 838 includes multiple actuators, such as an actuator between each posterior condyle portion.

The actuators may balance the alignment of the entire femoral component. After a predetermined condition of the whole femoral balancer is achieved with the actuators, pins are placed into femur 8 through the anterior pin guides 815 and the distal pin guides 825. In some embodiments, the whole femoral balancer 800 can include other actuators, such as actuators that are configured to be located adjacent the chamfer cuts 5.

In some embodiments, the whole femoral balancer may include one or more blade guiding feature, such as a slot, that can serve as a cutting guide for a cutting instrument.

FIGS. 77-80 illustrate an alternate embodiment of the whole femoral balancer 800 of FIGS. 69-76. In the embodiment illustrated, the anterior portion 810 includes an end portion 855 and a middle portion 850. The upper portion 855 is configured to be located at the anterior of the femoral component. Middle portion 850 is configured to transition between the upper portion 855 and the distal portion 820. The middle portion 850 may be adjacent a chamfer cut 5.

The whole femoral balancer 800 may include a first transition portion 812 and a second transition portion 832. End portion 855 may be joined to middle portion 850 by first transition portion 812 and middle portion 850 may be joined to distal portion 820 by second transition portion 832. In the embodiment illustrated, anterior portion 810, distal portion 820, and posterior portion 830 are an integral piece. In other embodiments, upper portion 855 and middle portion 850 are separate pieces, and distal portion 820 and posterior portion 830 are a separate piece with the pieces linked together. First transition portion 812 may include a link that joins end portion 855 and middle portion 850 together. Second transition portion 832 may include a link that joins middle portion 850 to distal portion 820. Distal portion 820 and posterior portion may be a separate piece. In some embodiments, the first distal leg 821 and the posterior first condyle portion 931 form one piece and the second distal leg 822 and the posterior second condyle portion 832 form another piece.

The whole femoral balancer includes an anterior adjustment device 817 and a distal adjustment device 827. The anterior adjustment device 817 and the distal adjustment device 827 may be, inter alia, a knob, a screw, a slider, a wheel, an inflatable device, or an inflation mechanism. The anterior adjustment device 817 and the distal adjustment device 827 may be manually adjustable or may be adjustable through actuation. The anterior adjustment device 817 may be affixed to anterior portion 810, such as between end portion 855 and middle portion 850 at first transition portion 812. Anterior adjustment device 817 is configured to adjust the angle between the whole femoral balancer 800 and the femur 800 and in particular may be configured to adjust the anterior portion 810 relative to the femoral cuts.

The distal adjustment device 827 may be affixed between middle portion 850 and distal portion 820 at second transition portion 832. Distal adjustment device 827 is configured to adjust the angle between the whole femoral balancer 800 and the femur 800 and in particular may be configured to adjust the middle portion 850, the distal portion 820, and the posterior portion 830 relative to the femoral cuts.

The whole femoral balancer 800 may also include an anterior sensor 816 mounted on the anterior portion 810 and a distal sensor 826 mounted on the distal portion 820. In the embodiment illustrated, the distal sensor 826 is configured to be located adjacent the distal end of the femur 8. The anterior sensor 816 and the distal sensor 826 may be used in conjunction with one or more bone angle sensor(s) 840 to determine the angle between adjacent bone structure(s), such as the tibia 10, the femur 8, or the patella, and the whole femoral balancer 800. The anterior adjustment device 817 and the distal adjustment device 827 may then be used to adjust the whole femoral balancer until the angles fall within predetermined values that signify a balanced condition.

The whole femoral balancer 800 may also include a number of relief slots 805 located adjacent the first transition portion 812 between end portion 855 and middle portion 850, and adjacent the second transition portion 832 between middle portion 850 and distal portion 820. The relief slots 805 may reduce the rigidity of the whole femoral balancer 800 and may reduce the effects of the anterior adjustment device 817 on the distal portion 820 and the effects of the distal adjustment device 827 on the anterior potion 810. The embodiment illustrated in FIGS. 77-80 also includes an anterior actuator 818, a distal actuator 828, and a posterior actuator 838. In embodiments, the actuators are used to obtain an initial balance of the whole femoral balancer 800. The adjustment devices may then be used in conjunction with the angle sensors to adjust the relative position of anterior portion 810, distal portion 820, and posterior portion 830 to refine the balance of the whole femoral balancer 800. While the whole femoral balancer 800 is described in conjunction with balancing the knee joint and in particular the femur, the whole femoral balancer 800 can be used in the balancing of other joints and of other bone structures.

The whole femoral balancer 800 may also be used to balance the joint. In embodiments, the method includes placing the whole femoral balancer 800 over the femoral component. Placing the whole femoral balancer 800 may include locating the whole femoral balancer 800 as shown in the figures and described herein. The method also includes cutting the bone, such as performing anterior, distal and posterior cuts to the femoral component. The cuts may be made before or after placing the whole femoral balancer 800 over the femoral component. The method also includes deploying the whole femoral balancer 800 to distract the joint.

The method may also include forming holes into the bone, such as into the femur, and placing pins, such as the pins illustrated in FIGS. 15-16, into the holes. The pin guides 815 and 825 may be used to make the holes and to place the pins. One or more sets of holes may be formed and one or more sets of pins may be placed in the holes. In embodiments, placing the pins includes locating the pins at a fixed distance and at a fixed angle from a predetermined portion of the distracted device. The method may also include mounting a cutting block 400 to the pins or to one set of pins and using the guiding slot 410 to make a cut to the bone. The method may also include mounting a second cutting block 400 to another set of pins and making another cut to the bone.

In some embodiments, the method includes adjusting the relative angle and position of all or a portion of the whole femoral balancer, such as the anterior portion 810 or the distal portion 820. Adjusting the relative angle and position of all or a portion of the whole femoral balancer may include manually adjusting or actuating the anterior adjustment device and/or the distal adjustment device 827. In some embodiments, the method also includes measuring the angle of all or a portion of the whole femoral balancer 800 relative to the bone, such as the femur 8. Measuring the angle of all or a portion of the whole femoral balancer relative to the bone may include measuring the relative angle between the anterior sensor 816 and the bone sensor 840 and measuring the relative angle between the distal sensor 826 and the bone sensor 840. Other sensors, such as a sensor located on the posterior portion 830 may also be used. The method may include affixing a bone sensor 840 to the bone. The step of adjusting the relative angle and position of the whole femoral balancer may be performed prior to making the cuts.

Those of skill will appreciate that the various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the design constraints imposed on the overall system. Skilled persons can implement the described functionality in varying ways for each particular application, but such implementation decisions should not be interpreted as causing a departure from the scope of the invention. In addition, the grouping of functions within a module, block, or step is for ease of description. Specific functions or steps can be moved from one module or block without departing from the invention.

The various illustrative logical blocks and modules described in connection with the embodiments disclosed herein can be implemented or performed with a general purpose processor, a digital signal processor (DSP), application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor (e.g., of a computer), or in a combination of the two. A software module can reside in RAM memory, flash memory, ROM memory, EPROM memory, EEPROM memory, registers, hard disk, a removable disk, a CD-ROM, or any other form of storage medium. An exemplary storage medium can be coupled to the processor such that the processor can read information from, and write information to, the storage medium. In the alternative, the storage medium can be integral to the processor. The processor and the storage medium can reside in an ASIC.

While various embodiments have been described above, it should be understood that they have been presented by way of example only, and not of limitation. The breadth and scope should not be limited by any of the above-described exemplary embodiments. Where this document refers to technologies that would be apparent or known to one of ordinary skill in the art, such technologies encompass those apparent or known to the skilled artisan now or at any time in the future. In addition, the described embodiments are not restricted to the illustrated example architectures or configurations, but the desired features can be implemented using a variety of alternative architectures and configurations. As will become apparent to one of ordinary skill in the art after reading this document, the illustrated embodiments and their various alternatives can be implemented without confinement to the illustrated example. One of ordinary skill in the art would also understand how alternative functional, logical or physical partitioning and configurations could be utilized to implement the desired features of the described embodiments. Hence, although the present disclosure, for convenience of explanation, depicts and describes an insert for balancing a knee joint, it will be appreciated that the insert in accordance with this disclosure can be implemented in various other configurations and can be used to balance various other types of joints, such as hip, shoulder, ankle, elbow, and spine joints.

Furthermore, although items, elements or components may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

What is claimed is:

1. An insert for balancing a joint during repair of the joint, the insert comprising:
   a first plate configured to interface with a first bone structure of a joint;
   a second plate coupled to the first plate, wherein the second plate includes:
      a plate portion spaced apart from the first plate and configured to interface with a second bone structure of the joint, wherein the second bone structure opposes the first bone structure,
      a transition portion extending from the plate portion and protruding beyond a perimeter of the first plate, and
      a mounting portion extending from the transition portion in a transverse direction relative to the plate portion;
   at least one mounting guide, wherein each of the at least one mounting guide includes a bore that extends through the mounting portion; and
   an actuator located between the first plate and the plate portion and configured to apply a force to the first plate and to the plate portion.

2. The insert of claim 1, further comprising at least one sensor configured to determine a spatial relationship between the first plate and the plate portion of the second plate.

3. The insert of claim 1, wherein the first plate is configured to contact a femur of a knee joint during repair of the knee joint, and wherein the second plate is configured to contact a tibia of the knee joint during repair of the knee joint.

4. The insert of claim 1, wherein the actuator is a pneumatic actuator including a bellows made of an inflatable material.

5. The insert of claim 4, wherein the bellows is configured to inflate to thereby pneumatically apply the force to the first plate and to the plate portion.

6. The insert of claim 1, wherein each of the at least one mounting guide includes a flange protruding from the mounting portion, wherein the bore extends through the flange.

7. The insert of claim 6, wherein the flange protrudes from the mounting portion either in a direction away from the plate portion, in a direction toward the plate portion, or both.

8. The insert of claim 1, wherein the plate portion, the transition portion, and the mounting portion are integrally formed.

9. The insert of claim 1, wherein the mounting portion extends from the transition portion in the transverse direction that is toward the first plate.

10. The insert of claim 1, wherein the mounting portion extends from the transition portion in the transverse direction that is away from the first plate.

11. The insert of claim 1, wherein the mounting portion includes:
   a first leg, and
   a second leg,
   wherein a recess is formed between the first leg and the second leg.

12. The insert of claim 11, wherein the first leg and the second leg extend in the transverse direction past the at least one mounting guide.

13. The insert of claim 12, wherein the first leg extends further in the transverse direction than does the second leg.

14. The insert of claim 11, wherein the transition portion includes:
   a first leg extending from the plate portion to the first leg of the mounting portion, and
   a second leg extending from the plate portion to the second leg of the mounting portion,
   wherein a recess is formed between the first leg of the transition portion and the second leg of the transition portion.

15. The insert of claim 1, wherein the at least one sensor includes at least one angle sensor.

16. The insert of claim 1, wherein the first plate includes one or more grooves, and wherein each of the one or more grooves is shaped to match a natural shape of a corresponding condyle of the first bone structure of the joint.

* * * * *